(12) United States Patent
Fernandez Prieto et al.

(10) Patent No.: US 9,271,912 B2
(45) Date of Patent: *Mar. 1, 2016

(54) PERSONAL CARE COMPOSITIONS COMPRISING A PH TUNEABLE GELLANT AND METHODS OF USING

(75) Inventors: Susana Fernandez Prieto, Benicarlo-Castellon (ES); Johan Smets, Lubbeek (BE); Beatriu Escuder Gil, Sant Mateu-Castello (ES); Juan Felipe Miravet Celades, Castellon (ES); Vicent Josep Nebot Carda, Vila-real-Castellon (ES); Paul Robert Tanner, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/495,400

(22) Filed: Jun. 13, 2012

(65) Prior Publication Data

US 2013/0336903 A1 Dec. 19, 2013

(51) Int. Cl.
*A61Q 19/00* (2006.01)
*A61K 8/42* (2006.01)
*A61K 8/44* (2006.01)
*A61K 8/49* (2006.01)

(52) U.S. Cl.
CPC ... *A61K 8/42* (2013.01); *A61K 8/44* (2013.01); *A61K 8/4926* (2013.01); *A61Q 19/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 2,396,278 A | 3/1946 | Otto | |
| 2,438,091 A | 3/1948 | Lynch | |
| 2,486,921 A | 11/1949 | Byerly | |
| 2,486,922 A | 11/1949 | Strain | |
| 2,528,378 A | 10/1950 | Mannheimer | |
| 2,658,072 A | 11/1953 | Kosmin | |
| 2,694,668 A | 11/1954 | Fricke | |
| 2,809,971 A | 10/1957 | Bernstein et al. | |
| 3,152,046 A | 10/1964 | Kapral | |
| 3,236,733 A | 2/1966 | Karsten et al. | |
| 3,332,880 A | 7/1967 | Kessler et al. | |
| 3,439,088 A | 4/1969 | Edman | |
| 3,753,196 A | 8/1973 | Kurtz et al. | |
| 3,755,560 A | 8/1973 | Dickert et al. | |
| 3,761,418 A | 9/1973 | Parran | |
| 3,818,105 A | 6/1974 | Coopersmith et al. | |
| 3,929,678 A | 12/1975 | Laughlin et al. | |
| 3,958,581 A | 5/1976 | Abegg et al. | |
| 3,962,418 A | 6/1976 | Birkofer | |
| 4,032,661 A | 6/1977 | Rowsell et al. | |
| 4,089,945 A | 5/1978 | Brinkman et al. | |
| 4,136,163 A | 1/1979 | Watson et al. | |
| 4,197,865 A | 4/1980 | Jacquet et al. | |
| 4,217,914 A | 8/1980 | Jacquet et al. | |
| 4,230,688 A | 10/1980 | Rowsell et al. | |
| 4,323,683 A | 4/1982 | Bolich, Jr. et al. | |
| 4,345,080 A | 8/1982 | Bolich, Jr. | |
| 4,379,753 A | 4/1983 | Bolich, Jr. | |
| 4,381,919 A | 5/1983 | Jacquet et al. | |
| 4,421,769 A | 12/1983 | Dixon et al. | |
| 4,422,853 A | 12/1983 | Jacquet et al. | |
| 4,470,982 A | 9/1984 | Winkler | |
| 4,507,280 A | 3/1985 | Pohl et al. | |
| 4,529,586 A | 7/1985 | De Marco et al. | |
| 4,663,158 A | 5/1987 | Wolfram et al. | |
| 4,677,120 A | 6/1987 | Parish et al. | |
| 4,885,107 A | 12/1989 | Wetzel | |

(Continued)

FOREIGN PATENT DOCUMENTS

| | | | |
|---|---|---|---|
| DE | EP1352536 | * | 8/1971 |
| WO | 9323028 A1 | | 11/1993 |

OTHER PUBLICATIONS

U.S. Appl. No. 13/495,377, filed Jun. 3, 2012, Susana Fernandez Prieto.

*Primary Examiner* — Robert A Wax
*Assistant Examiner* — Melissa Mercier
(74) *Attorney, Agent, or Firm* — John G. Powell

(57) ABSTRACT

A personal care composition is disclosed comprising a pH tuneable gellant. The pH tuneable gellant has a formula of:

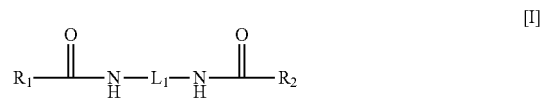

[I]

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group;

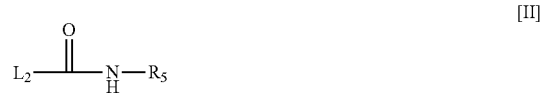

[II]

wherein $R_5$ is an aminofunctional moiety; $L_2$ is a backbone moiety having molecular weight from 14 to 500 g/mol; and at least one of $L_2$ or $R_5$ comprises a pH-sensitive group; and mixtures of [I] and [II]. The personal care composition may take a variety of forms such as a leave-on composition or an emulsion or may comprise one or more actives or agents.

22 Claims, No Drawings

(56) References Cited

U.S. PATENT DOCUMENTS

| | | |
|---|---|---|
| 4,885,311 A | 12/1989 | Parish et al. |
| 4,970,252 A | 11/1990 | Sakuta et al. |
| 5,049,584 A | 9/1991 | Purcell et al. |
| 5,104,646 A | 4/1992 | Bolich, Jr. et al. |
| 5,106,609 A | 4/1992 | Bolich, Jr. et al. |
| 5,124,356 A | 6/1992 | Purcell et al. |
| 5,143,722 A | 9/1992 | Hollenberg et al. |
| 5,236,986 A | 8/1993 | Sakuta |
| 5,266,592 A | 11/1993 | Grub et al. |
| 5,412,004 A | 5/1995 | Tachibana et al. |
| 5,413,781 A | 5/1995 | Giwa-Agbomeirele et al. |
| 5,607,980 A | 3/1997 | McAtee et al. |
| 5,652,228 A | 7/1997 | Bissett |
| 5,654,362 A | 8/1997 | Schulz, Jr. et al. |
| 5,674,478 A | 10/1997 | Dodd et al. |
| 5,681,852 A | 10/1997 | Bissett |
| 5,686,082 A | 11/1997 | N'Guyen |
| 5,686,367 A | 11/1997 | Hayashi |
| 5,725,845 A | 3/1998 | Krog et al. |
| 5,750,122 A | 5/1998 | Evans et al. |
| 5,760,116 A | 6/1998 | Kilgour et al. |
| 5,811,487 A | 9/1998 | Schulz, Jr. et al. |
| 5,837,793 A | 11/1998 | Harashima et al. |
| 5,922,758 A | 7/1999 | Bissett |
| 5,939,082 A | 8/1999 | Oblong et al. |
| 5,993,789 A | 11/1999 | Bonda et al. |
| 5,997,887 A | 12/1999 | Ha et al. |
| 6,113,931 A | 9/2000 | Bonda et al. |
| 6,126,925 A | 10/2000 | Bonda et al. |
| 6,159,485 A | 12/2000 | Yu et al. |
| 6,284,916 B1 | 9/2001 | Bonda et al. |
| 6,524,598 B2 | 2/2003 | Sunkel et al. |
| 6,696,049 B2 | 2/2004 | Vatter et al. |
| 7,285,570 B2 | 10/2007 | Robinson et al. |
| 7,332,529 B2 | 2/2008 | Carr |
| 8,207,107 B2 * | 6/2012 | Fernandez Prieto et al. .. 510/501 |
| 8,236,748 B2 * | 8/2012 | Fernandez Prieto et al. .. 510/501 |
| 2002/0041889 A1 | 4/2002 | Masuda et al. |
| 2002/0131948 A1 | 9/2002 | Toumi et al. |
| 2002/0182237 A1 | 12/2002 | Bissett et al. |
| 2003/0108492 A1 | 6/2003 | Chaudhuri |
| 2003/0157035 A1 | 8/2003 | Chaudhuri |
| 2004/0057912 A1 | 3/2004 | Bonda |
| 2004/0057914 A1 | 3/2004 | Bonda |
| 2004/0057920 A1 | 3/2004 | Focht et al. |
| 2004/0062726 A1 | 4/2004 | Bonda et al. |
| 2004/0079916 A1 | 4/2004 | Brice et al. |
| 2004/0170586 A1 | 9/2004 | Ferrari et al. |
| 2004/0219119 A1 | 11/2004 | Wei et al. |
| 2006/0147396 A1 | 7/2006 | Monello |
| 2007/0020220 A1 | 1/2007 | Osborne |
| 2007/0039103 A1 | 2/2007 | Godfrey |
| 2007/0140993 A1 | 6/2007 | Evison |
| 2007/0297996 A1 | 12/2007 | Tanner |
| 2008/0019930 A1 | 1/2008 | Candau et al. |
| 2008/0145324 A1 | 6/2008 | Richard et al. |
| 2010/0112100 A1 | 5/2010 | Willemin et al. |
| 2010/0183529 A1 | 7/2010 | Richard et al. |
| 2010/0189669 A1 | 7/2010 | Hakozaki |

* cited by examiner

PERSONAL CARE COMPOSITIONS COMPRISING A PH TUNEABLE GELLANT AND METHODS OF USING

FIELD OF THE INVENTION

Personal care compositions are disclosed comprising a pH tuneable gellant that is compatible with a broad range of personal care ingredients.

BACKGROUND OF THE INVENTION

It has long been desired to create a broad range of personal care compositions tailored to the specific needs of consumers. For example, personal care compositions include anti-aging lotions, after-shave balms, hair styling products, mascaras, and the like. However, problems exist with developing "universal" compositions that can be tailored for particular products. Materials suitable for one composition may be unsuitable for another composition. This is particularly prevalent when attempting to structure personal care compositions. Structurants are typically selected based upon the particular phase being structured. Structurant selection may be limited if the composition includes reactive materials such as anionic species that can complex with cationic structurants. Structurant selection may be further limited given the pH of the personal care composition. Low or high pH can limit the efficacy of many structurants. Furthermore, skin feel is an important characteristic for personal care compositions. A sufficient amount of structurant is needed to achieve a consumer desirable and aesthetically pleasing viscosity. At efficacious levels, many structurants can result in an undesirable greasy or tacky skin feel. As a result, a challenge exits to find structurants compatible with a broad range of potential personal care compositions while providing consumer acceptable aesthetics.

SUMMARY OF THE INVENTION

Various personal care compositions are disclosed comprising a pH tuneable gellant. The pH tuneable gellant has a formula of:

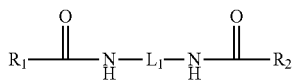
[I]

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group;

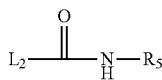
[II]

wherein $R_5$ is an aminofunctional moiety; $L_2$ is a backbone moiety having molecular weight from 14 to 500 g/mol; and at least one of $L_2$ or $R_5$ comprises a pH-sensitive group; and mixtures of [I] and [II].

The personal care composition may be a leave-on composition.

The personal care composition may be in the form of an emulsion comprising an aqueous phase, an oil phase, and a pH tuneable gellant as previously described.

A personal care composition may comprise a pH tuneable gellant, as previously described and an active or agent selected from a group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, particulate materials, UV actives, photostabilizers, anti-cellulite agents, desquamation actives, anti-acne actives, anti-oxidants, radical scavengers, conditioning agents, anti-inflammatory agents, tanning actives, skin lightening agents, botanical extracts, antimicrobial actives, antifungal actives, antibacterial actives, antiperspirant actives, sensates, preservatives, anti-dandruff actives, substantivity polymers, detersive surfactants, and combinations thereof.

DETAILED DESCRIPTION OF THE INVENTION

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity, unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "personal care composition" means compositions suitable for topical application on keratinous tissue.

The term "apply" or "application," as used in reference to a composition, means to apply or spread the compositions of the present invention onto keratinous tissue such as the epidermis.

The term "keratinous tissue" refers to keratin-containing layers disposed as the outermost protective covering of mammals (e.g., humans, dogs, cats, etc.) which includes, but is not limited to, skin, lips, hair, toenails, fingernails, cuticles, hooves, etc.

The term "dermatologically acceptable" means that the compositions or components described are suitable for use in contact with human skin tissue without undue toxicity, incompatibility, instability, allergic response, and the like.

The term "safe and effective amount" means an amount of a compound or composition sufficient to significantly induce a positive benefit.

The term "leave-on," in reference to compositions, means compositions intended to be applied to and allowed to remain on the keratinous tissue. These leave-on compositions are to be distinguished from compositions which are applied to the skin and subsequently (in a few minutes or less) removed either by washing, rinsing, wiping, or the like. Leave-on compositions exclude rinse-off applications such as shampoos, facial cleansers, hand cleansers, body wash, or body cleansers. The leave-on compositions may be substantially free of cleansing or detersive surfactants. For example, "leave-on compositions" may be left on the keratinous tissue for at least 15 minutes. For example, leave-on compositions may comprise less than 1% detersive surfactants, less than 0.5% detersive surfactants, or 0% detersive surfactants. The compositions may, however, contain emulsifying or other processing surfactants that are not intended to provide any significant cleansing benefits when applied topically to the skin.

The term "derivatives" means an ester, ether, amide, hydroxy, and/or salt structural analogue of the relevant compound.

The term "to structure" or "structure" means to increase viscosity, thicken, solidify, or provide solid or crystalline structure to the personal care composition The term "soluble" means at least about 0.1 g of solute dissolves in 100 ml of solvent, at 25° C. and 1 atm of pressure.

pH Tuneable Gellant

The personal care composition includes a pH tuneable gellant. The pH tuneable gellant may serve as a structurant in the personal care composition. The personal care composition may comprise from about 0.001%, 0.01%, 0.05%, 0.1%, 0.5%, 1%, 2.5%, 5%, 7.5%, or 10% to about 30%, 25%, 20%, 15%, 10%, 5%, 3%, 2%, 1%, or 0.5% of the pH tuneable gellant. The pH tuneable gellant may be used in an aqueous phase including water and/or water-equivalent solvent. The pH tuneable gellant may be used in an oil phase including oils described herein.

The pH tuneable amido gellant provides the personal care composition with a viscosity profile that is dependent on the pH of the composition. The pH tuneable amido gellants comprise at least one pH sensitive group. When a pH tuneable amido gellant is added to a polar protic solvent such as water, it is believed that the nonionic species form the viscosity building network while the ionic species are soluble and do not form a viscosity building network. By increasing or decreasing the pH (depending on the selection of the pH-sensitive groups) the amido gellant is either protonated or deprotonated. Thus, by changing the pH of the solution, the solubility and the viscosity building behaviour of the amido gellant can be controlled. By careful selection of the pH-sensitive groups, the pKa of the amido gellant can be tailored. Therefore, the choice of the pH-sensitive groups can be used to select the pH at which the amido gellant builds viscosity.

The pH tuneable amido gellant has a formula selected from the group consisting of:

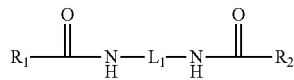

[I]

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group;

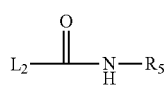

[II]

wherein $R_5$ is an aminofunctional moiety; $L_2$ is a backbone moiety having molecular weight from 14 to 500 g/mol; and at least one of $L_2$ or $R_5$ comprises a pH-sensitive group; and mixtures thereof; wherein the pH tuneable amido gellant has a pKa of from 1 to 30, or, alternately, a pKa of from 1.5 to 14.

Aminofunctional end-groups and aminofunctional moieties including amino and amido groups. Suitable aminofunctional end-groups and moities are exemplified in greater detail below.

The pH tuneable amido gellant comprises at least one amido functional group, and further comprises at least one pH-sensitive group. The pH tuneable amido gellant may have a molecular weight from about 150 g/mol, 300 g/mol, or 400 g/mol to about 1500 g/mol, 900 g/mol, or 700 g/mol.

In one embodiment, the pH tuneable amido gellant has the following structure [I]:

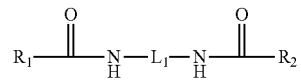

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group.

$L_1$ preferably has the formula:

$$L_1 = A_a\text{-}B_b\text{-}C_c\text{-}D_d,$$ [III]

wherein: (a+b+c+d) is from 1 to 20; and A, B, C and D are independently selected from the linking groups consisting of:

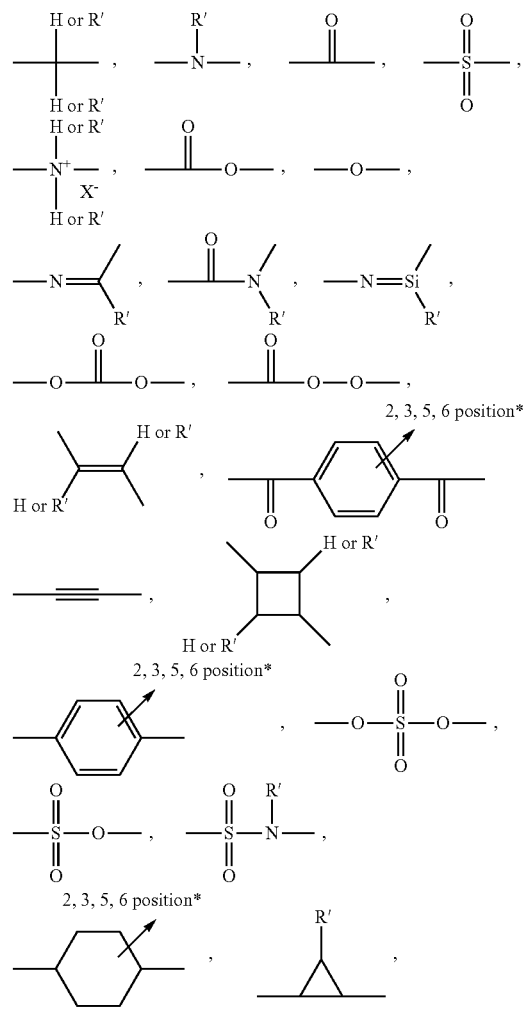

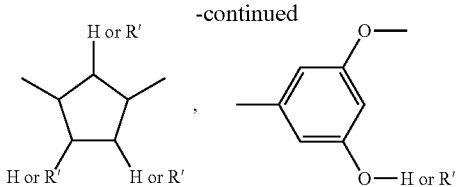

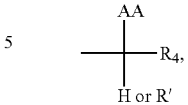

$R_2$ is $R_4$ or

Preferably, A, B, C and D are independently selected from the linking groups consisting of:

wherein each AA is independently selected from the group consisting of:

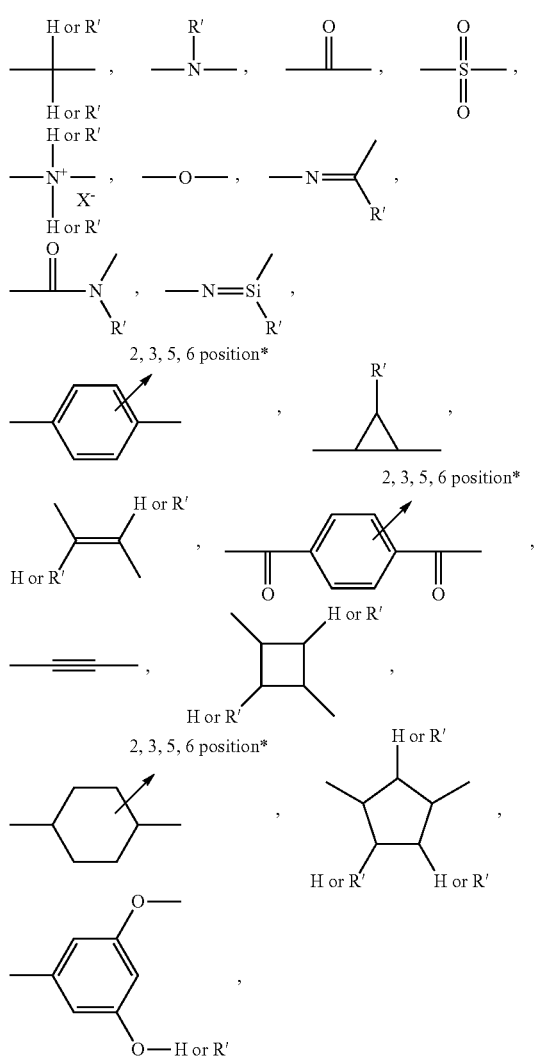

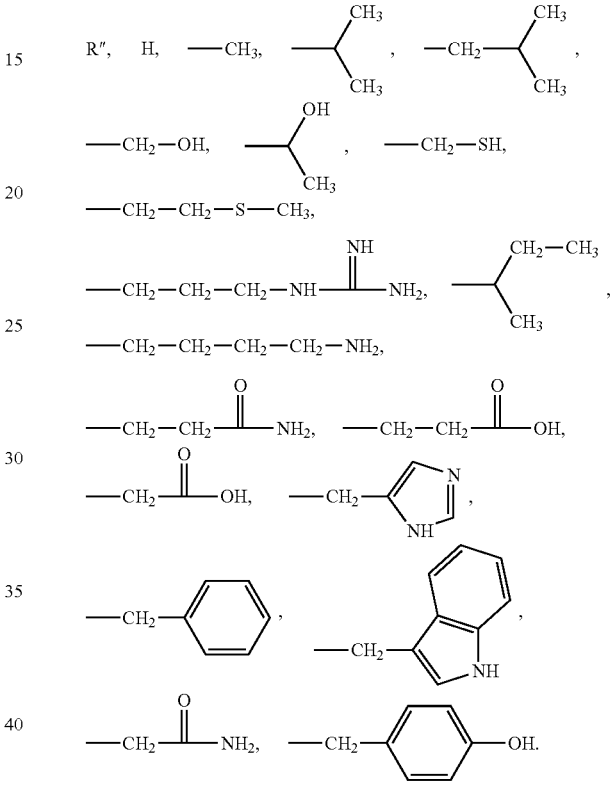

wherein the arrow indicates up to 4 substitutions in the positions indicated, and $X^-$ an anion. In certain embodiments, $L_1$ is selected from C2 to C20, C6 to C12, or C8 to C10 hydrocarbyl chains.

In certain embodiments $R_1$ is $R_3$ or

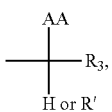

and $R_3$ and $R_4$ independently have the formula:

$$(L')_o\text{-}(L'')_q\text{-}R, \qquad [IV]$$

wherein: (o+q) is from 1 to 10; L' and L" are linking groups, independently selected from the same groups as A, B, C and D in equation [III]; and R, R' and R" are independently selected either from the pH-sensitive-groups consisting of:

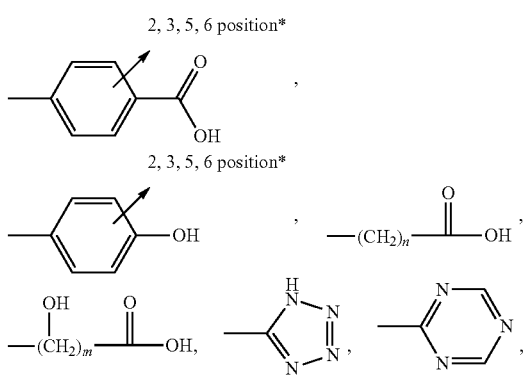

-continued

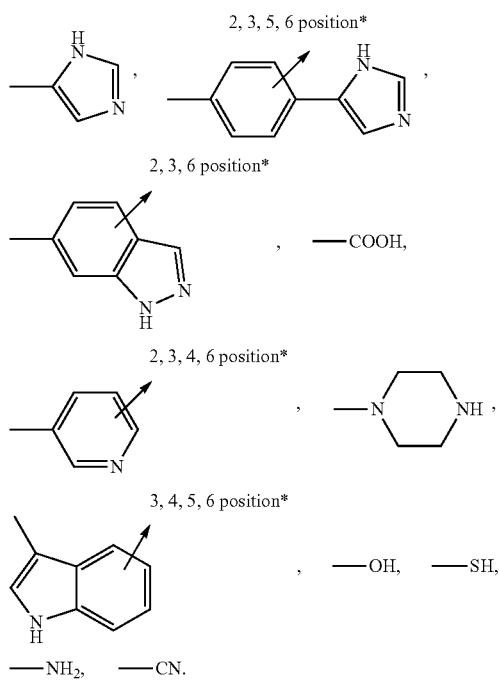

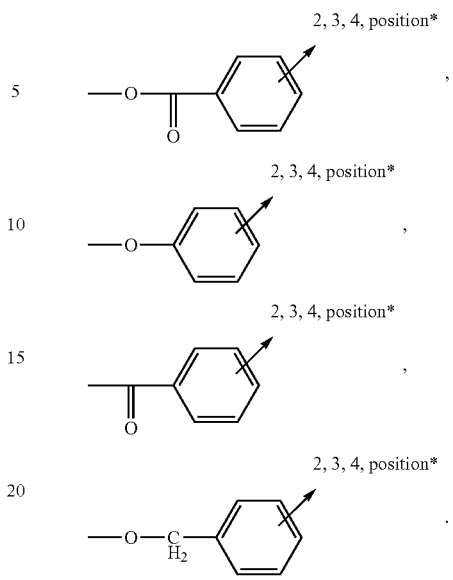

wherein the arrow indicates up to 4 substitutions in the positions indicated, n and m are integers from 1 to 20 or from the non-pH-sensitive groups consisting of:

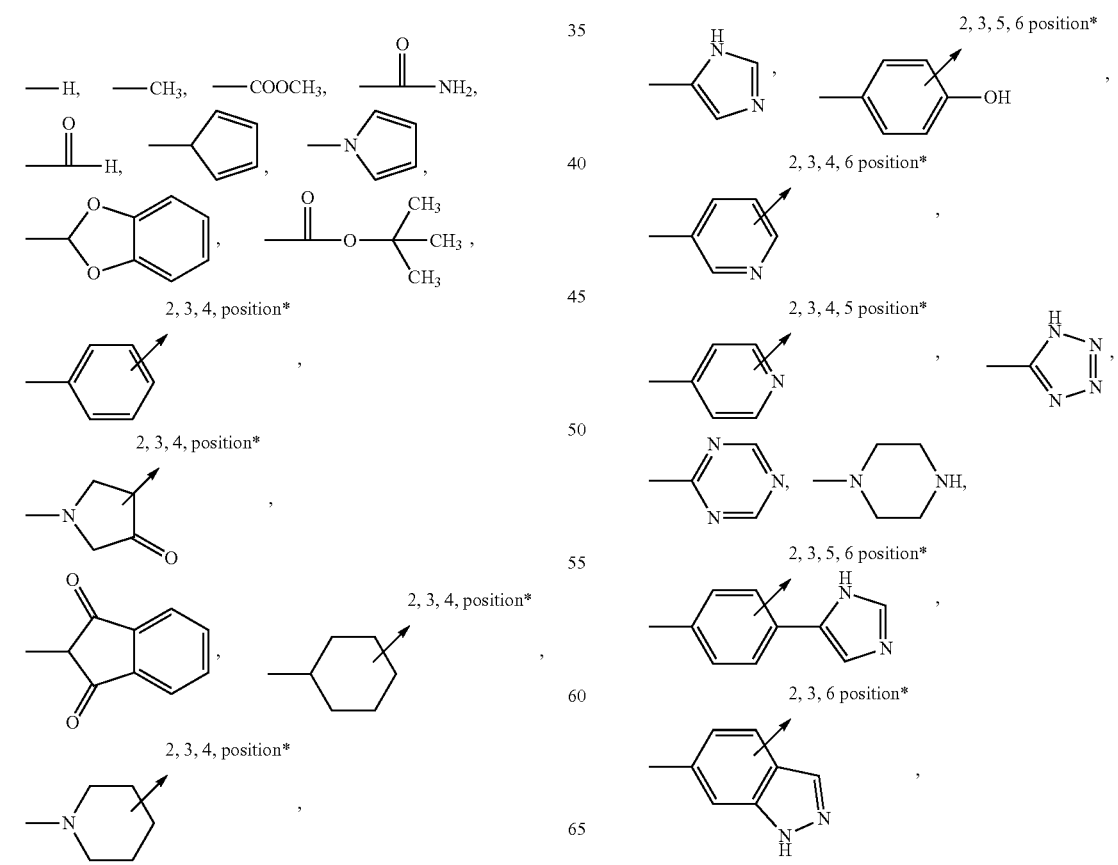

such that at least one of R, R' and R" comprises a pH-sensitive group. Preferably, R comprises the pH-sensitive group.

In other embodiments, at least some of R, R' and R" are independently selected from the group of pH-sensitive groups consisting of:

-continued

—OH, —NH₂, 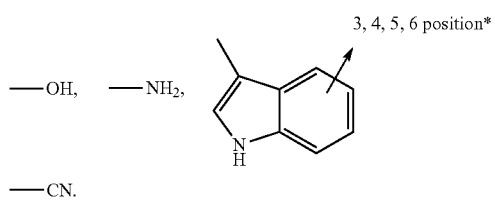,

—CN.

In certain embodiments, the pH tuneable amido gellant having structure [I] is characterized in that: $L_1$ is an aliphatic linking group with a backbone chain of from 2 to 20 carbon atoms [such as —(CH₂)ₙ— wherein n is selected from 2 to 20], and both $R_1$ and $R_2$ have the structure:

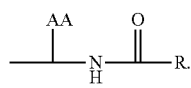

AA is preferably selected from the group consisting of:

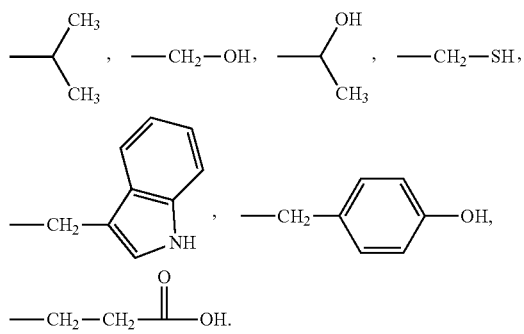

or from the group consisting of:

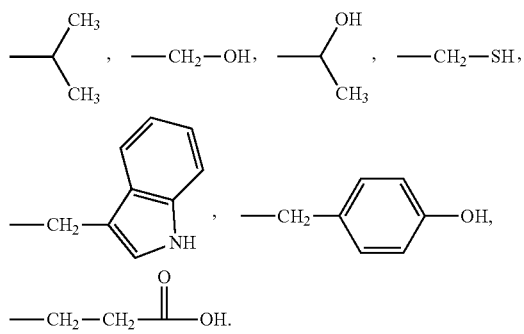

and R is preferably selected from the pH-sensitive groups consisting of:

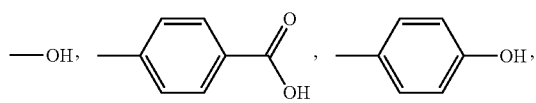

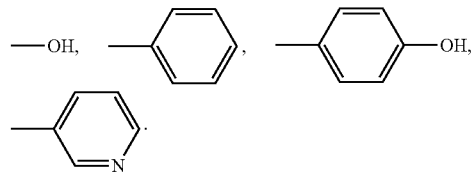

or from the group:

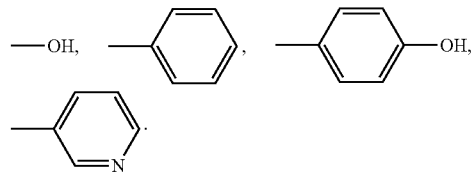

In another embodiment, two or more of $L_1$, L' and L" are the same group.

The pH tuneable amido gellant molecule described in formula [I] can be symmetric with respect to the $L_1$ entity or can be asymmetric. Without intending to be bound by theory, it is believed that symmetric pH tuneable amido gellant molecules allow for more orderly structured networks to form, whereas compositions comprising one or more asymmetric pH tuneable amido gellant molecules may create disordered networks.

In another embodiment, the pH tuneable amido gellant has the structure [II]:

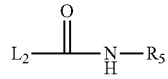

wherein $R_5$ is an aminofunctional moiety; $L_2$ is a backbone moiety having molecular weight from 14 to 500 g/mol; and at least one of $L_2$ or $R_5$ comprises a pH-sensitive group;

$L_2$ may have the formula:

$$L_2 = A_a\text{-}B_b\text{-}C_c\text{-}D_d\text{-}R''', \quad [V]$$

wherein: (a+b+c+d) is from 1 to 20; and R''' is either a pH-sensitive group or a non-pH-sensitive groups (selected from the same groups as R, R' and R" for structure [I]). $L_2$ may be selected from C2 to C20, C6 to C12, or C8 to C10 hydrocarbyl chains.

$R_5$ may have the formula:

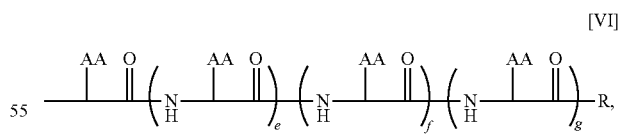

[VI]

wherein: AA is independently selected from the same group of AA as for structure [I]; (e+f+g) is from 0 to 20 or from 1 to 3.

At least one of AA, R or R''' comprises a pH sensitive group. Preferably, R comprises the pH sensitive group.

In a certain embodiments, the pH tuneable amido gellant having structure [II] is characterized in that: $L_2$ is an aliphatic linking group with a backbone chain of from 2 to 20 carbon atoms, preferably —(CH₂)ₙ—CH₃ wherein n is selected from 2 to 20, and $R_5$ has the structure:

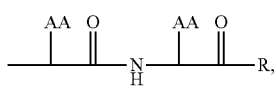

wherein each AA is independently selected from the group consisting of:

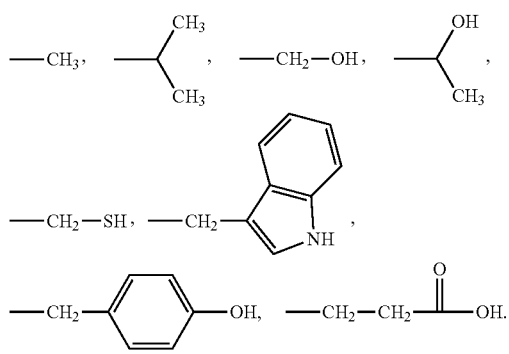

or from the group consisting of:

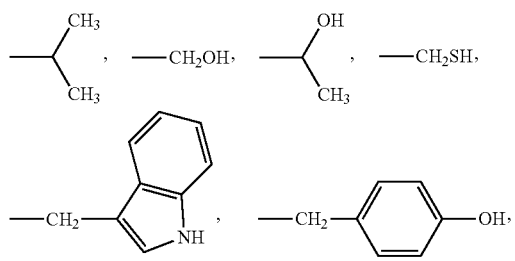

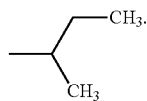

and R is selected from the pH-sensitive groups consisting of:

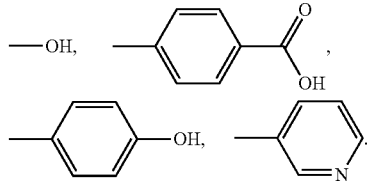

or from the group:

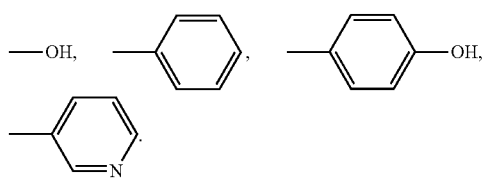

Suitable pH tuneable amido gellants may be selected from Tables 1-3 as provided below.

TABLE 1

Non-limiting examples of pH tuneable amido gellants having structure [I] for use in a personal care composition N,N'-(2S,2'S)-1,1'-(ethane-1,2-diylbis(azanediyl))bis(3-methyl-1-oxobutane-2,1-diyl)diisonicotinamide

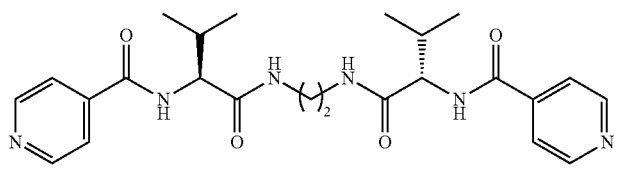

N,N'-(2S,2'S)-1,1'-(propane-1,3-diylbis(azanediyl))bis(3-methyl-1-oxobutane-2,1-diyl)diisonicotinamide

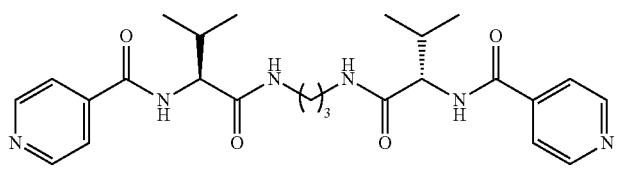

TABLE 1-continued

Non-limiting examples of pH tuneable amido gellants having structure [I] for use in a personal care composition N,N'-(2S,2'S)-1,1'-(butane-1,4-diylbis(azanediyl))bis(3-methyl-1-oxobutane-2,1-diyl)diisonicotinamide

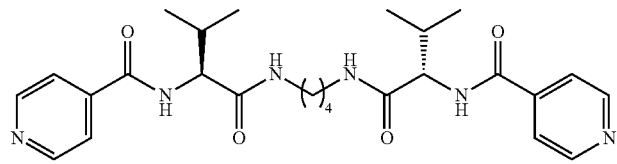

N,N'-(2S,2'S)-1,1'-(pentane-1,5-diylbis(azanediyl))bis(3-methyl-1-oxobutane-2,1-diyl)diisonicotinamide

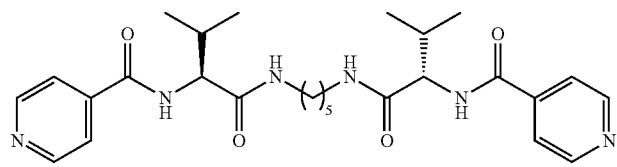

N,N'-(2S,2'S)-1,1'-(hexane-1,6-diylbis(azanediyl))bis(3-methyl-1-oxobutane-2,1-diyl)diisonicotinamide

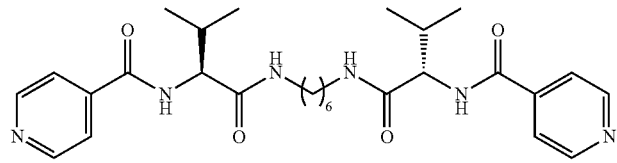

N,N'-(2S,2'S)-1,1'-(heptane-1,7-diylbis(azanediyl))bis(3-methyl-1-oxobutane-2,1-diyl)diisonicotinamide

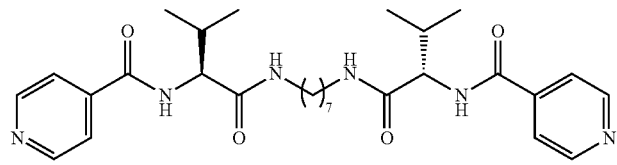

N,N'-(2S,2'S)-1,1'-(octane-1,8-diylbis(azanediyl))bis(3-methyl-1-oxobutane-2,1-diyl)diisonicotinamide

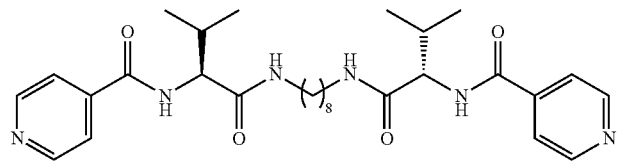

(6S,13S)-6,13-diisopropyl-4,7,12,15-tetraoxo-5,8,11,14-tetraazaoctadecane-1,18-dioic acid

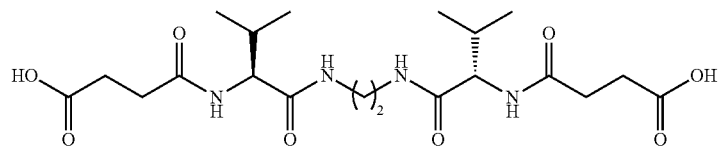

TABLE 1-continued

Non-limiting examples of pH tuneable amido gellants having structure [I] for use in a personal care composition (6S,14S')-6,14-diisopropyl-4,7,13,16-tetraoxo-5,8,12,15-tetraazanonadecane-1,19-dioic acid

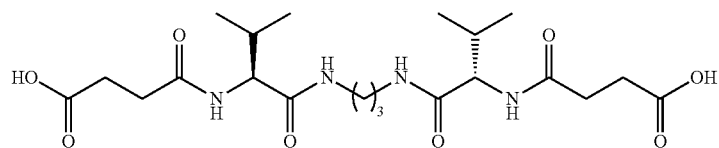

(6S,15S)-6,15-diisopropyl-4,7,14,17-tetraoxo-5,8,13,16-tetraazaeicosane-1,20-dioic acid

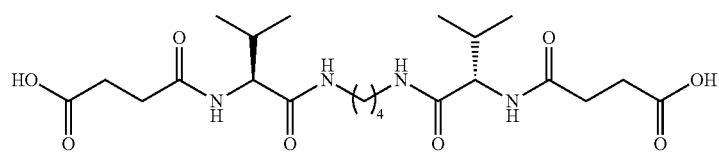

(6S,16S)-6,16-diisopropyl-4,7,15,18-tetraoxo-5,8,14,17-tetraazaheneicosane-1,21-dioic acid

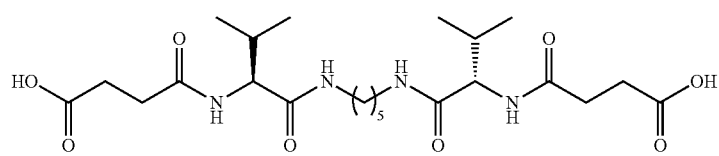

(6S,17S)-6,17-diisopropyl-4,7,16,19-tetraoxo-5,8,15,18-tetraazadocosane-1,22-dioic acid

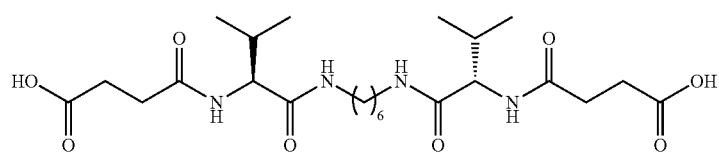

(6S,18S)-6,18-diisopropyl-4,7,17,20-tetraoxo-5,8,16,19-tetraazatricosane-1,23-dioic acid

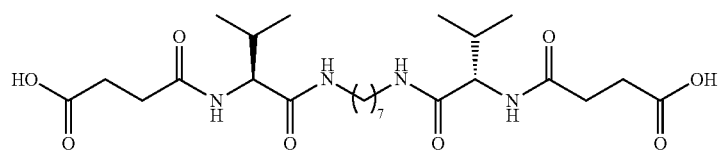

(6S,19S)-6,19-diisopropyl-4,7,18,21-tetraoxo-5,8,17,20-tetraazatetracosane-1,24-dioic acid

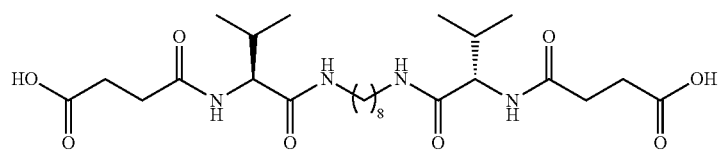

(6S,20S)-6,20-diisopropyl-4,7,19,22-tetraoxo-5,8,18,21-tetraazapentacosane-1,25-dioic acid

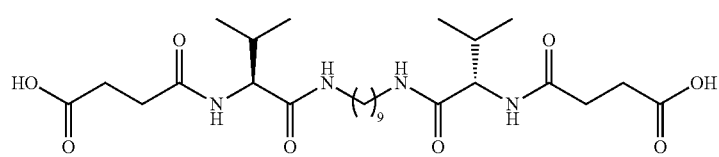

TABLE 1-continued

Non-limiting examples of pH tuneable amido gellants having structure [I] for use in a personal care composition (6S,21S)-6,21-diisopropyl-4,7,20,23-tetraoxo-5,8,19,22-tetraazahexacosane-1,26-dioic acid

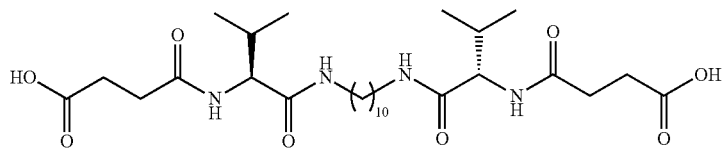

(6S,22S)-6,22-diisopropyl-4,7,21,24-tetraoxo-5,8,20,23-tetraazaheptacosane-1,27-dioic acid

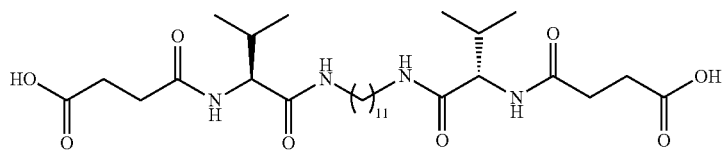

(6S,23S)-6,23-diisopropyl-4,7,22,25-tetraoxo-5,8,21,24-tetraazaoctacosane-1,28-dioic acid

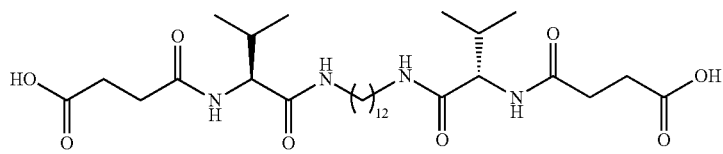

N,N'-(2S,2'S)-1,1'-(ethane-1,2-diylbis(azanediyl))bis(3-methyl-1-oxobutane-2,1-diyl)bis(4-(1H-imidazol-5-yl)benzamide)

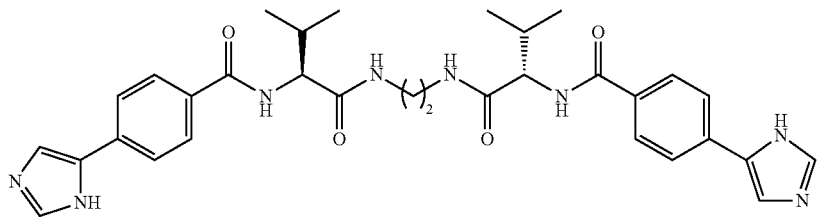

N,N'-(2S,2'S)-1,1'-(propane-1,3-diylbis(azanediyl))bis(3-methyl-1-oxobutane-2,1-diyl)bis(4-(1H-imidazol-5-yl)benzamide)

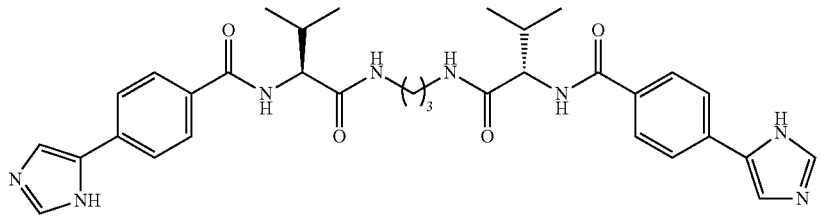

N,N'-(2S,2'S)-1,1'-(butane-1,4-diylbis(azanediyl))bis(3-methyl-1-oxobutane-2,1-diyl)bis(4-(1H-imidazol-5-yl)benzamide)

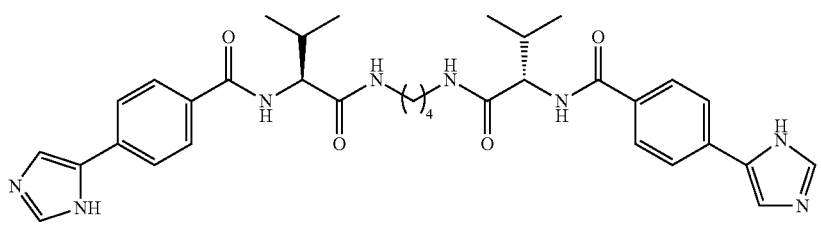

TABLE 1-continued

Non-limiting examples of pH tuneable amido gellants having structure [I] for use in a personal care composition N,N'-(2S,2'S)-1,1'-(pentane-1,5-diylbis(azanediyl))bis(3-methyl-1-oxobutane-2,1-diyl)bis(4-(1H-imidazol-5-yl)benzamide)

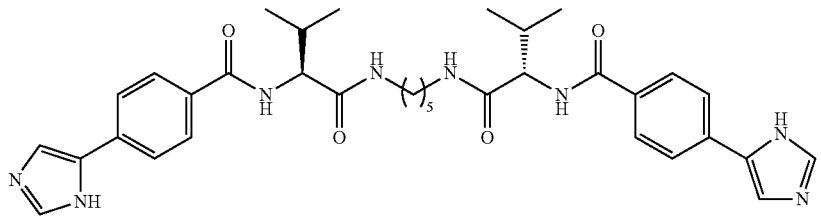

N,N'-(2S,2'S)-1,1'-(hexane-1,6-diylbis(azanediyl))bis(3-methyl-1-oxobutane-2,1-diyl)bis(4-(1H-imidazol-5-yl)benzamide)

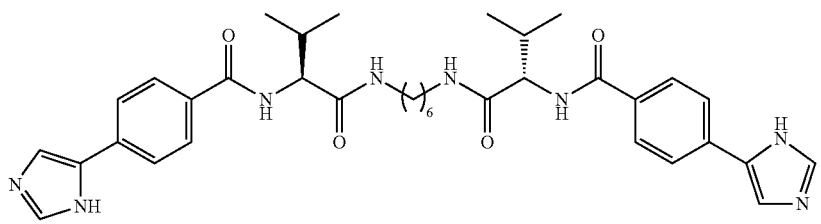

N,N'-(2S,2'S)-1,1'-(heptane-1,7-diylbis(azanediyl))bis(3-methyl-1-oxobutane-2,1-diyl)bis(4-(1H-imidazol-5-yl)benzamide)

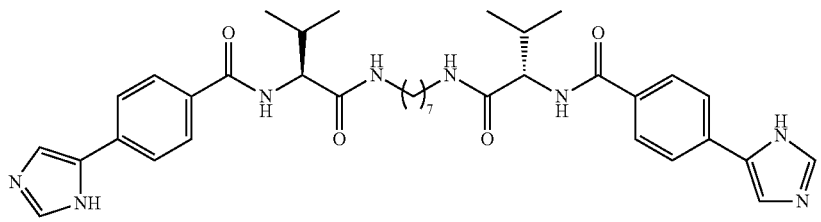

N,N'-(2S,2'S)-1,1'-(octane-1,8-diylbis(azanediyl))bis(3-methyl-1-oxobutane-2,1-diyl)bis(4-(1H-imidazol-5-yl)benzamide)

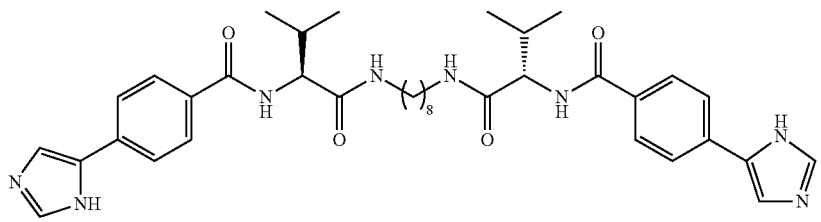

N,N'-(2S,2'S)-1,1'-(nonane-1,9-diylbis(azanediyl))bis(3-methyl-1-oxobutane-2,1-diyl)bis(4-(1H-imidazol-5-yl)benzamide)

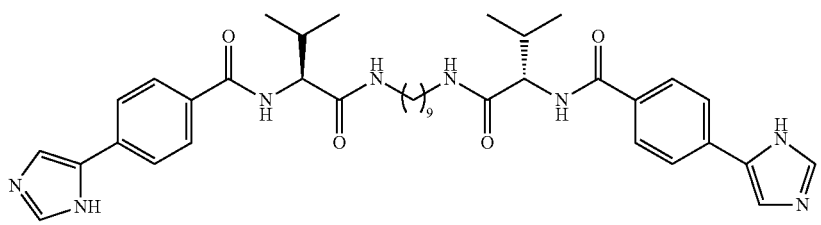

TABLE 1-continued

Non-limiting examples of pH tuneable amido gellants having structure [I] for use in a personal care composition N,N'-(2S,2'S)-1,1'-(decane-1,10-diylbis(azanediyl))bis(3-methyl-1-oxobutane-2,1-diyl)bis(4-(1H-imidazol-5-yl)benzamide)

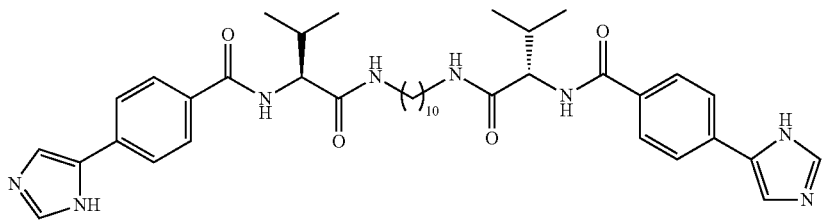

N,N'-(2S,2'S)-1,1'-(undecane-1,11-diylbis(azanediyl))bis(3-methyl-1-oxobutane-2,1-diyl)bis(4-(1H-imidazol-5-yl)benzamide)

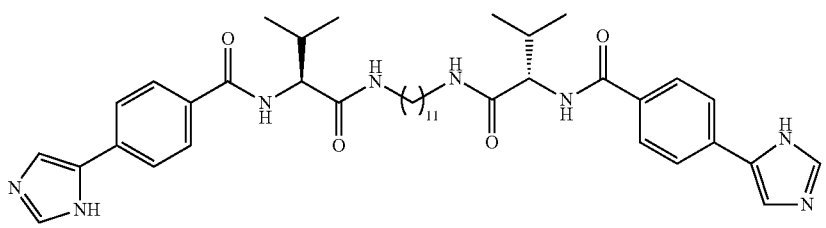

N,N'-(2S,2'S)-1,1'-(dodecane-1,12-diylbis(azanediyl))bis(3-methyl-1-oxobutane-2,1-diyl)bis(4-(1H-imidazol-5-yl)benzamide)

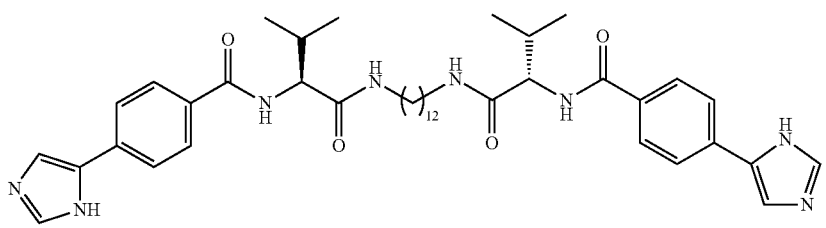

TABLE 2

Non-limiting examples of pH tuneable amido gellants having structure [I] for use in a personal care composition N,N'-(2S,2'S)-1,1'-(nonane-1,9-diylbis(azanediyl))bis(3-methyl-1-oxobutane-2,1-diyl)diisonicotinamide

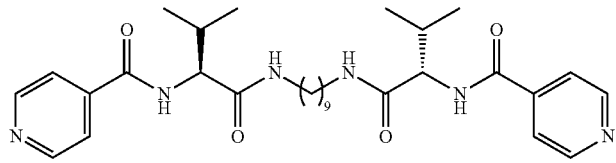

N,N'-(2S,2'S)-1,1'-(decane-1,10-diylbis(azanediyl))bis(3-methyl-1-oxobutane-2,1-diyl)diisonicotinamide

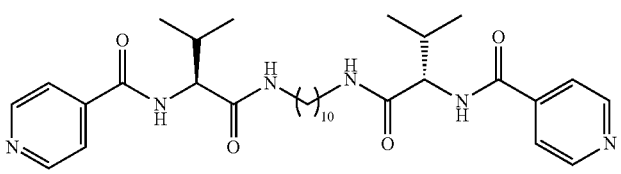

TABLE 2-continued

Non-limiting examples of pH tuneable amido gellants having structure [I] for use in a personal care composition N,N'-(2S,2'S)-1,1'-(undecane-1,11-diylbis(azanediyl))bis(3-methyl-1-oxobutane-2,1-diyl)diisonicotinamide

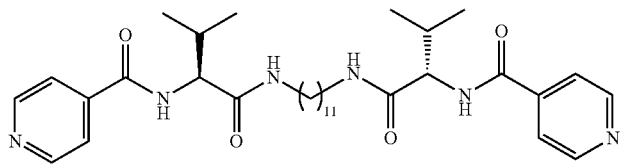

N,N'-(2S,2'S)-1,1'-(dodecane-1,12-diylbis(azanediyl))bis(3-methyl-1-oxobutane-2,1-diyl)diisonicotinamide

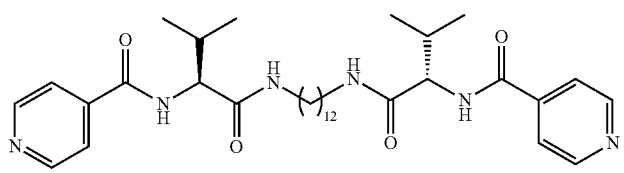

N,N'-(2S,2'S)-1,1'-(tridecane-1,13-diylbis(azanediyl))bis(3-methyl-1-oxobutane-2,1-diyl)diisonicotinamide

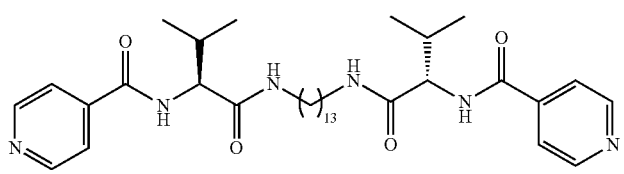

N,N'-(2S,2'S)-1,1'-(tetradecane-1,14-diylbis(azanediyl)))bis(3-methyl-1-oxobutane-2,1-diyl)diisonicotinamide

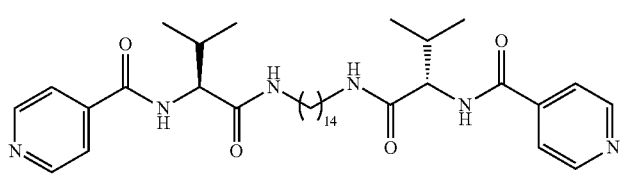

N,N'-(2S,2'S)-1,1'-(hexadecane-1,16-diylbis(azanediyl))bis(3-methyl-1-oxobutane-2,1-diyl)diisonicotinamide

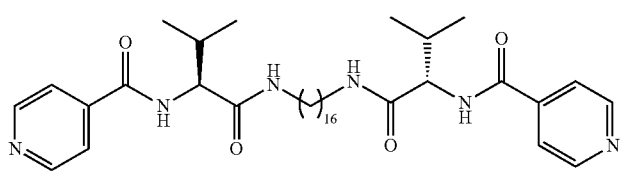

N,N'-(2S,2'S)-1,1'-(octadecane-1,18-diylbis(azanediyl))bis(3-methyl-1-oxobutane-2,1-diyl)diisonicotinamide

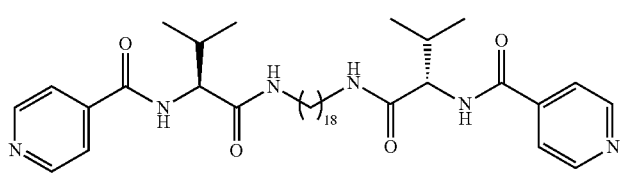

TABLE 2-continued

Non-limiting examples of pH tuneable amido gellants having structure [I] for use in a personal care composition N,N'-(2S,2'S)-1,1'-(ethane-1,2-diylbis(azanediyl))bis(1-oxopropane-2,1-diyl)diisonicotinamide

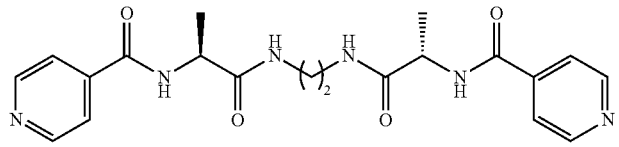

N,N'-(2S,2'S)-1,1'-(propane-1,3-diylbis(azanediyl))bis(1-oxopropane-2,1-diyl)diisonicotinamide

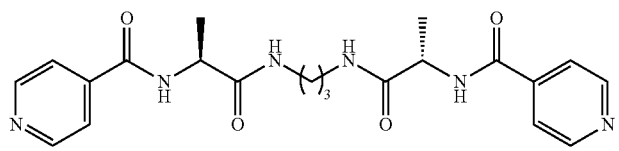

N,N'-(2S,2'S)-1,1'-(butane-1,4-diylbis(azanediyl))bis(1-oxopropane-2,1-diyl)diisonicotinamide

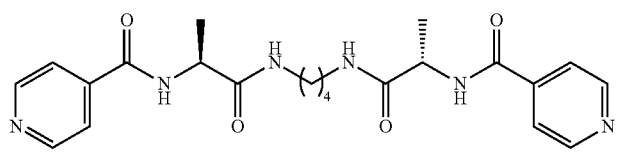

N,N'-(2S,2'S)-1,1'-(pentane-1,5-diylbis(azanediyl))bis(1-oxopropane-2,1-diyl)diisonicotinamide

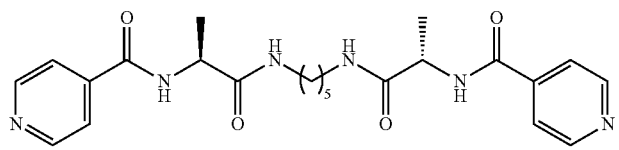

N,N'-(2S,2'S)-1,1'-(hexane-1,6-diylbis(azanediyl))bis(1-oxopropane-2,1-diyl)diisonicotinamide

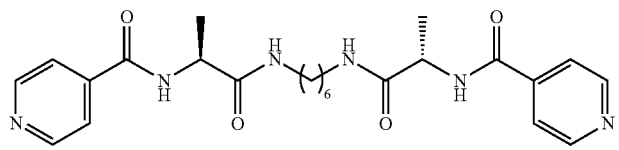

N,N'-(2S,2'S)-1,1'-(heptane-1,7-diylbis(azanediyl))bis(1-oxopropane-2,1-diyl)diisonicotinamide

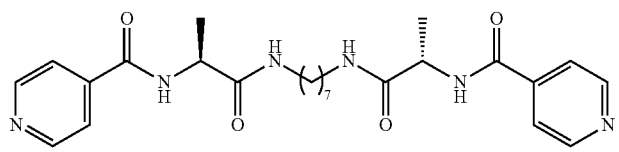

N,N'-(2S,2'S)-1,1'-(octane-1,8-diylbis(azanediyl))bis(1-oxopropane-2,1-diyl)diisonicotinamide

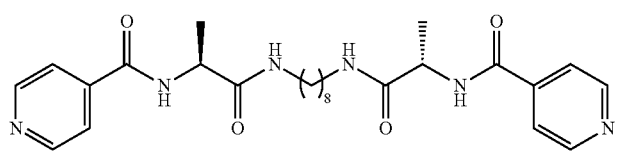

TABLE 2-continued

Non-limiting examples of pH tuneable amido gellants having structure [I] for use in a personal care composition N,N'-(2S,2'S)-1,1'-(nonane-1,9-diylbis(azanediyl))bis(1-oxopropane-2,1-diyl)diisonicotinamide

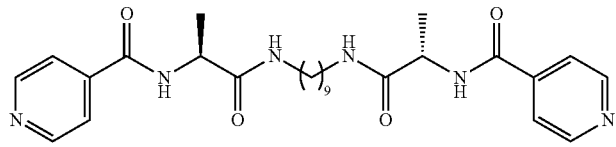

N,N'-(2S,2'S)-1,1'-(decane-1,10-diylbis(azanediyl))bis(1-oxopropane-2,1-diyl)diisonicotinamide

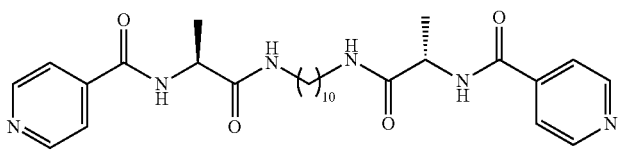

N,N'-(2S,2'S)-1,1'-(undecane-1,11-diylbis(azanediyl))bis(1-oxopropane-2,1-diyl)diisonicotinamide

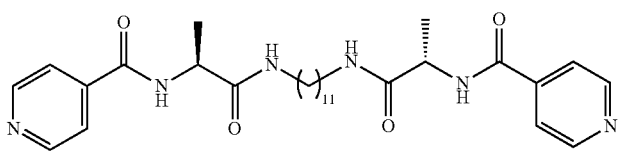

N,N'-(2S,2'S)-1,1'-(dodecane-1,12-diylbis(azanediyl))bis(1-oxopropane-2,1-diyl)diisonicotinamide

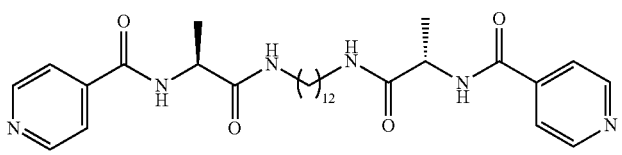

N,N'-(2S,2'S)-1,1'-(tridecane-1,13-diylbis(azanediyl))bis(1-oxopropane-2,1-diyl)diisonicotinamide

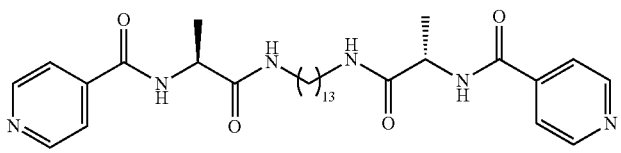

N,N'-(2S,2'S)-1,1'-(tetradecane-1,14-diylbis(azanediyl))bis(1-oxopropane-2,1-diyl)diisonicotinamide

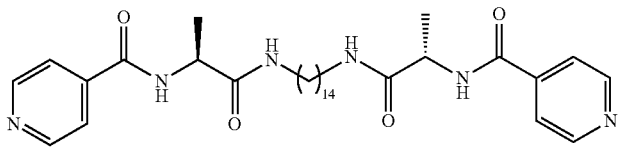

N,N'-(2S,2'S)-1,1'-(hexadecane-1,16-diylbis(azanediyl))bis(1-oxopropane-2,1-diyl)diisonicotinamide

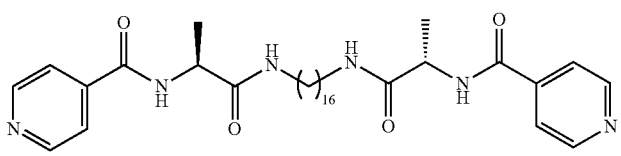

TABLE 2-continued

Non-limiting examples of pH tuneable amido gellants having structure [I] for use in a personal care composition N,N'-(2S,2'S)-1,1'-(octadecane-1,18-diylbis(azanediyl))bis(1-oxopropane-2,1-diyl)diisonicotinamide

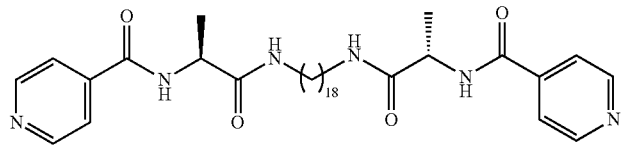

N,N'-(2S,2'S)-1,1'-(ethane-1,2-diylbis(azanediyl))bis(1-oxo-3-phenylpropane-2,1-diyl)diisonicotinamide

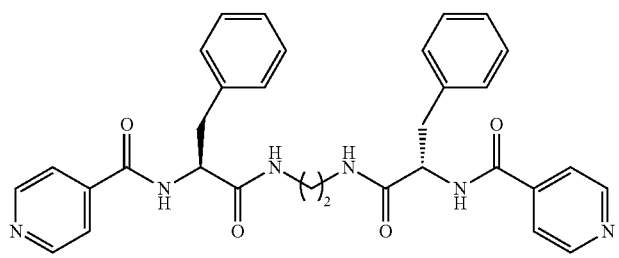

N,N'-(2S,2'S)-1,1'-(propane-1,3-diylbis(azanediyl))bis(1-oxo-3-phenylpropane-2,1-diyl)diisonicotinamide

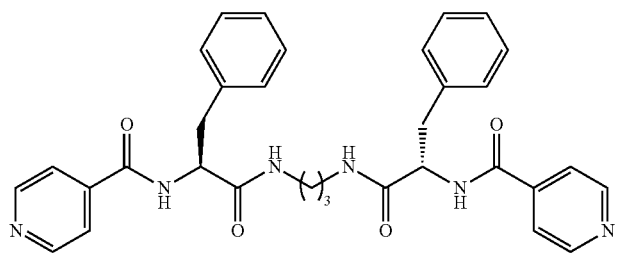

N,N'-(2S,2'S)-1,1'-(butane-1,4-diylbis(azanediyl))bis(1-oxo-3-phenylpropane-2,1-diyl)diisonicotinamide

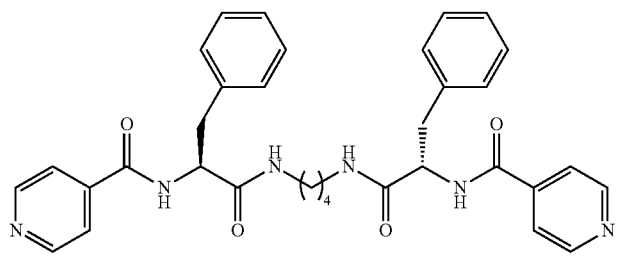

N,N'-(2S,2'S)-1,1'-(pentane-1,5-diylbis(azanediyl))bis(1-oxo-3-phenylpropane-2,1-diyl)diisonicotinamide

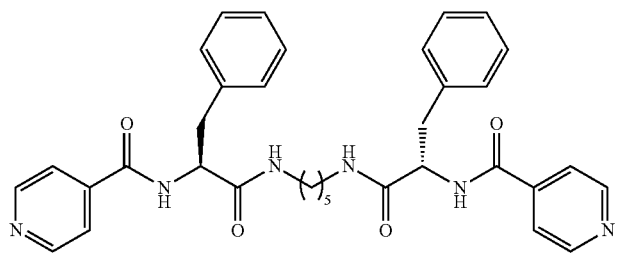

TABLE 2-continued

Non-limiting examples of pH tuneable amido gellants having structure [I] for use in a personal care composition N,N'-(2S,2'S)-1,1'-(hexane-1,6-diylbis(azanediyl))bis(1-oxo-3-phenylpropane-2,1-diyl)diisonicotinamide

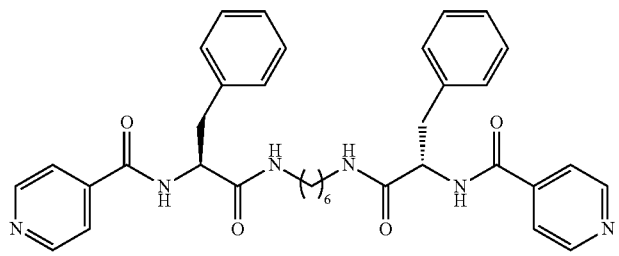

N,N'-(2S,2'S)-1,1'-(heptane-1,7-diylbis(azanediyl))bis(1-oxo-3-phenylpropane-2,1-diyl)diisonicotinamide

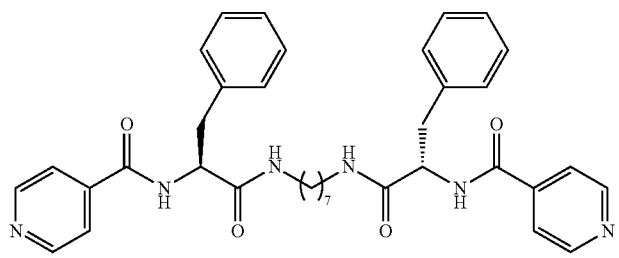

N,N'-(2S,2'S)-1,1'-(octane-1,8-diylbis(azanediyl))bis(1-oxo-3-phenylpropane-2,1-diyl)diisonicotinamide

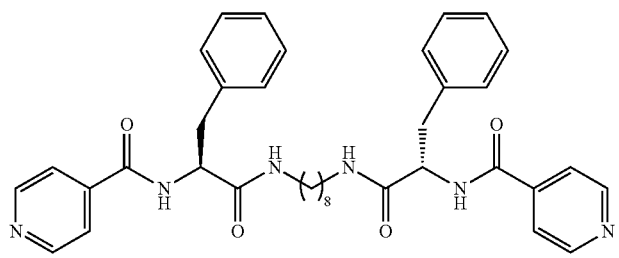

N,N'-(2S,2'S)-1,1'-(nonane-1,9-diylbis(azanediyl))bis(1-oxo-3-phenylpropane-2,1-diyl)diisonicotinamide

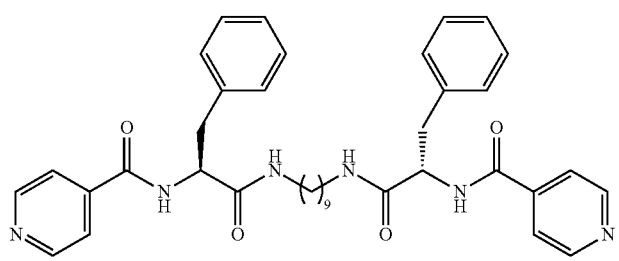

TABLE 2-continued

Non-limiting examples of pH tuneable amido gellants having structure [I] for use in a personal care composition N,N'-(2S,2'S)-1,1'-(decane-1,10-diylbis(azanediyl))bis(1-oxo-3-phenylpropane-2,1-diyl)diisonicotinamide

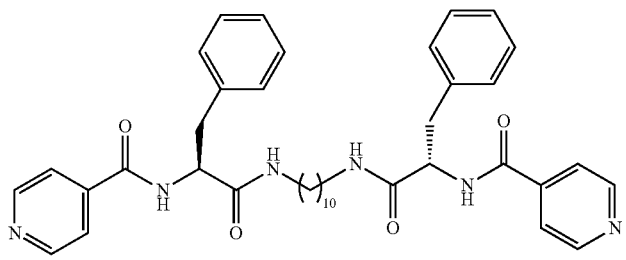

N,N'-(2S,2'S)-1,1'-(undecane-1,11-diylbis(azanediyl))bis(1-oxo-3-phenylpropane-2,1-diyl)diisonicotinamide

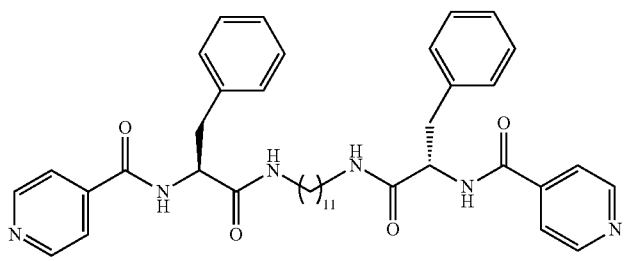

N,N'-(2S,2'S)-1,1'-(dodecane-1,12-diylbis(azanediyl))bis(1-oxo-3-phenylpropane-2,1-diyl)diisonicotinamide

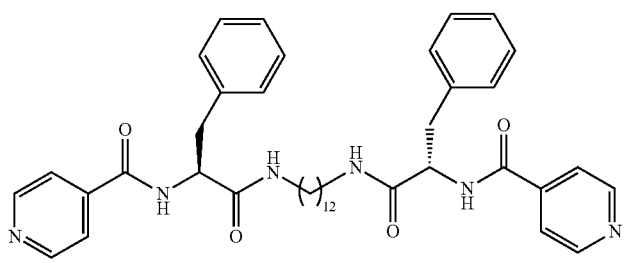

N,N'-(2S,2'S)-1,1'-(tridecane-1,13-diylbis(azanediyl))bis(1-oxo-3-phenylpropane-2,1-diyl)diisonicotinamide

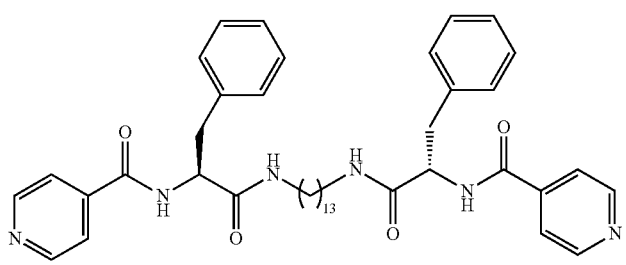

TABLE 2-continued

Non-limiting examples of pH tuneable amido gellants having structure [I] for use in a personal care composition N,N'-(2S,2'S)-1,1'-(tetradecane-1,14-diylbis(azanediyl))bis(1-oxo-3-phenylpropane-2,1-diyl)diisonicotinamide

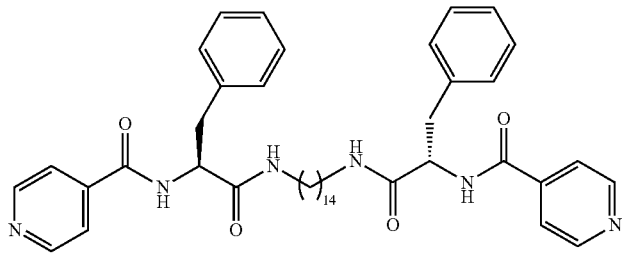

N,N'-(2S,2'S)-1,1'-(hexadecane-1,16-diylbis(azanediyl))bis(1-oxo-3-phenylpropane-2,1-diyl)diisonicotinamide

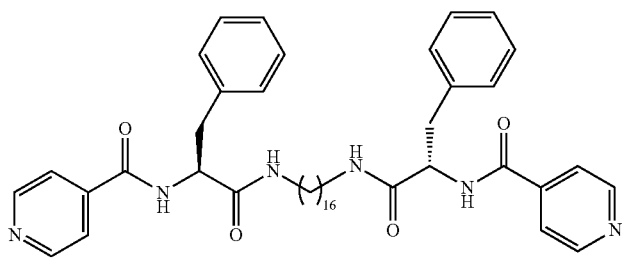

N,N'-(2S,2'S)-1,1'-(octadecane-1,18-diylbis(azanediyl))bis(1-oxo-3-phenylpropane-2,1-diyl)diisonicotinamide

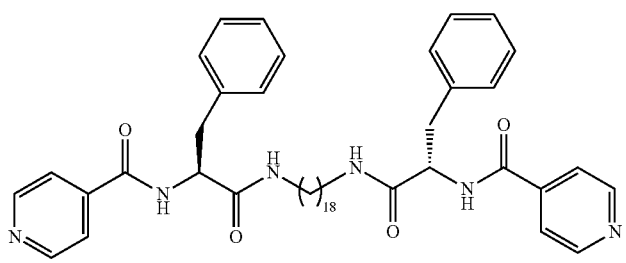

TABLE 3

Non-limiting examples of pH tuneable amido gellants having structure [II] for use in a personal care composition (2S)-2-[[2-(dodecanoylamino)acetyl]amino]propanoic acid

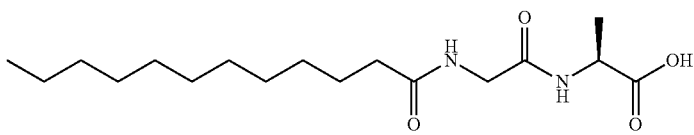 [SMILES: CCCCCCCCCCCC(=O)NCC(=O)N[C@@H](C)C(=O)O]

(2S)-2-[[2-[[2-(dodecanoylamino)acetyl]amino]acetyl]amino]propanoic acid

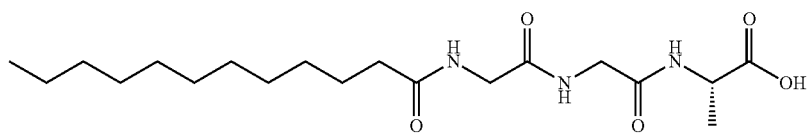 [SMILES: CCCCCCCCCCCC(=O)NCC(=O)NCC(=O)N[C@@H](C)C(=O)O]

TABLE 3-continued

Non-limiting examples of pH tuneable amido gellants having structure [II] for use in a personal care composition (2S)-2-[[2-(dodecanoylamino)acetyl]amino]-2-phenyl acetic acid

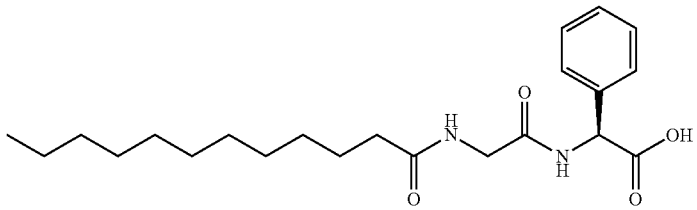 [SMILES: CCCCCCCCCCCC(=O)NCC(=O)N[C@H](C(=O)O)c1ccccc1]

(2S)-2-[[2-(dodecanoylamino)acetyl]amino]-3-methyl-butanoic acid

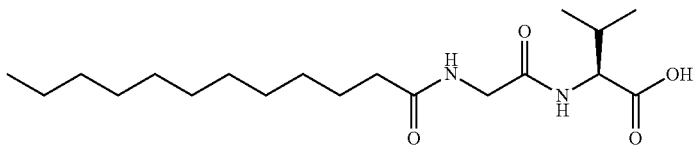 [SMILES: CCCCCCCCCCCC(=O)NCC(=O)N[C@H](C(=O)O)C(C)C]

(2S)-2-[[2-(dodecanoylamino)acetyl]amino]acetic acid

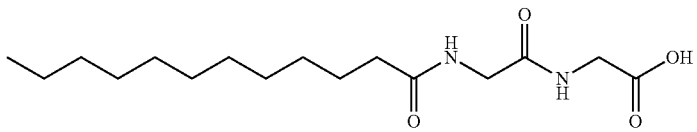 [SMILES: CCCCCCCCCCCC(=O)NCC(=O)NCC(=O)O]

(2S)-2-[[2-(hexadecanoylamino)acetyl]amino]propanoic acid

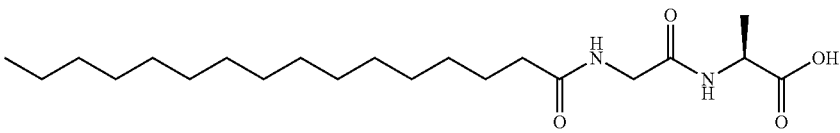 [SMILES: CCCCCCCCCCCCCCCC(=O)NCC(=O)N[C@@H](C)C(=O)O]

From the examples provided in Tables 1-3, pH tuneable amido gellants having a terminal pyridine group (e.g., diisonicotinamide structures) may be particularly suitable for gelling neutral to basic systems (i.e., pH of greater than about 6). pH tuneable amido gellants having a terminal carboxylic acid group (e.g., dioic acid structures) may be particularly suitable for gelling acid systems (i.e., pH of less than about 5). pH tuneable amido gellants having a terminal imidazole group (e.g., (4-(1H-imidazol-5-yl)benzamide) structures) may be particularly suitable for gelling neutral to basic systems (i.e., pH of greater than about 6).

In certain embodiments of both types of pH tuneable amido gellant structures, AA comprises at least one of: Alanine, β-Alanine and substituted Alanines; Linear Amino-Alkyl Carboxylic Acid; Cyclic Amino-Alkyl Carboxylic Acid; Aminobenzoic Acid Derivatives; Aminobutyric Acid Derivatives; Arginine and Homologues; Asparagine; Aspartic Acid; p-Benzoyl-Phenylalanine; Biphenylalanine; Citrulline; Cyclopropylalanine; Cyclopentylalanine; Cyclohexylalanine; Cysteine, Cystine and Derivatives; Diaminobutyric Acid Derivatives; Diaminopropionic Acid; Glutamic Acid Derivatives; Glutamine; Glycine; Substituted Glycines; Histidine; Homoserine; Indole Derivatives; Isoleucine; Leucine and Derivatives; Lysine; Methionine; Naphthylalanine; Norleucine; Norvaline; Ornithine; Phenylalanine; Ring-Substituted Phenylalanines; Phenylglycine; Pipecolic Acid, Nipecotic Acid and Isonipecotic Acid; Proline; Hydroxyproline; Thiazolidine; Pyridylalanine; Serine; Statine and Analogues; Threonine; Tetrahydronorharman-3-carboxylic Acid; 1,2,3,4-Tetrahydroisoquinoline; Tryptophane; Tyrosine; Valine; and combinations thereof.

The pH tuneable amido gellant molecule may also comprise protective groups, preferably from 1 to 2 protective groups, preferably two protective groups. Examples of suitable protective groups are provided in "Protecting Groups", P. J. Kocienski, ISBN 313 135601 4, Georg Thieme Verlag, Stutgart; and "Protective Groups in Organic Chemistry", T. W. Greene, P. G. M. Wuts, ISBN 0-471-62301-6, John Wiley & Sons, Inc, New York.

The pH tuneable amido gellant may have a minimum gelling concentration (MGC) of from about 0.1 mg/mL or 0.5 mg/mL to about 100 mg/mL, 25 mg/mL, or 10 mg/mL in the personal care composition, at the target pH of the composition, in accordance with the MGC Test Method. The MGC as used herein can be represented as mg/ml or as a wt %, where wt % is calculated as the MGC in mg/ml divided by 10. In one embodiment, the MGC is at least 0.1 mg/mL, at least 0.3 mg/mL, at least 0.5 mg/mL, at least 1.0 mg/mL, at least 2.0 mg/mL, at least 5.0 mg/mL of pH tuneable amido gellant.

To provide more robust structuring, the personal care composition may comprise a mixture of two or more pH tuneable gellant structurants. Such a mixture may include a pH tuneable gellant structurants which have differing solubilities in the carrier or solvent to be structured.

Personal Care Composition

One or more of the aforementioned pH tuneable amido gellants may be incorporated into a personal care composition. The personal care composition may be a skin care, anti-perspirant, deodorant, cosmetic, or hair care product. The personal care composition may be used as, for example, a moisturizer, conditioner, anti-aging compound, skin lightener, sunscreen, sunless tanner, shave preparation, lipstick, foundation, mascara, after-shave, and combinations thereof. In certain embodiments, the composition is applied to the face, neck, hands, arms, and other typically exposed areas of the body.

The personal care composition may involve a wide variety of forms. Non-limiting examples include simple solutions (e.g., water or oil based), dispersions, and emulsions. The personal care composition may be substantially anhydrous. "Substantially anhydrous" means that the composition comprises no more than about 1%, 0.5%, or, 0% water. The personal care compositions may be fluid or solid (gels, sticks, flowable solids, amorphous materials). In certain embodiments, the personal care composition is in the form of an emulsion. Emulsion may be generally classified as having a continuous aqueous phase (e.g., oil-in-water and water-in-oil-in-water) or a continuous oil phase (e.g., water-in-oil and oil-in-water-in-oil).

In certain embodiment, the personal care composition has a turbidity of from about 5 NTU to less than about 3000 NTU, 1000 NTU, 500 NTU, or 100 NTU.

In select embodiments, the personal care composition may be in a form comprising at least one discrete, visually distinct first phase and at least one discrete, visually distinct second phase. For purposes of these select embodiments, "visually distinct" means that the phases can be separately seen by the human eye as distinctly separate regions (i.e., not emulsions or dispersions of particles. In one embodiment, at least one phase forms a stable pattern, for example a continuous or discontinuous line, a spiral, a curve, or other geometric shape, within a transparent phase, where "within" means that one phase is substantially surrounded by the other phase the and does not contact the side of a container. Alternatively, the phases may form a swirled pattern, wherein both phases alternately contact the side of a container and wherein the width of each of phase, when viewed through the side of a transparent container, is substantially constant, but may differ from each other. Alternatively, the phases may form a marbled pattern, wherein the phases alternately contact the side of the container and wherein the width of the individual phases, when viewed through the side of a transparent container, may vary throughout the composition. In one embodiment, the first phase is a transparent, clear or translucent aqueous phase and the second phase is either an opaque white or colored non-aqueous phase. In another alternative embodiment, at least one aqueous phase forms a pattern within a non-aqueous phase. It is recognized that the composition optionally may comprise a three or more visually distinct and stable phases. Discrete, visually distinct multi-phase compositions are described in U.S. Patent Application Publication Nos. 2007/0297996, 2004/0057920, and 2004/0219119.

Carriers

The personal care composition may comprise a carrier. Carriers may be selected for various stability, aesthetics, and/or compatibility with other materials present in the personal care composition.

Suitable carriers include water and/or water-equivalent solvents. The personal care composition may comprise from about 1% to about 95% by weight of water and/or water-equivalent solvent. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% water and/or a water-equivalent solvent. "Water-equivalent solvent" refers to a compound which has a similar ability as water to solubilize a material. Suitable Water-equivalent solvents include monohydric alcohols, dihydric alcohols, polyhydric alcohols, glycerol, glycols, polyalkylene glycols such as polyethylene glycol, and mixtures thereof. Particularly suitable solvents, include lower aliphatic alcohols such as ethanol, propanol, butanol, isopropanol; diols such as 1,2-propanediol, 1,3-propanediol, butanediol, pentanediol, hexanediol, heptanediol, decanediol; glycerin; water, and mixtures thereof. In certain embodiments, the personal care composition comprises water, diols, glycerin, and combinations thereof.

Suitable carriers also include oils. The personal care composition may comprise from about 1% to about 95% by weight of one or more oils. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% of one or more oils. Oils may be used to solubilize, disperse, or carry materials that are not suitable for water or water-equivalent solvents. Suitable oils include silicones, hydrocarbons, esters, fatty amides, ethers, and mixtures thereof. Oils may be fluid at room temperature. However, certain personal care product forms (i.e., solid or semi-solid stick) may require non-fluid oils. The oils may be volatile or nonvolatile. "Nonvolatile" means a material that exhibits a vapor pressure of no more than about 0.2 mm Hg at 25° C. at one atmosphere and/or a material that has a boiling point at one atmosphere of at least about 300° C. "Volatile" means that the material exhibits a vapor pressure of at least about 0.2 mm of mercury at 20° C. Volatile oils may be used to provide a lighter feel when a heavy, greasy film is undesirable.

Suitable oils include volatile oils. In certain embodiments, the volatile oils may have a viscosity ranging from about 0.5 to about 5 centistokes 25° C. Volatile oils may be used to promote more rapid drying of the skin care composition after it is applied to skin. Nonvolatile oils are also suitable for use in the composition. Nonvolatile oils are often used for emolliency and protective properties. Nonvolatile oils preferably may have a viscosity ranging from about 5 to about 800,000 cst (or greater) or from about 20 to about 200,000 cst.

Suitable silicone oils include polysiloxanes. Polysiloxanes may have a viscosity of from about 0.5 to about 1,000,000 centistokes at 25° C. Such polysiloxanes can be represented by the general chemical formula:

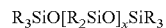

wherein R is independently selected from hydrogen or $C_{1-30}$ straight or branched chain, saturated or unsaturated alkyl, phenyl or aryl, trialkylsiloxy; and x is an integer from 0 to about 10,000, chosen to achieve the desired molecular. In certain embodiments, R is hydrogen, methyl, or ethyl. Commercially available polysiloxanes include the polydimethylsiloxanes, which are also known as dimethicones, examples of which include the DM-Fluid series from Shin-Etsu, the Vicasil® series sold by Momentive Performance Materials Inc., and the Dow Corning® 200 series sold by Dow Corning Corporation. Specific examples of suitable polydimethylsiloxanes include Dow Corning® 200 fluids (also sold as Xiameter® PMX-200 Silicone Fluids) having viscosities of 0.65, 1.5, 50, 100, 350, 10,000, 12,500 100,000, and 300,000 centistokes.

Suitable dimethicones include those represented by the chemical formula:

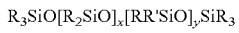

wherein R and R' are each independently hydrogen or $C_{1-30}$ straight or branched chain, saturated or unsaturated alkyl, aryl, or trialkylsiloxy; and x and y are each integers of 1 to 1,000,000 selected to achieve the desired molecular weight. Suitable silicones include phenyl dimethicone (Botansil™ PD-151 from Botanigenics, Inc.), diphenyl dimethicone (KF-53 and KF-54 from Shin-Etsu), phenyl trimethicone (556 Cosmetic Grade Fluid from Dow Corning), or trimethylsiloxyphenyl dimethicone (PDM-20, PDM-200, or PDM-1000 from Wacker-Belsil). Other examples include alkyl dimethicones wherein at least R' is a fatty alkyl (e.g., $C_{12-22}$). A suitable alkyl dimethicone is cetyl dimethicone, wherein R' is a straight C16 chain and R is methyl. Cetyl dimethicone, is available as s 2502 Cosmetic Fluid from Dow Corning or as Abil Wax 9801 or 9814 from Evonik Goldschmidt GmbH.

Cyclic silicones are one type of silicone oil that may be used in the composition. Such silicones have the general formula:

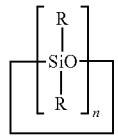

wherein R is independently selected from hydrogen or $C_{1-30}$ straight or branched chain, saturated or unsaturated alkyl, phenyl or aryl, trialkylsiloxy; and where n=3-8 and mixtures thereof. Commonly, a mixture of cyclomethicones is used where n is 4, 5, and/or 6. Commercially available cyclomethicones include Dow Corning UP-1001 Ultra Pure Fluid (i.e. n=4), Dow Corning XIAMETER® PMX-0245 (i.e. n=5), Dow Corning XIAMETER® PMX-0245 (i.e. n=6), Dow Corning 245 fluid (i.e. n=4 and 5), and Dow Corning 345 fluid (i.e. n=4, 5, and 6).

Other silicone oils suitable for use in the personal care composition include polymers having the general formula:

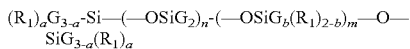

wherein G is hydrogen, phenyl, hydroxy, or $C_1$-$C_8$ alkyl, preferably methyl; a is a number 0-3; b is 0 or 1, preferably 1; n is a number from 0 to 1,999 (alternately, from 49 to 499); m is an integer from 1 to 2,000 (alternately, from 1 to 10); the sum of n and m is a number from 1 to 2,000 (alternately, from 50 to 500); $R_1$ is a monovalent radical conforming to the general formula $(CH_2)_qL$, wherein q is an integer having a value from 1 to 8 and L is selected from the following groups:

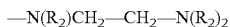

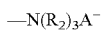

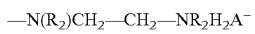

wherein $R_2$ is hydrogen, phenyl or aryl, or a saturated hydrocarbon radical, preferably an alkyl radical from about $C_1$ to about $C_{20}$, and $A^-$ is a halide ion. An exemplary silicone polymer is trimethylsilylamodimethicone as shown in the following formula:

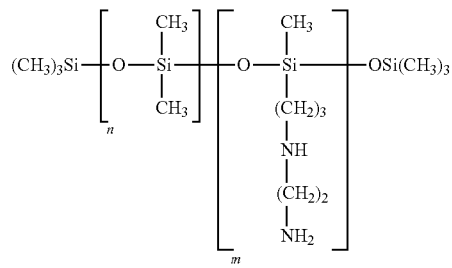

Another exemplary silicone polymer is represented by the general formula:

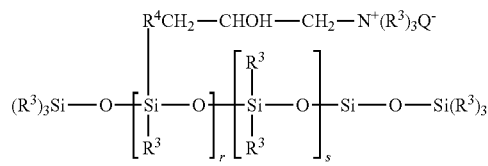

wherein $R^3$ is a monovalent hydrocarbon radical from $C_1$ to $C_{18}$, preferably an alkyl or alkenyl, such as methyl; $R_4$ is a hydrocarbon, preferably a $C_1$ to $C_{18}$ alkylene or a $C_{10}$ to $C_{18}$ alkyleneoxy, more preferably a $C_1$ to $C_8$ alkyleneoxy; $Q^-$ is a halide ion, preferably chloride; r is an average statistical value from 2 to 20, preferably from 2 to 8; s is an average statistical value from 20 to 200, preferably from 20 to 50. A suitable polymer of this class is known as UCARE SILICONE ALE 56™, available from Union Carbide. Other suitable silicone materials are disclosed in US Patent Application Publication No. 2007/0039103 A1.

Suitable hydrocarbon oils include straight or branched chain alkanes and alkenes. The chain length may be selected based on desired functional characteristics such as volatility. Suitable hydrocarbon oils may have between 5-20 carbon atoms or, alternately, between 8-16 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105. Suitable hydrocarbons include isooctane, isododecane, isohexadecane, isoeicosane by Permethyl Corporation under the tradename Permethyl®. Suitable hydrocarbon oils may have greater than about 20 carbon atoms. Examples of such hydrocarbon oils include $C_{24-28}$ olefins, $C_{30-45}$ olefins, $C_{20-40}$ isoparaffins, hydrogenated polyisobutene, polyisobutene, polydecene, hydrogenated polydecene, mineral oil, pentahydrosqualene, squalene, squalane, and mixtures thereof.

Other suitable oils include esters. Suitable esters typically contained at least 10 carbon atoms. These esters include esters with hydrocarbyl chains derived from fatty acids or alcohols (e.g., mono-esters, polyhydric alcohol esters, and di- and tri-carboxylic acid esters). The hydrocarbyl radicals of the esters hereof may include or have covalently bonded thereto other compatible functionalities, such as amides and alkoxy moieties (e.g., ethoxy or ether linkages, etc.). Exemplary esters include, but are not limited to, isopropyl isostearate, hexyl laurate, isohexyl laurate, isohexyl palmitate, isopropyl palmitate, decyl oleate, isodecyl oleate, hexadecyl stearate, decyl stearate, isopropyl isostearate, dihexyldecyl adipate, lauryl lactate, myristyl lactate, cetyl lactate, oleyl stearate, oleyl oleate, oleyl myristate, lauryl acetate, cetyl propionate, and oleyl adipate. Other suitable esters are further described in the Personal Care Product Council's *International Cosmetic Ingredient Dictionary and Handbook*, Thirteenth Edition, 2010, under the functional category of "Esters."

Other esters suitable for use in the personal care composition include mono-carboxylic acid esters of the general formula R'COOR, wherein R' and R are straight or branched chain, saturated or unsaturated alkyl, aryl, and wherein sum of carbon atoms in R' and R is at least 10, A suitable monoester is alkyl benzoate such as C12-15 alkyl benzoate.

Other esters suitable for use in the personal care composition include di- and tri-alkyl and alkenyl esters of carboxylic acids, such as esters of $C_4$ to $C_8$ dicarboxylic acids (e.g. $C_1$ to $C_{22}$ esters, preferably $C_1$ to $C_6$, of succinic acid, glutaric acid, and adipic acid). Specific non-limiting examples of di- and tri-alkyl and alkenyl esters of carboxylic acids include isocetyl stearyl stearate, diisopropyl adipate, dibutyl adipate, and tristearyl citrate.

Other esters suitable for use in the personal care composition include those known as polyhydric alcohol esters. Such polyhydric alcohol esters include alkylene glycol esters, such as ethylene glycol mono and di-fatty acid esters, diethylene glycol mono- and di-fatty acid esters, polyethylene glycol mono- and di-fatty acid esters, propylene glycol mono- and di-fatty acid esters, polypropylene glycol monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Still other esters suitable for use in the personal care composition include glycerides, including, but not limited to, mono-, di-, and tri-glycerides. For use in the compositions described herein, the glycerides may be mono-, di-, and tri-esters of glycerol and long chain carboxylic acids, such as $C_{10}$ to $C_{22}$ carboxylic acids. A variety of these types of materials can be obtained from vegetable and animal fats and oils, such as castor oil, safflower oil, cottonseed oil, corn oil, olive oil, cod liver oil, almond oil, avocado oil, palm oil, sesame oil, sweet almond oil, apricot kernel oil, *camelina sativa* oil, rapeseed oil, tamanu seed oil, linseed oil, coconut oil, lanolin oil, soybean oil, and the like. Synthetic oils include, but are not limited to, triolein and tristearin glyceryl dilaurate. Other glyceryl esters of fatty acids include fatty acid mono-, di-, and triglycerides which are natural fats or oils that have been modified such as glyceryl stearate, diglyceryl diiosostearate, polyglyceryl-3 isostearate, polyglyceryl-4 isostearate, polyglyceryl-6 ricinoleate, glyceryl dioleate, glyceryl diisotearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and the like.

Other suitable oils include fatty amides. Fatty amides include compounds having an amide functional group while being liquid at 25° C. and insoluble in water. In certain embodiments, the fatty amide may have the general formula:

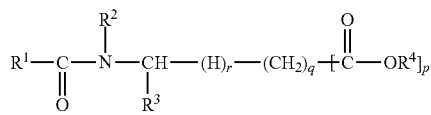

wherein R1 is an optionally functionalized, aliphatic, cycloaliphatic or cyclic, saturated or unsaturated, monovalent hydrocarbon radical containing from 1 to 30 carbon atoms (alternately, from 1 to 22 carbon atoms); R2, R3 and R4, which may be identical or different, are hydrogen or optionally functionalized, aliphatic, cycloaliphatic or cyclic, saturated or unsaturated, monovalent hydrocarbon radicals containing from 1 to 30 carbon atoms, preferably from 1 to 22 carbon atoms; r is 0 or 1; q is an integer from 0 to 2; and p equals 0 or 1. Particular fatty amides include N-acetyl-N-butylaminopropionate, isopropyl N-lauroylsarcosinate, and N,N,-diethyltoluamide. Other suitable fatty amides are disclosed in U.S. Pat. No. 6,872,401.

Other suitable oils include ethers. Suitable ethers include saturated and unsaturated fatty ethers of a polyhydric alcohol, and alkoxylated derivatives thereof. Exemplary ethers include $C_{4-20}$ alkyl ethers of polypropylene glycols, and di-$C_{8-30}$ alkyl ethers. Suitable examples of these materials include PPG-14 butyl ether, PPG-15 stearyl ether, dioctyl ether, dodecyl octyl ether, and mixtures thereof.

Emulsifiers

The personal care composition may comprise an emulsifier. An emulsifier is particularly suitable when the composition is in the form of an emulsion or if immiscible materials are being combined. The skin care composition may comprise from about 0.05%, 0.1%, 0.2%, 0.3%, 0.5%, or 1% to about 20%, 10%, 5%, 3%, 2%, or 1% emulsifier. Emulsifiers may be nonionic, anionic or cationic. Non-limiting examples of emulsifiers are disclosed in U.S. Pat. No. 3,755,560, U.S. Pat. No. 4,421,769, and McCutcheon's, *Emulsifiers and Detergents*, 2010 Annual Ed., published by M. C. Publishing Co. Other suitable emulsifiers are further described in the Personal Care Product Council's *International Cosmetic Ingredient Dictionary and Handbook*, Thirteenth Edition, 2006, under the functional category of "Surfactants—Emulsifying Agents."

Suitable emulsifying ethers and esters include:

Ethers of polyglycols and of fatty alcohols—including saturated or unsaturated $C_{12-30}$ alcohols (e.g., oleyl alcohol, cetyl alcohol, stearyl alcohol or behenyl alcohol) and polyglycols comprising n number of oxyalkylene groups wherein n=an integer from 1 to 200 or, alternately, from 2 to 30 (e.g., 1 to 20 oxyethylene groups). Particular examples include compounds with the INCI names of steareth-n, beheneth-n or oleth-n. Suitable examples include compounds having the INCI names steareth-8, steareth-10, steareth-16, steareth-20, ceteth-10, laureth-4, laureth-3, trideceth-6, ceteareth-5, oleth-10, and beneth-10.

Esters of polyglycols and of fatty acids—including saturated or unsaturated $C_{12-30}$ fatty acids (e.g., oleic acid, cetylic acid, stearic acid) and polyglycols comprising n number of oxyalkylene groups wherein n=an integer from 1 to 200 or alternately, 1 to 50 (e.g., 1 to 20 oxyethylene groups). Particular examples include compounds with the INCI name PEG-n stearate or PEG-n oleate). Suitable examples include polyethylene glycol-8 monostearate, polyethylene glycol-10, or polyethylene glycol-12 distearate.

Ethers of polyglycols and of fatty alcohols which are glycosylated—including $C_{12-30}$ alcohols having from 1 to 10 glycosyl groups and polyglycols comprising n number of oxyalkylene groups wherein n=an integer from 1 to 200 (e.g., 1 to 20 oxyethylene groups). A suitable example includes polyoxyethylenated (20OE) methyl glucose distearate, Esters of polyglycols and of fatty acids which are glycosylated—including $C_{12-30}$ fatty acids having from 1 to 10 glycosyl groups and polyglycols comprising n number of oxyalkylene groups wherein n=an integer from 1 to 200 (e.g., 1 to 20 oxyethylene groups).

Ethers of $C_{12-30}$ alcohols and of glycerol or of polyglycerol—A suitable example includes polyglyceryl-3 cetyl ether, such as Chimexane NL from Chimex, Esters of $C_{12-30}$ fatty acids and of glycerol or of polyglycerol—including esters comprising from 1 to 10 glycerol groups. Particular examples include hexa-glyceryl monosterate, diglyceryl distearate, tetraglyceryl tristearate, decaglyceryl decastearate, diglyceryl monostearate, hexaglyceryl tristearate, decaglyceryl pentastearate, the ester of glycerol and of palmitic and stearic acids, and glyceryl mono- and dibehenate.

Ethers of oxyalkylene-modified $C_{12-30}$ alcohols and of glycerol or polyglycerol.

Ethers of $C_{12-30}$ fatty alcohols comprising and of sucrose or of glucose—Suitable examples include compounds with the INCI names of C12-18 alkylglucoside, C12-20 alkylglucoside (e.g., Montanov L from Seppic), cetearyl glucoside (e.g., a mixture with cetearyl alcohol under the reference Montanov 68 from Seppic), myristyl glucoside (e.g., a mixture with myristyl alcohol under the reference Montanov 14 from Seppic) or cetearyl glucoside (e.g., Tegocare CG 90 from Evonik Goldschmidt), Esters of sucrose and of $C_{12-30}$ fatty acids—Particular examples include sucrose distearate or sucrose tristearate, sucrose cocoate, sucrose dilaurate, sucrose distearate, sucrose hexaerucate, sucrose hexapalmitate, sucrose laurate, sucrose mortierellate, sucrose myristate, sucrose oleate, sucrose palmitate, sucrose pentaerucate, sucrose polybehenate, sucrose polycottonseedate, sucrose polylaurate, sucrose polylinoleate, sucrose polyoleate, sucrose polypalmate, sucrose polysoyate, sucrose polystearate, sucrose ricinoleate, sucrose stearate, sucrose tetraisostearate, and sucrose trilaurate. A suitable example includes the mixture of esters (mono- and polyesters) of stearic acid and of sucrose sold as Crodesta F1 10 by Croda.

Esters of pentaerythritol and of $C_{12-30}$ fatty acids—Particular examples include pentaerythritol tetrastearate.

Esters of sorbitol and/or of sorbitan and of $C_{12-30}$ fatty acids—Particular examples include sorbitan monostearate, sorbitan tristearate, or sorbitan laurate, such as Span 20 from Uniqema, Ethers of sorbitol and/or of sorbitan and of alkoxylated sorbitan—Suitable examples include sorbeth-8 beeswax or sorbeth-20 beeswax from Nikko Chemical.

Ethers of polyglycols and of cholesterol—Particular examples include choleth-3, choleth-10 (such as Emalex CS-10 from Nihon Emulsion Company), choleth-15 (such as Emalex CS-15 from Nihon Emulsion Company) or choleth-20 (such as Emalex CS-20 from Nihon Emulsion Company).

Esters of $C_{12-30}$ fatty acids and of alkoxylated ethers of sorbitol and/or of Suitable examples include polysorbate-60, polysorbate-61, sorbeth-3 isostearate, polyoxyethylenated 4 OE sorbitan monostearate, and polyoxyethylenated 200E sorbitan tristearate.

Linear or branched type silicone emulsifiers may also be used. Particularly useful polyether modified silicones include KF-6011, KF-6012, KF-6013, KF-6015, KF-6015, KF-6017, KF-6043, KF-6028, and KF-6038 from Shin Etsu. Also particularly useful are the polyglycerolated linear or branched siloxane emulsifiers including KF-6100, KF-6104, and KF-6105 from Shin Etsu. Exemplary materials include materials with the following International Nomenclature of Cosmetic Ingredients (INCI) designations: Bis-Butyldimethicone Polyglyceryl-3; Bis-PEG/PP G-14/14 Dimethicone; Bis-butyldimethicone Polyglyceryl-3; Bis-isobutyl PEG/PPG-10/7 Dimethicone copolymer; Bis-PEG/PPG-18/6 Dimethicone; Bis-PEG/PPG-20/20 Dimethicone; Bis-PEG/PPG-16/16 PEG/PPG-16/16 Dimethicone; Bis(PPG-7 Undeceneth-21-Dimethicone; Cetyl Dimethicone PEG-7 Acetate; Cetyl PEG-8 Dimethicone; Cetyl PEG/PPG-15/16 Butyl Ether Dimethicone; Cetyl PEG/PPG-15/15 Butyl Ether Dimethicone; Cetyl PEG/PPG-7/3 Dimethicone; Cetyl PEG/PPG-10/1 Dimethicone; Dimethicone PEG-15 Acetate; Dimethicone PEG-7 Cocoate; Dimethicone PEG-7 Phosphate; Dimethicone PEG-10 Phosphate; Dimethicone PEG/PPG-7/4 Phosphate; Dimethicone PEG/PPG-12/4 Phosphate; Dimethicone PEG-7 Undecylenate; Lauryl Dimethicone PEG-10 Phosphate; Isopolyglyceryl-3 Dimethicone; Isopolyglyceryl-3 Dimethiconol; Isostearyl Carboxyldecyl PEG-8 Dimethicone; Lauryl Methicone PEG-10 Phosphate; Lauryl PEG-8 Dimethicone; Lauryl PEG-10 Methyl Ether Dimethicone; Lauryl PEG/PPG-18/18 Methicone; PEG-6 Methyl Ether Dimethicone; PEG-7 Methyl Ether Dimethicone; PEG-9 Methyl Ether Dimethicone; PEG-10 Methyl Ether Dimethicone; PEG-11 Methyl Ether Dimethicone; PEG-11 Methyl Ether Dimethicone; PEG-32 Methyl Ether Dimethicone; PEG-PEG/PPG-28/21 Acetate Dimethicone; PEG/PPG-22/22 Butyl Ether Dimethicone; PEG/PPG-23/23 Butyl Ether Dimethicone; PEG/PPG-24/18 Butyl Ether Dimethicone; PEG/PPG-3/10 Dimethicone; PEG/PPG-4/12 Dimethicone; PEG/PPG-6/11 Dimethicone; PEG/PPG-8/14 Dimethicone; PEG/PPG-12/16 Dimethicone; PEG/PPG-12/18 Dimethicone; PEG/PPG-14/4 Dimethicone; PEG/PPG-15/5 Dimethicone; PEG/PPG-15/15 Dimethicone; PEG/PPG-16/2 Dimethicone; PEG/PPG-16/8 Dimethicone; PEG/PPG-17/18 Dimethicone; PEG/PPG-18/12 Dimethicone; PEG/PPG-19/19 Dimethicone; PEG/PPG-20/6 Dimethicone; PEG/PPG-20/15 Dimethicone; PEG/PPG-20/20 Dimethicone; PEG/PPG-20/29 Dimethicone; PEG/PPG-22/23 Dimethicone; PEG/PPG-22/24 Dimethicone; PEG/PPG-25/25 Dimethicone; PEG/PPG-27/27 Dimethicone; PEG/PPG-30/10 Dimethicone; PEG/PPG-10/3 Oleyl Ether Dimethicone; PEG-8 trisiloxane; Polyglyceryl-3 Polydimethylsiloxyethyl Dimethicone; PPG-12 Butyl Ether Dimethicone; Silicone Quaternium-17; TEA-Dimethicone PEG-7 Phosphate; and mixtures thereof.

Emulsifiers also include emulsifying silicone elastomers. Suitable emulsifying silicone elastomers may include at least one polyalkyl ether or polyglycerolated unit. These crosslinked elastomers may also be co-modified to include alkyl substituents. Suitable formation techniques are described in U.S. Pat. Nos. 5,236,986; 5,412,004; 5,837,793; and 5,811,487. Polyoxyalylenated emulsifying silicone elastomers that may be used in at least one embodiment of the invention include those sold by Shin-Etsu Silicones under the names KSG-21, KSG-20, KSG-30, KSG-31, KSG-32, KSG-33; KSG-210 (dimethicone/PEG-10/15 crosspolymer dispersed in dimethicone); KSG-310 (PEG-15 lauryl dimethicone crosspolymer); KSG-320 (PEG-15 lauryl dimethicone crosspolymer dispersed in isododecane); KSG-330 (PEG-15 lauryl dimethicone crosspolymer dispersed in triethylhexanoin), KSG-340 (PEG-10 lauryl dimethicone crosspolymer and PEG-15 lauryl dimethicone crosspolymer). Other silicone emulsifying elastomers are supplied by Dow Corning™, including PEG-12 dimethicone crosspolymers (DC 9010 and 9011). Other suitable silicone emulsifiers sold by Dow Corning include DC9010 and DC9011.

Polyglycerolated emulsifying silicone elastomers are disclosed in PCT/WO 2004/024798. Such elastomers include Shin-Etsu's KSG series, such as KSG-710 (dimethicone/polyglycerin-3 crosspolymer dispersed in dimethicone); or lauryl dimethicone/polyglycerin-3 crosspolymer dispersed in a variety of solvent such as isododecane, dimethicone, triethylhexanoin, available as KSG-810, KSG-820, KSG-830, or KSG-840 from Shin-Etsu.

Another suitable crosslinked silicone elastomer emulsifier is dimethicone/PEG-10/15 crosspolymer, which provides excellent aesthetics due to its elastomeric backbone, but also excellent emulsification properties. Further examples of crosslinked organosiloxane emulsifiers include, but are not limited to dimethicone/dimethicone PEG/PPG 15 crosspolymer; dimethicone PEG-10 crosspolymer; dimethicone PEG-10/15 crosspolymer; dimethicone PEG-15 crosspolymer; dimethicone polyglycerin-3 crosspolymer; dimethicone PPG-20 crosspolymer; lauryl dimethicone PEG-15 crosspolymer; lauryl dimethicone polyglycerin-3 crosspolymer; PEG-8 dimethicone polysorbate-20 crosspolymer; PEG-10 dimethicone/vinyl dimethicone crosspolymer; PEG-10 lauryl dimethicone crosspolymer; PEG-15/lauryl dimethicone crosspolymer; PEG-15 laurylpolydimethylsiloxy ethyl crosspolymer; and mixtures thereof.

It should be recognized that silicone elastomers may be supplied pre-swollen with a solvent. With a pre-swollen swollen elastomer, the weight percentages recited for emulsifier use (i.e., from about 0.05% to about 20%, from about 0.1% to about 10%, from about 0.5% to about 5%, or from about 1% to about 3% emulsifier) are of the elastomer alone (i.e., excluding the weight of the solvent).

Structuring Agent

The personal care composition may comprise structuring agent in addition to the pH tuneable amido gellant described above. Structuring agents may be used to increase viscosity, thicken, solidify, or provide solid or crystalline structure to the personal care composition. Structuring agents are typically grouped based on solubility, dispersibility, or phase compatibility. Examples of aqueous or water structuring agents include polymeric agents, natural or synthetic gums, polysaccharides, and the like. In one embodiment, the composition may comprises from about 0.0001%, 0.001%, 0.01%, 0.05%, 0.1%, 0.5%, 1%, 2%, 3%, 5% to about 25%, 20%, 10%, 7%, 5%, 4%, or 2%, by weight of the composition, of one or more structuring agents.

Polysaccharides and gums may be used as aqueous phase thickening agents. Examples of such polysaccharides and gums include naturally derived materials such as agar, agarose, *alicaligenes* polysaccharides, algin, alginic acid, *acacia* gum, amylopectin, chitin, dextran, cassia gum, cellulose gum, gelatin, gellan gum, hyaluronic acid, hydroxyethyl cellulose, methyl cellulose, ethyl cellulose, pectin, sclerotium gum, xanthan gum, pectin, trehelose, gelatin, ammonium alginate, calcium alginate, calcium carrageenan, carnitine, carrageenan, guar gum, guar hydroxypropyltrimonium chloride, hyaluronic acid, hydroxypropyl chitosan, hydroxypropyl guar, karaya gum, kelp, locust bean gum, natto gum, potassium alginate, potassium carrageenan, propylene glycol alginate, sodium carboxymethyl dextran, sodium carrageenan, tragacanth gum, and mixtures thereof. Suitable polysaccharides include alkyl hydroxyalkyl cellulose ethers such as cetyl hydroxyethylcellulose, which is the ether of cetyl alcohol and hydroxyethylcellulose. This material is sold under the tradename Natrosol® Plus CS from Ashland Aqualon Functional Ingredients. Other useful polysaccharides include scleroglucans comprising a linear chain of (1-3) linked glucose units with a (1-6) linked glucose every three units, a commercially available example of which is Clearogel™ CS11 from M.M.P., Inc.

Suitable classes of polymeric structuring agents include but are not limited to carboxylic acid polymers, polyacrylamide polymers, sulfonated polymers, high molecular weight polyalkylglycols or polyglycerins, copolymers thereof, hydrophobically modified derivatives thereof, and mixtures thereof.

Carboxylic acid polymers include carbomers. These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Suitable materials includes include the Carbopol® 900 series (e.g., Carbopol® 945, Carbopol® 940, Carbopol® 950, Carbopol® 954, Carbopol® 980, Carbopol® 951 and Carbopol® 981 from Noveon, Inc) and the Carbopol® Ultrez series (e.g., Carbopol® Ultrez 10 polymer, Carbopol® Ultrez 20 polymer, and Carbopol® Ultrez 21 polymer). Other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, PEMULEN™ TR-1, and PEMULEN™ TR-2, from Noveon, Inc.

Sulfonated polymers include polymers and copolymers containing 2-acrylamido-2-methylpropane sulfonic acid (i.e., AMPS or acryloyldimethyl tauric acid) and salts thereof. Exemplary AMPS structurants include sodium acrylate/sodium acryloyldimethyl taurate copolymer available as SIMULGEL® EG and SIMULGEL® EPG or hydroxyethyl acrylate/sodium acryloyldimethyl taurate copolymer available as SIMULGEL® NS, SIMULGEL® FL, and SIMULGEL® I-NS 100; which are available from Seppic Corporation (Fairfield, N.J.). Another suitable sulfonated polymer is sodium polyacryloyldimethyl taurate available as Simulgel® 800 from Seppic Corporation (Fairfield, N.J.). Other suitable sulfonated polymers include acrylamide/sodium acryloyldimethyltaurate/acrylic acid copolymer available as Acudyne™ SCP from Rohm and Haas Company, Inc.; acrylamide/sodium acryloyldimethyltaurate copolymer available as Simulgel® 600 from Seppic; ammonium acryloyldimethyltaurate/beheneth-25 methacrylate crosspolymer available as Aristoflex® BLV from Clariant International Ltd.; ammonium acryloyl dimethyltaurate/carboxyethyl acrylate crosspolymer available as Aristoflex® TAC from Clariant International Ltd.; ammonium acryloyldimethyltaurate/vinylpyrrolidone copolymer available as Aristoflex® AVC from Clariant International Ltd.; dimethylacrylamide/sodium acryloyldimethyltaurate crosspolymer available as SUpolymer G-1 from Toho Chemical Industry Co., Ltd.; sodium acrylate/acryloyldimethyltaurate/dimethylacrylamide crosspolymer available as Sepinov™ P88 from Seppic; and sodium acryloyldimethyltaurate/VP Crosspolymer available as Aristoflex® AVS from Clariant International, Ltd. Additional sulfonated structurants are described in US Patent Application Publication Nos. 2007/0140993 (identified as gelling agent in the form of a copolymer of acryloyl dimethyl tauric acid or a salt thereof) and 2006/0147396A1 (identified as "polymer containing at least one sulpho-functional monomer").

Acrylamide polymers and copolymers include SEPIGEL® 305 from Seppic Corporation (Fairfield, N.J.), which is designated by the Personal Care Product Council's *International Cosmetic Ingredient Dictionary and Handbook*, Thirteenth Edition, 2010, as "polyacrylamide and isoparaffin and laureth-7." Other polyacrylamide polymers include multi-block copolymers of acrylamides and substituted acrylamides with acrylic acids and substituted acrylic acids. Commercially available examples of these multi-block copolymers include HYPAN® SR150H, SS500V, SS500 W, SSSA100H, from Lipo Chemicals, Inc., (Patterson, N.J.).

High molecular weight polyalkylglycols or polyglycerins may be used as structuring agents. Suitable materials include polyethylene glycols (PEG) derivatives and polypropylene glycols (PPG) derivatives with an n degree of polymerization. n may be from 50 to 200,000. Other suitable materials are having repeating glycerin moieties where the number of repeating moieties ranges from 15 to 200, or from about 20-100. Examples of suitable polyglycerins include those having the INCI names polyglycerin-20, polyglycerin-40, and the like.

Examples of oil structuring agents include silicone and organic based materials. Suitable ranges of oil structuring agents are from about 0.01%, 0.05%, 0.1% 0.5%, 1%, 2.5%, 5%, or 10% to about 30%, 25%, 20%, 15%, 10%, or 5%. Suitable oil phase structuring agents may be silicone based, such as silicone elastomers, silicone gums, silicone waxes, linear silicones having a degree of polymerization allowing the silicone to increase the viscosity of the oil phase. Examples of silicone structuring agents include, but are not limited to, silicone elastomers, silicone gums, and silicone waxes, Silicone elastomers suitable for use in the compositions of the invention include those that are formed by addition reaction-curing, by reacting an SiH-containing diorganosiloxane and an organopolysiloxane having terminal olefinic unsaturation, or an alpha-omega diene hydrocarbon, in the presence of a platinum metal catalyst. Such elastomers may also be formed by other reaction methods such as condensation-curing organopolysiloxane compositions in the presence of an organotin compound via a dehydrogenation reaction between hydroxyl-terminated diorganopolysiloxane and SiH-containing diorganopolysiloxane or alpha omega diene; or by condensation-curing organopolysiloxane compositions in the presence of an organotin compound or a titanate ester using a condensation reaction between an hydroxyl-terminated diorganopolysiloxane and a hydrolysable organosiloxane; peroxide-curing organopolysiloxane compositions which thermally cure in the presence of an organoperoxide catalyst. Cross-linked organopolysiloxane elastomers useful in the present invention and processes for making them are further described in U.S. Pat. Nos. 4,970,252, 5,760,116, and 5,654, 362, 6,524,598, and 6,696,049. It is particularly desirable to incorporate silicone elastomers into the compositions of the invention because they provide excellent "feel" to the composition, are very stable in cosmetic formulations, and relatively inexpensive.

Suitable silicone elastomers may be in the powder form, or dispersed or solubilized in solvents such as volatile or nonvolatile silicones, or silicone compatible vehicles such as hydrocarbons or esters. Examples of silicone elastomer powders include vinyl dimethicone/methicone silsesquioxane crosspolymers like KSP-100, KSP-101, KSP-102, KSP-103, KSP-104, KSP-105, available from Shin-Etsu, hybrid silicone powders that contain a fluoroalkyl group like KSP-200, available from Shin-Etsu, which is a fluoro-silicone elastomer, and hybrid silicone powders that contain a phenyl group such as KSP-300, available from Shin-Etsu, which is a phenyl substituted silicone elastomer; and DC 9506 available from Dow Corning.

Examples of silicone elastomer dispersed in a silicone compatible vehicle include dimethicone/vinyl dimethicone crosspolymers supplied by a variety of suppliers including Dow Corning Corporation under the tradenames DC9040 or DC9041, Momentive under the tradename SFE 839, or Shin-Etsu Silicones under the tradenames KSG-15, 16, 18. KSG-15 has the INCI name cyclopentasiloxane (and) dimethicone/vinyl dimethicone crosspolymer. KSG-18 has the INCI name diphenylsiloxy phenyl trimethicone (and) dimethicone/phenyl vinyl dimethicone crosspolymer. Silicone elastomers may also be purchased from Grant Industries under the Gransil trademark. Other suitable silicone elastomers have long chain alkyl substitutions such as lauryl dimethicone/vinyl dimethicone crosspolymers supplied by Shin Etsu under the tradenames KSG-31, KSG-32, KSG-41, KSG-42, KSG-43, and KSG-44.

Silicone gums are another oil phase structuring agent. The silicone gum typically has a viscosity ranging from about 500,000 to 100 million cst at 25° C., from about 600,000 to 20 million, from about 600,000 to 12 million cst. The silicone gums that are used in the compositions include, but are not limited to, those of the general formula wherein:

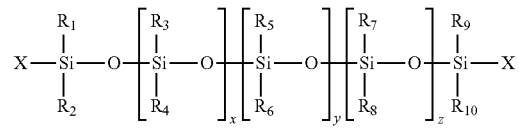

$R_1$ to $R_{10}$ are each independently hydrogen, an alkyl having 1 to 30 carbon atoms, aryl, or aralkyl; and X is H, OH, or a $C_{1-30}$ alkyl or vinyl. x, y, or z may be zero with the proviso that $(x+y+z) \geq 1$.

Such silicone gums may be purchased in pure form from a variety of silicone manufacturers including Wacker-Chemie or Dow Corning, and the like. Silicone gums include those sold by Wacker-Belsil under the trade names CM3092, Wacker-Belsil 1000, or Wacker-Belsil DM 3096. A silicone gum where X is OH, also referred to as dimethiconol, is available from Dow Corning Corporation under the trade name 1-1254 Fluid, 2-9023 Fluid, and 2-9026 Fluid. The silicone gum may also be purchased in the form of a solution or dispersion in a silicone compatible vehicle such as volatile or nonvolatile silicone. An example of such a mixture may be purchased from Barnet Silicones under the HL-88 tradename, having the INCI name dimethicone. Another example is a mixture of dimethiconol and volatile or nonvolatile silicone available from the Dow Corning Corporation as tradename 1401 Fluid, 1403 Fluid, and 1501 Fluid.

Another type of oily phase structuring agent includes silicone waxes. Silicone waxes may be referred to as alkyl silicone waxes which and are semi-solids or solids at room temperature. The term "alkyl silicone wax" means a polydimethylsiloxane having a substituted long chain alkyl (such as C16 to 30) that confers a semi-solid or solid property to the siloxane. Examples of such silicone waxes include stearyl dimethicone, which may be purchased from Evonik Goldschmidt GmbH under the tradename Abil Wax 9800 or from Dow Corning under the tradename 2503. Another example is bis-stearyl dimethicone (which may be purchased from Gransil Industries under the tradename Gransil A-18), behenyl dimethicone, or behenoxy dimethicone.

Other suitable structuring agents include polyamides and polysilicone-polyamide copolymers. Suitable polysilicone-polyamide copolymers are disclosed in U.S. Patent Application Publication No. 2004/0170586. A specific example of such copolymers is nylon 611/dimethicone copolymers by Dow Corning under the tradename Dow Corning 2-8178.

Also suitable are polyamides such as those purchased from Arizona Chemical under the Uniclear™ and Sylvaclear® including Sylvaclear® A200V or A2614V (INCI name: ethylenediamine/hydrogenated dimer dilinoleate copolymer/bis-di-C14-18 alkyl amide); Sylvaclear® AF1900V and Sylvaclear® PA1200V (INCI name: Poly amide-3); Sylvaclear®C75V (INCI name: bis-stearyl ethylenediamine/neopentyl glycol/stearyl hydrogenated dimer dilinoleate copolymer); Sylvaclear® PE400V (INCI name: Polyamide-6); Sylvaclear® WF 1500V (INCI name: Polyamide-4); or Uniclear™ 100 VG (INCI name: ethylenediamine/stearyl dimer dilinoleate copolymer; or ethylenediamine/stearyl dimer distillate copolymer).

Other oil phase structuring agents include one or more natural or synthetic waxes such as animal, vegetable, or mineral waxes. Generally such waxes have a melting point ranging from about 25° C. to 125° C., and alternatively from about 30° C. to about 100° C. Non-limiting examples of suitable waxes include silicone waxes, fatty esters, for example cetyl and/or stearyl esters, acacia, beeswax, ceresin, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, candelilla, grape wax, polyalkylene glycol derivatives thereof (for example PEG6-20 beeswax, or PEG-12 carnauba wax) and mixtures of any of the aforementioned waxes. In one embodiment, the wax is a polyethylene wax, and alternatively is a polyethylene wax having a melting point of less than 120° C., alternatively less than 95 C, and alternatively less than 85° C.

Non-limiting examples of suitable silicone waxes are disclosed in U.S. Pat. Nos. 5,413,781 and 5,725,845, and further include alkylmethyl polysiloxanes, C10-C60 alkyl dimethicones, and mixtures thereof. Alternatively, the silicone wax may be a C16-C28 alkyl dimethicone wax. Other suitable silicone waxes include, but are not limited to stearoxydimethicone, behenoxy dimethicone, stearyl dimethicone, cetearyl dimethicone, cetyl dimethicone, and mixtures thereof.

Other structuring agents are natural or synthetic montmorillonite minerals such as hectorite, bentonite, and quaternized derivatives thereof, which are obtained by reacting the minerals with a quaternary ammonium compound (e.g., stearalkonium bentonite and stearalkonium hectorite).

Other structuring agents are silicas, silicates, silica silylate, and alkali metal or alkaline earth metal derivatives thereof. These silicas and silicates are generally found in the particulate form and include silica, silica silylate, magnesium aluminum silicate, and the like.

Optional Personal Care Ingredients

The personal care compositions may comprise one or more optional components to provide an efficacious and/or consumer desirable product. For example, the composition can include other actives or agents. For instance, suitable optional actives and agents may include an active or agent selected from a group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, particulate materials, UV actives, photostabilizers, anti-cellulite agents, desquamation actives, anti-acne actives, anti-oxidants, radical scavengers, conditioning agents, anti-inflammatory agents, tanning actives, skin lightening agents, botanical extracts, antimicrobial actives, antifungal actives, antibacterial actives, antiperspirant actives, sensates, preservatives, anti-dandruff actives, substantivity polymers, detersive surfactants, and combinations thereof. Suitable optional components are discussed in more detail below.

1. Sugar Amines

The compositions of the present invention can comprise a sugar amine, which is also known as amino sugar. Sugar amine compounds useful in the present invention can include those described in PCT Publication WO 02/076423 and U.S. Pat. No. 6,159,485. In one embodiment, the composition may comprise from about 0.001%, 0.01%, 0.05%, 0.1%, 0.5%, or 1% to about 10%, 7, 5%, or 2% by weight of the composition, of one or more sugar amine.

Sugar amines can be synthetic or natural in origin and can be used as pure compounds or mixtures of compounds (e.g., extracts from natural sources or mixtures of synthetic materials). For example, glucosamine is generally found in many shellfish and can also be derived from fungal sources. As used herein, "sugar amine" includes isomers and tautomers of such and its salts (e.g., HCl salt) and is commercially available from Sigma Chemical Co.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine.

2. Vitamins

In one embodiment, the composition may comprise from about 0.001%, 0.01%, 0.05%, 0.1%, 0.5%, or 1% to about 10%, 7, 5%, or 2%, by weight of the composition, of one or more vitamins. "Vitamins" means vitamins, pro-vitamins, and their salts, isomers and derivatives. Non-limiting examples of suitable vitamins include: vitamin B compounds (including B1 compounds, B2 compounds, B3 compound, B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids.

In certain embodiments, the personal care compositions comprise a vitamin B3 compound. Vitamin B3 compounds are particularly useful for regulating skin conditions, as described in U.S. Pat. No. 5,939,082. In one embodiment, the composition may comprise from about 0.001%, 0.01%, 0.05%, 0.1%, 0.5%, or 1% to about 50%, 20%, 10%, 7%, or 5%, by weight of the composition, of the vitamin B3 compound.

As used herein, "vitamin B3 compound" means a compound having the formula:

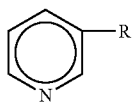

wherein R is —CONH$_2$ (i.e., niacinamide), —COOH (i.e., nicotinic acid) or —CH$_2$OH (i.e., nicotinyl alcohol); derivatives thereof; and salts of any of the foregoing.

Exemplary derivatives of the foregoing vitamin B3 compounds include nicotinic acid esters, including non-vasodilating esters of nicotinic acid (e.g., tocopherol nicotinate, myristyl nicotinate), nicotinyl amino acids, nicotinyl alcohol esters of carboxylic acids, nicotinic acid N-oxide and niacinamide N-oxide.

3. Oil Control Agents

The personal care compositions may comprise one or more oil control agents for regulating the production of skin oil, sebum, or for improving the appearance of oily skin. Examples of suitable oil control agents include salicylic acid, dehydroacetic acid, benzoyl peroxide, vitamin B3 compounds, their isomers, esters, salts and derivatives, and mixtures thereof. Dehydroacetic acid includes materials having the formula:

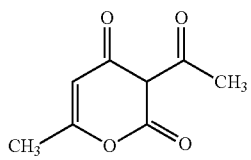

or dermatologically acceptable salts, derivatives or tautomers thereof. The technical name for dehydroacetic acid is 3-Acetyl-6-methyl-2H-pyran-2,4(3H)-dione and can be commercially purchased from Lonza.

Dermatologically acceptable salts include alkali metal salts, such as sodium and potassium; alkaline earth metal salts, such as calcium and magnesium; non-toxic heavy metal salts; ammonium salts; and trialkylammonium salts, such astrimethylammonium and triethylammonium. In particular embodiments, sodium, potassium, and ammonium salts of dehydroacetic acid may be used. Sodium dehydroacetate is available from Tri-K Industries, Inc., as Tristat SDHA. Derivatives of dehydroacetic acid include, but are not limited to, any compounds wherein the CH$_3$ groups are individually or in combination replaced by amides, esters, amino groups, alkyls, and alcohol esters. Tautomers of dehydroacetic acid are the isomers of dehydroacetic acid which can change into one another with great ease so that they ordinarily exist in equilibrium. Thus, tautomers of dehydroacetic acid can be described as having the chemical formula C$_8$H$_8$O$_4$ and generally having the formula above.

Other oil control agents include materials capable of absorbing oils and sebum. Suitable oil absorbing materials include starch, calcium silicate, polyethylene, nylon, boran nitride, mica, clays such as bentonite, montmarrillonite and kaolin, zeolite, cyclodextrins, fumed silica, synthetic clays such as polymer powders including natural, synthetic, and semisynthetic cellulose, fluorocarbon resins, polypropylene, modified starches of cellulose acetate, particulate cross-linked hydrophobic acrylate or methacrylate copolymers and mixtures thereof.

In one embodiment, the personal care composition may comprise from about 0.001%, 0.01%, 0.05%, 0.1%, 0.5%, or 1% to about 25%, 20%, 10%, 7%, 5%, or 3% by weight of the composition, of one or more oil control agents.

4. Phytosterols

The personal care compositions may comprise a phytosterol. For example, one or more phytosterols can be selected from the group consisting of β-sitosterol, campesterol, brassicasterol, Δ5-avennasterol, lupenol, α-spinasterol, stigmasterol, their derivatives, analogs, and combinations thereof. In certain embodiments, the phytosterol is selected from the group consisting of β-sitosterol, campesterol, brassicasterol, stigmasterol, their derivatives, and combinations thereof. In a select embodiment, the phytosterol is stigmasterol.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers and tautomers of such and is commercially available from Aldrich Chemical Company, Sigma Chemical Company, and Cognis.

In one embodiment, the composition may comprise from about 0.0001%, 0.001%, 0.01%, 0.05%, 0.1%, 0.5%, or 1% to about 25%, 20%, 10%, 7%, 5%, or 3%, by weight of the composition, of one or more phytosterol.

5. Hexamidine Compounds

The personal care compositions may include hexamidine compounds, its salts, and derivatives. As used herein, "hexamidine compound" means a compound having the formula:

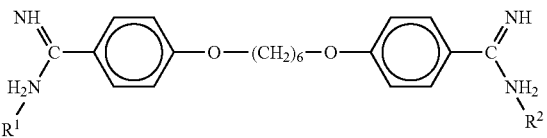

wherein R$^1$ and R$^2$ are optional or are organic acids (e.g., sulfonic acids, etc.).

In one embodiment, the composition may comprise from about 0.0001%, 0.001%, 0.01%, 0.05%, 0.1%, 0.5%, or 1% to about 25%, 20%, 10%, 7%, 5%, or 3%, by weight of the composition, of one or more hexamine compounds.

As used herein, hexamidine derivatives include any isomers and tautomers of hexamidine compounds including but not limited to organic acids and mineral acids, for example sulfonic acid, carboxylic acid, etc. In a select embodiment, the hexamidine compounds include hexamidine diisethionate, commercially available as Eleastab® HP100 from Laboratories Serobiologiques.

6. Tightening Agents

The personal care composition may comprise a tightening agent. A tightening agent is a compound capable of having a tightening effect on keratinous tissues and, typically, on skin. Suitable tightening agents may be chosen from plant or animal proteins and their hydrolysates such as maize, rye, wheat, buckwheat, sesame, spelt, pea, bean, lentil, soybean and lupin; polysaccharides of natural origin including (i) polyholosides, for example, in the form of starch derived especially from rice, maize, potato, cassava, peas, wheat, oats, etc. or in the form of carrageenans, alginates, agars, gellans, cellulose polymers and pectins, advantageously as an aqueous dispersion of gel microparticles, and (ii) latices composed of shellac resin, gum sandarac, dammars, elemis, copals, cellulose compounds, and mixtures thereof; mixed silicates including phyllosilicates and in particular laponites; colloidal particles of inorganic fillers such as silica/alumina colloidal particles such as those sold under then tradename LUDOX® by W.R. Grace & Co.; synthetic polymers such as polyurethane latices or acrylic/silicone latices, in particular those described in US Patent Application Publication No. 2002/0131948, including propylthio(polymethyl acrylate), propylthio(polymethyl methacrylate) and propylthio(polymethacrylic acid) grafted polydimethylsiloxane, propyl-thio (polyisobutyl methacrylate) and propylthio(poly-methacrylic acid) grafted polydimethylsiloxane (available under the tradenames VS 80, VS 70 and L021 from 3M); and mixtures thereof.

The personal care composition may comprise from about 0.0001%, 0.001%, 0.01%, 0.05%, 0.1%, 0.5%, or 1% to about 30%, 25%, 20%, 10%, 7%, 5%, or 3% by weight of the composition, of one or more tightening agent.

7. Anti-Wrinkle Actives/Anti-Atrophy Actives

The compositions of the present invention can comprise a one or more anti-wrinkle actives or anti-atrophy actives. Exemplary anti-wrinkle/anti-atrophy actives suitable for use in the compositions of the present invention include dialkanoyl hydroxyproline compounds, hydroxy acids (e.g., glycolic acid, lactic acid, lactobionic acid), keto acids (e.g., pyruvic acid), phytic acid, lysophosphatidic acid, stilbenes, cinnamates, resveratrol, kinetin, zeatin, dimethylaminoethanol, peptides from natural sources (e.g., soy peptides), and salts of sugar acids (e.g., Mn gluconate, Zn gluconate). In one embodiment, the composition may comprise from about 0.0001%, 0.001%, 0.01%, 0.05%, 0.1%, 0.5%, or 1% to about 30%, 25%, 20%, 10%, 7%, 5%, or 3% by weight of the composition, of one or more anti-wrinkle/anti-atrophy compounds.

Suitable dialkanoyl hydroxyproline compounds of the present invention can include those corresponding to the following chemical formula:

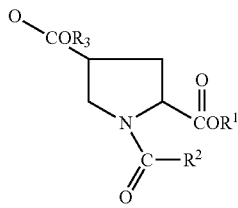

wherein $R^1$ is H, X, $C_1$-$C_{20}$ straight or branched alkyl,
X is metals (Na, K, Li, Mg, Ca) or amines (DEA, TEA);
$R^2$ is $C_1$-$C_{20}$ straight or branched alkyl;
$R^3$ is $C_1$-$C_{20}$ straight or branched alkyl.

Suitable derivatives include but are not limited to esters, for example fatty esters, including, but not limited to tripalmitoyl hydroxyproline and dipalmityl acetyl hydroxyproline. A particularly useful compound is dipalmitoyl hydroxyproline. As used herein, dipalmitoyl hydroxyproline includes any isomers and tautomers of such and is commercially available under the tradename Sepilift DPHP® from Seppic, Inc. Further discussion of dipalmitoyl hydroxyproline appears in PCT Publication WO 93/23028. Preferably, the dipalmitoyl hydroxyproline is the triethanolamine salt of dipalmitoyl hydroxyproline as discussed in U.S. Pat. No. 7,285,570.

8. Flavonoids

The compositions of the present invention can comprise a flavonoid compound. Flavonoids are broadly disclosed in U.S. Pat. Nos. 5,686,082 and 5,686,367. Examples of flavonoids particularly suitable for use in the present invention are one or more flavones, one or more isoflavones, one or more coumarins, one or more chromones, one or more dicoumarols, one or more chromanones, one or more chromanols, isomers (e.g., cis/trans isomers) thereof, and mixtures thereof.

Exemplary flavonoids include flavones and isoflavones, in particular daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy) and other plant sources of such mixtures (e.g., red clover), and mixtures thereof. Other exemplary materials include flavanones such as hesperitin, hesperidin, and mixtures thereof. Flavonoid compounds useful herein are commercially available from a number of sources, e.g., Indofine Chemical Company, Inc., Steraloids, Inc., and Aldrich Chemical Company, Inc.

In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more flavonoid compounds.

9. N-acyl Amino Acid Compounds

The topical compositions of the present invention can comprise one or more N-acyl amino acid compounds. The amino acid can be one of any of the amino acids known in the art. The N-acyl amino acid compounds of the present invention can correspond to the formula:

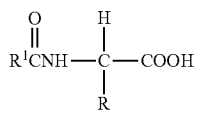

wherein R can be a hydrogen, alkyl (substituted or unsubstituted, branched or straight chain), or a combination of alkyl and aromatic groups. A list of possible side chains of amino acids known in the art are described in Stryer, Biochemistry, 1981, published by W.H. Freeman and Company. $R^1$ can be $C_1$ to $C_{30}$, saturated or unsaturated, straight or branched, substituted or unsubstituted alkyls; substituted or unsubstituted aromatic groups; or mixtures thereof.

The N-acyl amino acid compound may be selected from the group consisting of N-acyl Phenylalanine, N-acyl Tyrosine, their isomers, their salts, and derivatives thereof. The amino acid can be the D or L isomer or a mixture thereof. N-acyl Phenylalanine corresponds to the following formula:

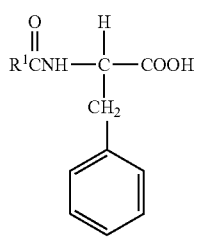

wherein $R^1$ can be $C_1$ to $C_{30}$, saturated or unsaturated, straight or branched, substituted or unsubstituted alkyls; substituted or unsubstituted aromatic groups; or mixtures thereof.

N-acyl Tyrosine corresponds to the following formula:

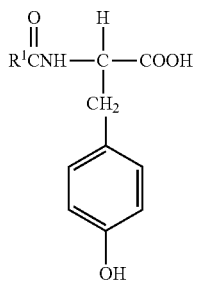

wherein $R^1$ can be $C_1$ to $C_{30}$, saturated or unsaturated, straight or branched, substituted or unsubstituted alkyls; substituted or unsubstituted aromatic groups; or mixtures thereof.

Particularly useful as a topical skin tone evening cosmetic agent is N-undecylenoyl-L-phenylalanine. This agent belongs to the broad class of N-acyl Phenylalanine derivatives, with its acyl group being a C11 mono-unsaturated fatty acid moiety and the amino acid being the L-isomer of phenylalanine. N-undecylenoyl-L-phenylalanine corresponds to the following formula:

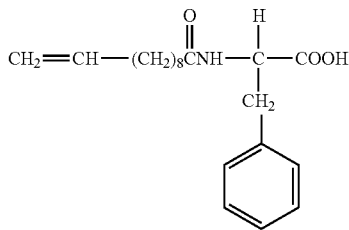

As used herein, N-undecylenoyl-L-phenylalanine is commercially available under the tradename Sepiwhite® from SEPPIC.

In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more N-acyl amino acids.

10. Retinoids

The personal care compositions may comprise one or more retinoid. In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more retinoids. The optimum concentration used in a composition will depend on the specific retinoid selected since their potency can vary considerably.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid may be selected from retinol, retinol esters (e.g., C2-C22 alkyl esters of retinol, including retinyl palmitate, retinyl acetate, retinyl propionate), retinal, and/or retinoic acid (including all-trans retinoic acid and/or 13-cis-retinoic acid), or mixtures thereof. Suitable retinoids which are described in U.S. Pat. Nos. 4,677,120; 4,885,311; 5,049, 584; 5,124,356; and Reissue 34,075. Other suitable retinoids may include tocopheryl-retinoate [tocopherol ester of retinoic acid (trans- or cis-), adapalene (6-[3-(1-adamantyl)-4-methoxyphenyl]-2-naphthoic acid}, and tazarotene (ethyl 6-[2-(4,4-dimethylthiochroman-6-yl)-ethynyl]nicotinate). Suitable retinoids include retinol, retinyl palmitate, retinyl acetate, retinyl propionate, retinal and combinations thereof. In selected embodiment, retinyl propionate may be used in amounts from about 0.1% to about 0.3%.

11. Peptides

The personal care composition may comprise a peptide. Suitable peptides can include, but are not limited to, di-, tri-, tetra-, penta-, and hexa-peptides and derivatives thereof. In one embodiment, the compositions comprise from about $1\times10^{-7}$% to about 20%, from about $1\times10^{-6}$% to about 10%, or from about $1\times10^{-5}$% to about 5%, by weight of a peptide. In one embodiment, the composition may comprise from about 0.0001%, 0.001%, 0.01%, 0.05%, 0.1%, 0.5%, or 1% to about 25%, 20%, 10%, 7%, 5%, 3%, by weight of the composition, of one or more peptides.

As used herein, "peptide" refers to peptides containing ten or fewer amino acids and their derivatives, isomers, and complexes with other species such as metal ions (e.g., copper, zinc, manganese, magnesium, and the like). Peptide refers to both naturally occurring and synthesized peptides. Also useful herein are naturally occurring and commercially available compositions that contain peptides. The peptides may contain at least one basic amino acid (e.g., histidine, lysine, arginine). For example, suitable peptides are the dipeptide carnosine (beta-ala-his), the tripeptide gly-his-lys, the tripeptide his-gly-gly, the tripeptide gly-gly-his, the tripeptide gly-his-gly, the tetrapeptide gly-gln-pro-arg, the pentapeptide lys-thr-thr-lys-ser, lipophilic derivatives of peptides, and metal complexes of the aforementioned (e.g., copper complex of the tripeptide his-gly-gly (also known as Iamin)). Other suitable peptides include Peptide CK (arg-lys-arg); Peptide CK+ (ac-arg-lys-arg-NH2); and Peptide E, arg-ser-arg-lys. A commercially available tripeptide derivative-containing composition is Biopeptide CL® (from Sederma, France), which contains 100 ppm of palmitoyl-gly-his-lys and is commercially available. A commercially available pentapeptide derivative-containing composition is Matrixyl® (from Sederma, France), which contains 100 ppm of palmitoyl-lys-thr-thr-lys-ser. A suitable peptide is a dipeptide based molecule having a C terminal amino acid of threonine, such as plamitoyl-lys-thr, as described in US Patent Application Publication 2007/0020220 A1.

Peptide derivatives useful herein include lipophilic derivatives such as palmitoyl derivatives. In one embodiment, the peptide is selected from palmitoyl-lys-thr-thr-lys-ser, palmitoyl-gly-his-lys, their derivatives, and combinations thereof.

12. Particulate Materials

The compositions of the present invention can comprise one or more particulate materials. Nonlimiting examples of particulate materials useful in the present invention include colored and uncolored pigments, interference pigments, inorganic powders, organic powders, composite powders, optical brightener particles, and combinations thereof. These particulates can, for instance, be platelet shaped, spherical, elongated or needle-shaped, or irregularly shaped, surface coated or uncoated, porous or non-porous, charged or uncharged, and can be added to the current compositions as a powder or as a pre-dispersion. In one embodiment, the composition may comprise from about 0.0001%, 0.001%, 0.01%, 0.05%, 0.1%, 0.5%, 1%, or 2% to about 50%, 25%, 20%, 10%, 7%, 5%, or 3% by weight of the composition, of particulate(s). There are no specific limitations as to the pigment, colorant or filler powders used in the composition.

Particulate materials useful herein can include, but are not limited to, bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, polyurethane, aluminum oxide, silicone resin, barium sulfate, calcium carbonate, cellulose acetate, PTFE, polymethyl methacrylate, starch, modified starches such as aluminum starch octenyl succinate, silk, glass, and mixtures thereof. Suitable commercial examples of particulates include, but are not limited, to polymeric particles chosen from the polymethylsilsesquioxane resin microspheres such as including materials sold under the tradename Tospearl® by Momentive Performance Materials Inc., microspheres of polymethylmethacrylates such Micropearl M305 by SEPPIC, spherical particles of crosslinked polydimethylsiloxanes, especially such as those sold by Dow Corning 9506 Cosmetic Power by Dow Corning, spherical particles of polyamide and more specifically Nylon 12 such as Orgasol® 2002 line by Atochem, polystyrene microspheres such as for example those sold under the name Dynospheres® by Dyno Particles, ethylene acrylate copolymer sold under the name EA209 by Kobo, PTFE, polypropylene, aluminum starch ocetenylsuccinate such as those sold under the name Dry-Flo® by AkzoNobel, microspheres of polyethylene such as those sold under the name of Microthene® FN510-00 by Equistar and under then name Micropoly by Presperse, Inc., silicone resin, polymethylsilsesquioxane silicone polymer, and mixtures thereof. Suitable particulate materials include spherical powders with an average primary particle size of from about 0.1 to about 75 microns or from about 0.2 to about 30 microns.

Other suitable particulate materials include interference pigments. Interference pigments, for purposes of the present specification, are defined as thin platelike layered particles having two or more layers of controlled thickness with different refractive indices that yield a characteristic reflected color from the interference of typically two, but occasionally more, light reflections, from different layers of the platelike particle. The most common examples of interference pigments are micas layered with about 50-300 nm films of TiO2, Fe2O3, silica, tin oxide, and/or Cr2O3. Such pigments are often pearlescent. Pearl pigments reflect, refract and transmit light because of the transparency of pigment particles and the large difference in the refractive index of mica platelets and, for example, the titanium dioxide coating. Useful interference pigments are available commercially from a wide variety of suppliers, for example, Rona (Timiron™ and Dichrona™), Presperse (Flonac™), Englehard (Duochrome™), Kobo (KTZ Interfine and KTZ Interval), BASF (Reflecks™) and Eckart (Prestige series). Suitable interference pigments may have a small particle sizes, with an average diameter of individual particles less than about 75 microns in the longest direction, or less than about 50 microns.

Other particulate materials include pigments which can provide color to the personal care composition. Suitable pigments include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example TiO2, ZnO, or ZrO2, are commercially available from a number of sources. One example of a suitable particulate material contains the material available from U.S. Cosmetics (TRONOX TiO2 series, SAT-T CR837, a rutile TiO2). Suitable pigments include charged dispersions of titanium dioxide, as are disclosed in U.S. Pat. No. 5,997,887.

Colored or uncolored pigments may have a primary average particle size of from about 10 nm, 15 nm, or 20 nm to about 100,000 nm, 5,000 nm, or 1000 nm. Mixtures of the same or different pigments having different particle sizes are also useful herein (e.g., incorporating a TiO$_2$ having a primary particle size of from about 100 nm to about 400 nm with a TiO$_2$ having a primary particle size of from about 10 nm to about 50 nm).

The particulate materials can be surface treated to provide added stability and/or for ease of formulation. Non-limiting examples of suitable coating materials include silicones, lecithin, amino acids, metal soaps, polyethylene and collagen. These surface treatments may be hydrophobic or hydrophilic. Particularly useful hydrophobic pigment treatments include polysiloxane treatments such as those disclosed in U.S. Pat. No. 5,143,722.

13. UV Actives

The compositions of the subject invention may optionally contain a UV active. As used herein, "UV active" includes both sunscreen agents and physical sunblocks. Suitable UV actives may be organic or inorganic. Suitable UV actives are listed in the functional category of "Sunscreen Agents" in the Personal Care Product Council's *International Cosmetic Ingredient Dictionary and Handbook*, Thirteenth Edition, 2010.

Suitable UV actives include dibenzoylmethane derivatives including 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxy dibenzoylmethane, 4-tert-butyl-4'-methoxy dibenzoylmethane (i.e., butyl methoxydibenzoylmethane or avobenzone)(commercially available as PARSOL® 1789 from DSM), 2-methyl-5-isopropyl-4'-methoxy dibenzoylmethane, 2-methyl-5-tert-butyl-4'-methoxydibenzoylmethane, 2,4-dimethyl-4'-methoxy dibenzoylmethane, and 2,6-dimethyl-4-tert-butyl-4'-methoxy dibenzoylmethane. Other suitable UV actives include 2-ethylhexyl-p-methoxycinnamate (commercially available as PARSOL® MCX from DSM), 2-hydroxy-4-methoxybenzophenone, benzophenone-3 (i.e., oxybeznone), octyldimethyl-p-aminobenzoic acid, digalloyltrioleate, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexyl-salicylate, glyceryl-p-aminobenzoate, 3,3,5-trimethylcyclohexylsalicylate, methylanthranilate, p-dimethylaminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, zinc oxide, titanium dioxide, and mixtures of these compounds.

Particularly suitable UV actives useful in the compositions of the present invention are 2-ethylhexyl-p-methoxycinnamate, 4-tert-butyl-4'-methoxy dibenzoylmethane, 2-hydroxy-4-methoxybenzo-phenone, 2-phenylbenzimidazole-5-sulfonic acid, octocrylene, zinc oxide, titanium dioxide, and mixtures thereof.

Other suitable UV actives include 4-methylbenzylidene camphor (commercially available as PARSOL® 5000 from DSM or Eusolex 6300 from Merck), methylene bis-benzotriazolyl tetramethylbutylphenol (i.e., bisoctrizole, commercially available as Tinosorb® M from BASF), bis-ethylhexyloxyphenol methoxyphenol triazine (i.e., bemotrizinol, commercially available as Tinosorb® S from BASF), disodium phenyl dibenzimidazole tetrasulfonate (i.e., Bisdisulizole disodium, commercially available as Neo Heliopan® AP from Symrise), Ethylhexyl triazone (commercially available as Uvinul® T 150 from BASF), Drometrizole trisiloxane (marketed as Mexoryl XL by L'Oreal), Sodium Dihydroxy Dimethoxy Disulfobenzophenone (i.e., benzophenone-9, commercially available as Uvinul® DS 49 from BASF), Diethylamino Hydroxybenzoyl Hexyl Benzoate (commercially available as Uvinul® A Plus from BASF), diethylhexyl butamido triazone (i.e., Iscotrizinol, commercially available as Uvasorb® HEB by 3V Sigma), Polysilicone-15 (i.e., commercially available as PARSOL® SLX from DSM), and Isoamyl p-Methoxycinnamate (i.e., amiloxate, commercially available as Neo Heliopan® E 1000 from Symrise).

14. Photostabilizers

A suitable photostabilizer is alpha-cyanodiphenylacrylate is as disclosed in U.S. Pat. No. 7,713,519. The alpha-cyanodiphenylacrylate may have the general formula:

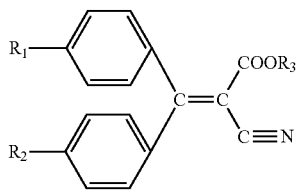

wherein one or both of R1 and R2 is independently a straight or branched chain C1-30 alkoxy radical and any non-alkoxy R1 or R2 radical is hydrogen; and R3 is a straight or branched chain C1-30 alkyl. Alternately, one or both of R1 and R2 is independently a C1-8 alkoxy radical and any non-alkoxy R1 or R2 radical is hydrogen; and R3 is a straight of branched chain C2-20 alkyl. Alternately, one or both of R1 and R2 is independently methoxy, and any non-methoxy R1 or R2 is hydrogen; and R3 is a straight or branched chain C2-20 alkyl.

A suitable alpha-cyanodiphenylacrylate is ethylhexyl methoxycrylene, or 2-ethylhexyl 2-cyano-3-(4-methoxyphenyl)-3-phenylpropenoate, wherein $R^1$ is methoxy, $R^2$ is hydrogen, and $R^3$ is 2-ethylhexyl. This material is available from Hallstar Company under trade name Solastay® S1.

Another suitable photostabilizer includes diesters or polyesters of naphthalene dicarboxylic acid as disclosed in U.S. Pat. Nos. 5,993,789, 6,113,931, 6,126,925 and 6,284,916. Suitable diesters or polyesters of naphthalene dicarboxylic acid may have the following formula:

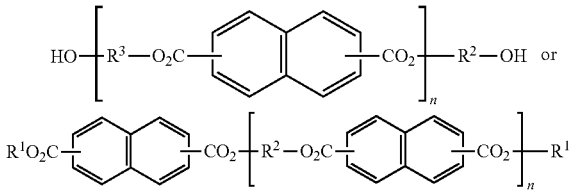

wherein each $R^1$ independently is an alkyl group having 1 to 22 carbon atoms, or a diol having the formula HO—$R^2$—OH, or a polyglycol having the formula HO—$R^3$—(—O—$R^2$—)$_m$—OH, and, wherein $R^2$ and $R^3$, same or different, are each an alkylene group, straight chain or branched, having 1 to 6 carbon atoms, wherein m and n are each 1 to about 100, 1 to about 10, or 2 to about 7. A suitable diesters of naphthalene dicarboxylic acid is diethylhexyl 2,6-naphthalate available as Corapan® TQ from Symrise.

Another suitable photostabilizer is 4-hydroxybenzylidenemalonate derivatives or 4-hydroxycinnamate derivatives. Suitable materials may have the following formula:

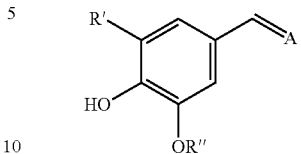

wherein A is a chromophoric group that absorbs UV-radiation, comprises one divalent group or two monovalent groups with at least one group having carbonyl (C=O) functionality; R' is hydrogen, a linear or branched $C_1$-$C_8$ alkyl radical or a linear or branched $C_1$-$C_8$ alkoxy radical; and R" is a linear or branched $C_1$-$C_8$ alkyl radical. Exemplary compounds include ethyl-alpha-cyano-3,5-dimethoxy-4-hydroxy cinnamate, ethyl-alpha-acetyl-3,5-dimethoxy-4-hydroxy cinnamate, iso-propyl-alpha-acetyl-3,5-dimethoxy-4-hydroxy cinnamate, iso-amyl-alpha-acetyl-3,5-dimethoxy-4-hydroxy cinnamate, 2-ethylhexyl-alpha-acetyl-3,5-dimethoxy-4-hydroxy cinnamate, diethyl-3,5-dimethoxy-4-hydroxy benzylidene malonate, di-(2-ethylhexyl)-3,5-dimethoxy-4-hydroxy benzylidene malonate, diisoamyl-3,5-dimethoxy-4-hydroxy benzylidene malonate, didodecyl-3,5-dimethoxy-4-hydroxy benzylidene malonate, dipalmitoyl-3,5-dimethoxy-4-hydroxy benzylidene malonate, and di-isopropyl-3,5-dimethoxy-4-hydroxy benzylidene malonate. A particularly suitable compound is diethylhexyl syringylidenemalonate (INCI name) available under the tradename Oxynex® ST from EMD Chemicals, Inc., having the formula:

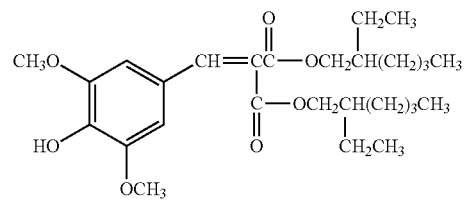

Additional suitable 4-hydroxybenzylidenemalonate derivatives or 4-hydroxycinnamate derivatives are disclosed in U.S. Pat. No. 7,357,919 and U.S. Patent Application Publication No. 2003/0108492A1 and US2003/0157035A.

Another suitable photostabilizer is a 2-pyrrolidinone-4-carboxy ester compounds. Suitable 2-pyrrolidinone-4-carboxy ester compounds may have the following formula:

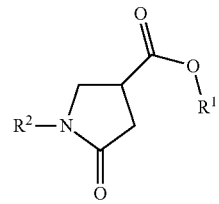

wherein $R^1$ is a linear or branched $C_1$-$C_{20}$ alkyl radical, and $R^2$ is a linear or branched $C_1$-$C_{20}$ alkyl radical which can contain a $C_5$-$C_6$ ring, the phenyl radical, the benzyl radical or the phenethyl radical. Exemplary radicals for $R^1$ and $R^2$ include methyl, ethyl, n-propyl, isopropyl, n-butyl, isobutyl, tert-butyl, n-octyl, 2-ethylhexyl, dodecyl, hexadecyl, cyclohexyl and methylcyclohexyl radicals. Particular examples of 2-pyrrolidinone-4-carboxy ester compounds are provided in U.S. Patent Application Publication No. 2010/0183529.

Other suitable photostabilizers include:
- silicon-containing s-triazines substituted with two aminobenzoate or aminobenzamide groups as described in U.S. Patent Application Publication No. 2008/0145324;
- fluorene derivatives as described in U.S. Patent Application Publications Nos. 2004/00579912, 2004/00579914, 200/00579916, and 2004/062726;
- piperidinol salts as described in U.S. Patent Application Publications No. 2005/0220727 including tris(tetramethylhydroxypiperidinol) citrate sold under the tradename Tinogard® Q by Ciba; and
- arylalkyl amides and esters as described in U.S. Patent Application Publication No. 2008/0019930.

Other suitable photostabilizers are listed in the functional category of "Light Stabilizers" in the Personal Care Product Council's *International Cosmetic Ingredient Dictionary and Handbook*, Thirteenth Edition, 2010.

In one embodiment, the composition may comprise from about 0.0001%, 0.001%, 0.01%, 0.05%, 0.1%, 0.5%, or 1% to about 30%, 25%, 20%, 10%, 7%, or 5%, by weight of the composition, of one or more suitable photostabilizer. In certain embodiments, the personal care composition may comprise at least one photostabilizer and at least one UV active. In particular embodiments, the UV active is a dibenzoylmethane derivative. In a particular embodiment, the UV active is 4,4'-t-butyl methoxydibenzoyl-methane (i.e., avobenzone).

15. Anti-Cellulite Agents

The compositions of the present invention may also comprise an anti-cellulite agent. Suitable agents may include, but are not limited to, xanthine compounds (e.g., caffeine, theophylline, theobromine, aminophylline, chloroethyltheophylline, dyphylline, etamiphylline, proxyphylline, and the like); extracts of tea, coffee, guarana, mate, cola (*Cola nitida*); extracts of climbing ivy (*Hedera helix*), arnica (*Arnica montana* L), rosemary (*Rosmarinus officinalis* N), of marigold (*Calendula officinalis*), sage (*Salvia officinalis* L), ginseng (*Panax ginseng*), St. John's wort (*Hypericum perforatum*), of butcher's broom (*Ruscus aculeatus* L), meadowsweet (*Filipendula ulmaria* L), orthosiphon (*Orthosiphon stamincus* benth), birch (*Betula alba*), cecropia and argan tree; *Ginkgo biloba*, horsetail, escin, cangzhu, *Chrysanthellum indicum*, *Dioscorea* plants rich in diosgenin or pure diosgenin or hecogenin and compounds thereof, *Ballota, Guioa, Davallia, Terminalia, Barringtonia, Trema, Antirobia*, bitter orange (*Citrus aurantium*); and an extract of cocoa bean shells (*Theobroma cacao*) such as sold under the name Caobromine® by Solabia.

In one embodiment, the personal care composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more anti-cellulite agents.

16. Desquamation Actives

A desquamation active may be added to the compositions of the present invention. In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more desquamation actives.

Suitable desquamation actives include beta-hydroxy acids such as salicylic acid and its derivatives (including 5-(noctanoyl)salicylic acid also known as capryloyl salicylic acid) and alpha-hydroxy acids such as glycolic acid, citric acid, lactic acid, tartaric acid, malic acid or mandelic acid; 8-hexadecene-1,16-dicarboxylic acid or 9-octadecenedioic acid; urea; gentisic acid; oligofucoses; cinnamic acid; Saphora Japonica extract; and resveratrol.

Other suitable desquamation actives include compounds acting on the enzymes involved in desquamating or degrading the corneodesmosomes, glycosidases, stratum corneum chymotryptic enzyme (SCCE) or other proteases (trypsin, chymotrypsin-like). Suitable materials include aminosulphonic compounds such as 4-(2-hydroxyethyl)piperazine-1-propanesulphonic acid (HEPES); 2-oxothiazolidine-4-carboxylic acid (procysteine) and its compounds; compounds of glycine-type alpha-amino acids (as described in U.S. Patent Application Publication No. 2002/0041889, and also sodium methylglycinediacetate sold under the trade name TRILON® M by BASF); honey; and sugar compounds such as O-octanoyl-6-D-maltose and N-acetylglucosamine.

One desquamation system comprises salicylic acid and zwitterionic surfactants as described in U.S. Pat. No. 5,652,228. Another desquamation system contains sulfhydryl compounds and zwitterionic surfactants as described in U.S. Pat. No. 5,681,852

17. Anti-Acne Actives

The compositions of the present invention can comprise one or more anti-acne actives. Suitable anti-acne actives include, but are not limited to, resorcinol, sulfur, salicylic acid, retinoids such as retinoic acid and its derivatives, sulfur-containing amino acids and their derivatives and salts (e.g., N-acetyl derivatives such as N-acetyl-L-cysteine), and lipoic acid. Other suitable anti-acne actives may be chosen from (i) antibiotics and antimicrobials such as benzoyl peroxide, octopirox, tetracycline, 2,4,4'trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; (ii) sebostats such as flavonoids; and (iii) bile salts such as scymnol sulfate and its derivatives, deoxycholate, and cholate. Further examples of suitable anti-acne actives are described in U.S. Pat. No. 5,607,980.

In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more anti-acne compounds.

18. Anti-Oxidants/Racial Scavengers

The compositions of the present invention can include an anti-oxidant/radical scavenger. In one embodiment, the composition may comprise from about 0.0001%, 0.001%, 0.01%, 0.05%, 0.1%, 0.5%, or 1% to about 30%, 25%, 20%, 10%, 7%, 5%, or 3%, by weight of the composition, of one or more anti-oxidant/radical scavengers.

Suitable anti-oxidants are listed in the functional category of "Antioxidants" in the Personal Care Product Council's *International Cosmetic Ingredient Dictionary and Handbook*, Thirteenth Edition, 2010.

Suitable anti-oxidants include butylated hydroxytoluene (BHT) and butylated hydroxyanisole (BHA). BHT can be described by the general formula:

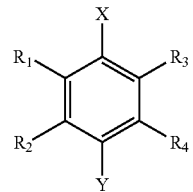

wherein X is OH or SH;

Y is selected from the group consisting of H, OH, $OR_5$, $COOR_5$, alkyl, cycloalkyl, heteroalkyl, heterocycloalkyl, aromatic, heteroaromatic, carboxamido, sulfonamido, carbamate, urea, and trialkylsilyl;

$R_1, R_2, R_3, R_4$ are selected from the group consisting of alkyl, cycloalkyl, heteroalkyl, heterocycloalkyl, aromatic, heteroaromatic, $OR_5$, carboxamido, sulfonamido, formyl, acyl, carboxyl, carboxylate, carbamate, urea, trialkylsilyl, hydroxyl, and hydrogen;

$R_5$ is selected from the group consisting of alkyl, cycloalkyl, heteroalkyl, heterocycloalkyl, aromatic, heteroaromatic, trialkylsilyl, acyl, and hydrogen.

Other anti-oxidants/radical scavengers such as ascorbic acid (vitamin C), tocopherol (vitamin E), tocopherol sorbate, tocopherol acetate, other esters of tocopherol, 6-hydroxy-2,5,7,8-tetramethylchroman-2-carboxylic acid (commercially available under the tradename Trolox®), amines (e.g., N,N'-diethylhydroxylamine, amino-guanidine), nordihydroguaiaretic acid, bioflavonoids, amino acids, silymarin, sorbic acids and its salts, lipoic acid, olive extracts, green tea extracts, white tea extracts, black tea extracts, polyphenols such as proanthocyanidine from pine bark, carotenoids, curcumin compounds such as tetrahydrocurcumin, OCTA (L-2-oxo-4-thiazolidine carboxylic acid), glutathione, and grape skin/seed extracts may be used. Suitable anti-oxidants/radical scavengers can be selected from esters of tocopherol such as tocopherol acetate.

In one embodiment, the composition comprises tocopherol sorbate. As used herein, "tocopherol sorbate" refers to the sorbic acid ester of tocopherol, a detailed description of which can be found in issued U.S. Pat. No. 5,922,758. In one embodiment, the composition may comprise from about 0.0001%, 0.001%, 0.01%, 0.05%, 0.1%, 0.5%, or 1% to about 50%, 25%, 20%, 10%, 7%, or 5%, by weight of the composition, of the tocopherol sorbate.

19. Conditioning Agents

The personal care compositions of the present invention can contain a safe and effective amount of a conditioning agent selected from, for example, humectants, moisturizers, occlusives, and emollients which may be applied to keratinous tissue. In one embodiment, the composition may comprise from about 0.0001%, 0.001%, 0.01%, 0.05%, 0.1%, 0.5%, or 1% to about 50%, 25%, 20%, 10%, 7%, or 5%, by weight of the composition, of one or more conditioning agents.

Humectants are one group of conditioning agents. Humectants can be selected from the group consisting of polyhydric alcohols, water soluble alkoxylated nonionic polymers, and mixtures thereof. Polyhydric alcohols useful herein include glycerin, sorbitol, propylene glycol, butylene glycol, pentylene glycol, hexylene glycol, ethoxylated glucose, 1,2-hexane diol, hexanetriol, dipropylene glycol, erythritol, trehalose, diglycerin, xylitol, maltitol, maltose, glucose, fructose, sodium chondroitin sulfate, sodium hyaluronate, hyaluronic acid, sodium adenosine phosphate, sodium lactate, pyrrolidone carbonate, glucosamine, cyclodextrin, and mixtures thereof.

Other conditioning agents include water soluble alkoxylated nonionic polymers such as polyethylene glycols and polypropylene glycols having a molecular weight of up to about 1000 such as those with CTFA names PEG-200, PEG-400, PEG-600, PEG-1000, and mixtures thereof.

Other conditioning agents include, but are not limited to, guanidine, urea, glycolic acid, glycolate salts (e.g. ammonium and quaternary alkyl ammonium), salicylic acid, lactic acid, lactate salts (e.g., ammonium and quaternary alkyl ammonium), aloe vera in any of its variety of forms (e.g., aloe vera gel), polyethylene glycols, sugars (e.g., melibiose), cellulose, dextrin, starches, sugar and starch derivatives (e.g., alkoxylated glucose, fucose), lactamide monoethanolamine, acetamide monoethanolamine, panthenol, allantoin, amylose, hyaluronic acid, sodium hyaluronate, betaglucan, glycogen, alguronic acid, galactoarabinan and mixtures thereof.

Other conditioning agents are extracts that contain polysaccharides including the following materials: TriMoist KMF (Mibelle AG Biochemistry), Fucogel® and Glycofilm® (Solabia Group), Aquaxyl™ (Seppic), Pheohydrane P (Barnet Products Corporation), Aesthigel (Barnet Products Corporation), Pentacare HP (Pentapharm), and Hyalurosmooth (Laboratories Serobiologiques).

Also useful herein are the propoxylated glycerols described in U.S. Pat. No. 4,976,953. Also useful are various $C_1$-$C_{30}$ monoesters and polyesters of sugars and related materials. These esters are derived from a sugar or polyol moiety and one or more carboxylic acid moieties. Other suitable conditioning agents are described in U.S. Pat. Nos. 5,750,122; 5,674,478; 4,529,586; 4,507,280; 4,663,158; 4,197,865; 4,217,914; 4,381,919: and 4,422,853.

20. Anti-Inflammatory Agents

Steroidal anti-inflammatory agents can include, but are not limited to, corticosteroids such as hydrocortisone. In addition, nonsteroidal anti-inflammatory agents can be useful herein. The varieties of compounds encompassed by this group are well known to those skilled in the art. Specific non-steroidal anti-inflammatory agents that can be useful in the composition of the present invention include, but are not limited to, salicylates, flufenamic acid, etofenamate, aspirin, and mixtures thereof.

Additional anti-inflammatory agents useful herein include allantoin and compounds of the Licorice (the plant genus/species *Glycyrrhiza glabra*) family, including glycyrrhetic acid, glycyrrhizic acid, and derivatives thereof (e.g., salts and esters).

In one embodiment, the composition may comprises from about 0.0001%, 0.001%, 0.01%, 0.05%, 0.1%, 0.5%, or 1% to about 50%, 25%, 20%, 10%, 7%, or 5%, by weight of the composition, of one or more anti-inflammatory agents.

21. Tanning Actives

The compositions of the present invention can comprise a tanning active. In one embodiment, the composition may comprises from about 0.0001%, 0.001%, 0.01%, 0.05%, 0.1%, 0.5%, or 1% to about 50%, 25%, 20%, 10%, 7%, or 5%, by weight of the composition, of a tanning active. A suitable tanning active is dihydroxyacetone.

22. Skin Lightening Agents

The compositions of the present invention can comprise a skin lightening agent. In one embodiment, the composition may comprises from about 0.0001%, 0.001%, 0.01%, 0.05%, 0.1%, 0.5%, or 1% to about 50%, 25%, 20%, 10%, 7%, or 5%, by weight of the composition, of one or more skin lightening agents. Suitable skin lightening agents include those known in the art, including ascorbyl glucoside, kojic acid, hydroquinone arbutin, and tranexamic acid. Other skin lightening materials suitable for use herein can include Acitwhite® (Cognis), Emblica®(Rona), Azeloglicina (Sinerga) and extracts (e.g. mulberry extract). An exemplary skin lightening agent is ascorbyl glucoside. Other skin lightening actives include Phlorogine and Phlorgine BG (*laminaria saccharina* extract), deoxyarbutin, sucrose dilaurate, bakuchiol, pyrenoine, millet, arlatone dioic acid, cinnamic acid, ferulic acid, achromaxyl, methyl nicotinamide, oil soluble licorice extract, folic acid, undecylenic acid, zinc undecylenate, L-tryptophan, thiamine HCl, hexylresorcinol, lipidami red vine, dragosine, methyl gentisate, inositol, 1,2-hexandiol and 1,2-octandiol (available as Symdiol 68 from Symrise), laminaine, their salts, their derivatives, their precursors, and combinations thereof. Suitable skin lightening agents are further disclosed in U.S. Patent Application Publication US 2010/0189669 A1.

23. Botanical Extracts

The personal care composition may comprise botanical extracts. In one embodiment, the composition may comprises from about 0.0001%, 0.0005% 0.001%, 0.01%, 0.05%, 0.1%, 0.5%, or 1% to about 30%, 25%, 20%, 10%, 7%, 5%, 3%, by weight of the composition, of one or more botanical extracts. Suitable botanical extracts include extracts from plants (herbs, roots, flowers, fruits, seeds) such as flowers, fruits, vegetables, and so on, including yeast ferment extract, *Padina Pavonica* extract, *thermus thermophilis* ferment extract, *camelina sativa* seed oil, *boswellia serrata* extract, olive extract, *bodopsis Thaliana* extract, *Acacia Dealbata* extract, *Acer Saccharinum* (sugar maple), *acidophilus*, acorns, aesculus, *Alicaligenes* polysaccharides, agaricus, agave, agrimonia, algae, aloe, *citrus*, brassica, cinnamon, orange, apple, blueberry, cranberry, peach, pear, lemon, lime, pea, seaweed, caffeine, green tea, chamomile, willowbark, mulberry, poppy, and the like. Further specific examples include, but are not limited to, *Glycyrrhiza Glabra, Salix Nigra, Macrocycstis Pyrifera, Pyrus Malus, Saxifraga Sarmentosa, Vitis Vinifera, Morus Nigra, Scutellaria Baicalensis, Anthemis Nobilis, Salvia Sclarea, Rosmarinus Officianalis, Citrus Medica Limonum, Ginkgo Biloba Panax Ginseng, Siegesbeckia Orientalis, Fructus Mume, Ascophyllum Nodosum, Bifida Ferment lysate, Glycine Soja* extract, *Beta Vulgaris, Haberlea Rhodopensis, Polygonum Cuspidatum, Citrus Aurantium Dulcis, Vitis Vinifera, Selaginella Tamariscina, Humulus Lupulus, Citrus Reticulata Peel, Punica Granatum, Asparagopsis, Curcuma Longa, Menyanthes Trifoliata, Helianthus Annuus, Hordeum Vulgare, Cucumis Sativus, Evernia Prunastri, Evernia Furfuracea, Laminaria Angustata, Laminaria Cloustoni, Laminaria Digitata, Laminaria Digitata, Laminaria Hyperborea, Laminaria Japonica, Laminaria Longissima, Laminaria Ochotensis, Laminaria Ochroleuca, Laminaria Saccharina*, and mixtures thereof. Other suitable actives are listed in the functional category of "Biological Products" in the Personal Care Product Council's *International Cosmetic Ingredient Dictionary and Handbook*, Thirteenth Edition, 2010.

24. Antimicrobial, Antibacterial and Antifungal Actives

The personal care compositions can comprise an antimicrobial or antifungal active. A safe and effective amount of an antimicrobial or antifungal active can be added to the present compositions. In one embodiment, the composition may comprises from about 0.0001%, 0.001%, 0.01%, 0.05%, 0.1%, 0.5%, or 1% to about 30%, 25%, 20%, 10%, 7%, 5%, or 3%, by weight of the composition, of one or more antimicrobial, antibacterial and/or antifungal actives.

Suitable actives useful herein include those selected from the group consisting of benzoyl peroxide, 3-hydroxy benzoic acid, glycolic acid, lactic acid, 4-hydroxy benzoic acid, 2-hydroxybutanoic acid, 2-hydroxypentanoic acid, 2-hydroxyhexanoic acid, phytic acid, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, lidocaine hydrochloride, neocycin sulfate, and mixtures thereof.

Suitable antimicrobial actives include coal tar, sulfur, whitfield's ointment, castellani's paint, aluminum chloride, gentian violet, octopirox (piroctone olamine), 2,4,4'-trichloro-2'-hydroxy diphenyl ether (Triclosan), 3,4,4'-trichlorocarbanilide (Triclocarban), ciclopirox olamine, undecylenic acid and metal salts, potassium permanganate, selenium sulfide, sodium thiosulfate, propylene glycol, oil of bitter orange, urea preparations, griseofulvin, 8-Hydroxyquinoline ciloquinol, thiobendazole, thiocarbamates, haloprogin, polyenes, hydroxypyridone, morpholine, benzylamine, allylamines (such as terbinafine), tea tree oil, clove leaf oil, coriander, palmarosa, berberine, thyme red, cinnamon oil, cinnamic aldehyde, citronellic acid, hinokitol, ichthyol pale, ethylhexylglycerin, hexamidine diisethionate, azelaic acid, lyticase, iodopropynyl butylcarbamate (IPBC), isothiazalinones such as octyl isothiazalinone, and combinations thereof.

Azole antimicrobials may be used and include imidazoles such as benzimidazole, benzothiazole, bifonazole, butaconazole nitrate, climbazole, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, tioconazole, thiazole, and triazoles such as terconazole and itraconazole, and combinations thereof.

Selenium sulfide may be used as an antimicrobial. Selenium sulfide is generally regarded as a compound having one mole of selenium and two moles of sulfur, although it may also be a cyclic formula that conforms to the general formula $Se_xS_y$, wherein $x+y=8$. Average particle diameters for the selenium sulfide are typically less than 15 µm, as measured by forward laser light scattering device (e.g., Malvern 3600 instrument), or, alternately, less than 10 µm. Selenium sulfide compounds are described, for example, in U.S. Pat. Nos. 2,694,668, 3,152,046, 4,089,945, and 4,885,107.

Other suitable actives are listed in the functional category of "Cosmetic Biocides" in the Personal Care Product Council's *International Cosmetic Ingredient Dictionary and Handbook*, Thirteenth Edition, 2010.

25. Antiperspirant Actives

Antiperspirant actives may also be included in the compositions of the present invention. Suitable antiperspirant actives include astringent metallic salts, especially the inorganic and organic salts of aluminum zirconium and zinc, as well as mixtures thereof. Exemplary actives include aluminum containing and/or zirconium-containing materials or salts, such as aluminum halides, aluminum chlorohydrate, aluminum hydroxyhalides, zirconyl oxyhalides, zirconyl hydroxyhalides, and mixtures thereof. In one embodiment, the composition may comprises from about 0.0001%, 0.001%, 0.01%, 0.05%, 0.1%, 0.5%, or 1% to about 30%, 25%, 20%, 10%, 7%, 5%, or 3% by weight of the composition, of one or more antiperspirant compounds.

26. Sensates

The personal care composition may include a warming sensates and/or cooling senate. Sensates provide the sensation of heating or cooling to a user, but may or may not yield a change in skin temperature. The sensation may be instantaneous or may be delayed, but, generally, is appreciable within 5 minutes of application of the skin care composition. In one embodiment, the composition may comprises from about 0.0001%, 0.001%, 0.01%, 0.05%, 0.1%, 0.5%, or 1% to about 30%, 25%, 20%, 10%, 7%, 5%, or 3%, by weight of the composition, of one or more sensates. Any mixture of the warming and/or cooling sensates may also be used.

Suitable warming sensates include vanillyl alcohol derivatives including of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether and vanillyl alcohol ethyl ether; and phosphate derivatives comprising the aforementioned vanillyl alcohol derivatives such as vanillyl alcohol isoamyl ether monophosphate, vanillyl alcohol n-butyl ether monophosphate, vanillyl alcohol n-hexyl ether monophosphate. Other suitable warming sensates include ethyl alcohol, niacin, jambu, nicotinic acid, zingerone, vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, methyl salicylate, shogaol paradol, zingerone, capsaicin, dihydrocapsaicin, nordihydrocapsaicin, homocapsaicin, homodihydrocapsaicin, ethanol, tincture capsicum, oleoresin ginger alcohol extraction, eucalyptus oil, capsaicin, cinnamic aldehyde, chloroform, ether, iso-Amyl alcohol, benzyl alcohol, allyl isothiocyanate, ethyl acetate, glycerine, limonene, menthol, 4-hydroxy-4-methyl-cyclohexen-2-one-1, and mixtures thereof. Further suitable warming sensates include fluid extracts, hydro-alcohol extracts, essential oils, oleoresins, concretes or distillates of mustard seed, ginger, horseradish, chilies, jalapeno, pepper, capsicum, clove, cassia, and mixtures thereof.

Suitable cooling sensates include menthol, isopulegole, 3-(1-menthoxy)propan-1,2-diol, p-menthan-3,8-diol, 6-isopropyl-9-methyl-1,4-dioxaspiro-(4,5)-decane-2-methanol, menthyl succinate, alkaline earth salts of menthyl succinate, trimethyl cyclohexanol, N-ethyl-2-isopropyl-5-methylcyclohexane carboxamide and other carboxamides as described in U.S. Pat. Nos. 4,136,163 and 4,230,688, 3-(1-menthoxy)-2-methyl-propan-1,2-diol, mint oil, peppermint oil, wintergreen, menthone, menthone glycerin ketal and other glycerol ketals described in U.S. Pat. No. 5,266,592, menthyl lactate, 2-(5'-methyl-2-(methylethyl)cyclohexyloxy)ethan-1-ol, 3-(5'-methyl-2'-(methylethyl)cyclohexyloxy)propan-1-ol, 4-(5'-methyl-2'-(methylethyl)cyclohexyloxy)butan-1-ol, and spearmint. Other cooling sensates include p-menth-3-yl n-butyl sulphoxide, n-butyl 1-isobutylcyclohexyl sulphoxide, n-hexyl 1-isobutylcyclohexyl sulphoxide, n-butyl 1-isoamylcyclohexyl sulphoxide and n-hexyl 1,2-diethylcyclohexyl sulphoxide, and other cyclic sulphoxides and sulphones as described in U.S. Pat. No. 4,032,661.

27. Preservatives

In one embodiment, the composition may comprises from about 0.0001%, 0.001%, 0.01%, 0.05%, 0.1%, 0.5%, or 1% to about 10%, 7%, 5%, 2%, or 1%, by weight of the composition, of one or more preservatives. A variety of preservatives are suitable, including such as benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, sodium benzoate, calcium benzoate, calcium propionate, caprylyl glycol, biguanide derivatives, phenoxyethanol, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM hydantoin, DEDM hydantoin dilaurate, dehydroacetic acid, diazolidinyl urea, dibromopropamidine diisethionate, DMDM hydantoin, glyceryl caprylate, potassium sorbate, salicylic acid, hexamidine, capryloyl glycine, 1,2 hexanediol, undecylenoyl glycine, ethylhexylglycerin, caprylhydroxamic acid, methylpropanediol, hinokitiol, sodium hinokitiol, phenylethyl alcohol, levulinec acid, p-anisic acid, 2-bromo-2-nitropropane-1,3-diol, sodium hydroxymethylglycinate, iodopropynyl butylcarbamate, methylchloroisothiazolinone, methylisothiazolinone, piroctone olamine, cinnamon oil, rosemary extract, Biopein® (available form Bio-Botanica), Naticide® (available form Sinerga), and combinations thereof. In one embodiment, the composition is free of parabens and/or formaldehydes.

28. Anti-Dandruff Actives

The personal care compositions of the present invention may also contain an anti-dandruff agent. In one embodiment, the personal care composition may comprises from about 0.0001%, 0.001%, 0.01%, 0.05%, 0.1%, 0.5%, or 1% to about 20%, 10%, 7%, 5%, 4%, 3%, or 2%, by weight of the composition, of one or more anti-dandruff actives. Suitable, non-limiting examples of anti-dandruff particulates include: pyridinethione salts, azoles, selenium sulfide, particulate sulfur, and mixtures thereof. In a particular embodiment, pyridinethione anti-dandruff particulates, especially 1-hydroxy-2-pyridinethione salts, may be used. Suitable pyridinethione salts include those formed from heavy metals such as zinc, tin, cadmium, magnesium, aluminum and zirconium. In particular, zinc or a zinc salt of 1-hydroxy-2-pyridinethione (known as "zinc pyridinethione" or "ZPT") may be used. 1-hydroxy-2-pyridinethione salts may be in platelet particle form, wherein the particles have an average size of up to about 20μ, up to about 5μ, or up to about 2.5μ. Salts formed from other cations, such as sodium, may also be suitable. Pyridinethione anti-dandruff agents are described, for example, in U.S. Pat. Nos. 2,809,971; 3,236,733; 3,753,196; 3,761,418; 4,345,080; 4,323,683; 4,379,753; and 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

29. Substantivity Polymers

The personal care composition can comprise one or more substantivity polymers. These polymers may be used to enhance the deposition and longevity of other ingredients onto the keratinous tissue. These polymers may also improve rub-off resistance and water repellence. In one embodiment, the composition may comprises from about 0.0001%, 0.001%, 0.01%, 0.05%, 0.1%, 0.5%, or 1% to about 30%, 25%, 20%, 10%, 7%, 5%, or 3%, by weight of the composition, of one or more substantivity polymer.

Suitable cationic polymers for use in the compositions of the present invention contain cationic nitrogen-containing moieties such as quaternary ammonium or cationic protonated amino moieties. The cationic protonated amines can be primary, secondary, or tertiary amines (preferably secondary or tertiary), depending upon the particular species and the selected pH of the composition. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair product performance, stability or aesthetics. Non limiting examples of such counterions include halides (e.g., chloride, fluoride, bromide, iodide), sulfate and methylsulfate.

Non limiting examples of suitable cationic polymers include copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone.

Suitable cationic protonated amino and quaternary ammonium monomers, for inclusion in the cationic polymers of the composition herein, include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts.

Other suitable cationic polymers for use in the compositions include copolymers of 1-vinyl-2-pyrrolidone and 1-vinyl-3-methylimidazolium salt (e.g., chloride salt) (INCI name: Polyquaternium-16); copolymers of 1-vinyl-2-pyrrolidone and dimethylaminoethyl methacrylate (INCI name: Polyquaternium-11); cationic diallyl quaternary ammonium-containing polymers, including, for example, dimethyldiallylammonium chloride homopolymer, copolymers of acrylamide and dimethyldiallylammonium chloride (INCI name: Polyquaternium 6 and Polyquaternium 7, respectively); amphoteric copolymers of acrylic acid including copolymers of acrylic acid and dimethyldiallylammonium chloride (INCI name: Polyquaternium 22), terpolymers of acrylic acid with dimethyldiallylammonium chloride and acrylamide (INCI name: Polyquaternium 39), and terpolymers of acrylic acid with methacrylamidopropyl trimethylammonium chloride and methylacrylate (INCI name: Polyquaternium 47). Preferred cationic substituted monomers are the cationic substituted dialkylaminoalkyl acrylamides, dialkylaminoalkyl methacrylamides, and combinations thereof. These preferred monomers conform to the formula:

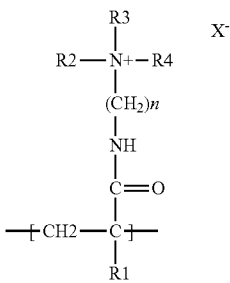

wherein $R^1$ is hydrogen, methyl or ethyl; each of $R^2$, $R^3$ and $R^4$ are independently hydrogen or a short chain alkyl having from about 1 to about 8 carbon atoms; n is an integer having a value of from about 1 to about 8; and X is a counterion. The nitrogen attached to $R^2$, $R^3$ and $R^4$ may be a protonated amine (primary, secondary or tertiary), but is preferably a quaternary ammonium wherein each of $R^2$, $R^3$ and $R^4$ are alkyl groups a non limiting example of which is polymethyacrylamidopropyl trimonium chloride, available under the trade name Polycare 133, from Rhone-Poulenc.

Other suitable cationic polymers for use in the composition include polysaccharide polymers, such as cationic cellulose derivatives and cationic starch derivatives. Suitable cationic polysaccharide polymers include those which conform to the formula:

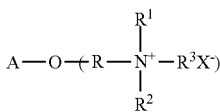

wherein A is an anhydroglucose residual group, such as a starch or cellulose anhydroglucose residual; R is an alkylene oxyalkylene, polyoxyalkylene, or hydroxyalkylene group, or combination thereof; R1, R2, and R3 independently are alkyl, aryl, alkylaryl, arylalkyl, alkoxyalkyl, or alkoxyaryl groups, each group containing up to about 18 carbon atoms; and X is an anionic counterion as described in hereinbefore.

Suitable cationic cellulose polymers are salts of hydroxyethyl cellulose reacted with trimethyl ammonium substituted epoxide, INCI name "Polyquaternium 10" and available from Amerchol Corp. (Edison, N.J., USA) in their Polymer LR, JR, and KG series of polymers. Other suitable types of cationic cellulose includes the polymeric quaternary ammonium salts of hydroxyethyl cellulose reacted with lauryl dimethyl ammonium-substituted epoxide, INCI name "Polyquaternium 24." These materials are available from Amerchol Corp. under the tradename Polymer LM-200.

Other suitable cationic polymers include cationic guar gum derivatives, such as guar hydroxypropyltrimonium chloride, specific examples of which include the Jaguar series commercially available from Rhone-Poulenc Incorporated and the N-Hance series commercially available from Aqualon Division of Hercules, Inc. Other suitable cationic polymers include quaternary nitrogen-containing cellulose ethers, some examples of which are described in U.S. Pat. No. 3,962,418. Other suitable cationic polymers include copolymers of etherified cellulose, guar and starch, some examples of which are described in U.S. Pat. No. 3,958,581.

The compositions herein can comprise nonionic polymers. For instance, polyalkylene glycols having a molecular weight of more than about 1000 can be used. These can include those having the following general formula:

wherein R is selected from the group consisting of H, methyl, and mixtures thereof; and n is a value selected such that the molecular weight of the molecule is greater than 1000 Da. Preferred polyethylene glycol polymers can include PEG-2M (also known as Polyox WSR® N-10, which is available from Dow Chemical Co. and as PEG-2,000); PEG-5M (also known as Polyox WSR® N-35 and Polyox WSR® N-80, available from Dow and as PEG-5,000 and Polyethylene Glycol 300,000); PEG-7M (also known as Polyox WSR® N-750 available from Dow); PEG-9M (also known as Polyox WSR® N-3333 available from Dow); and PEG-14 M (also known as Polyox WSR® N-3000 available from Dow).

Suitable commercially available substantivity polymers include: Cosmedia DC (hydrogenated dimer Dilinoleyl/Dimethylcarbonate Copolymer) available from Cognis; Polycrylene (copolymer of adipic acid and neopentyl glycol end-capped with either octyldodecanol or a cyanodiphenylpropenoyl group). Polycrylene has the INCI name Polyester-8 and is available from Hallstar Co; Dow Corning FA 4001 CM Silicone Acrylate and Dow Corning FA 4002 ID Silicone Acrylate (copolymer of polytrimethylsiloxymethacrylate and one or more monomers consisting of acrylic acid, methacrylic acid, or one of their simple esters dissolved in cyclopentasiloxane or isododecane, respectively); Ganex P-904 (poly(butylated vinylpyrrolidone)), Ganex V-216 (vinylpyrrolidone and hexadecene copolymer), Ganex V-220 (vinylpyrrolidone and eicosene copolymer), and Ganex WP-660 (vinyl pyrrolidone and 1-triacontane copolymer), all available from International Specialty Products; Phospholipon 90H (hydrogenated lecithin) available from Phospholipid GmbH; Dermacryl AQF (acrylates copolymer) available from National Starch and Chemical Company; Stantiv OMA-2 (octadecene and maleic anhydride copolymer) available from Vertellus Performance Materials, Inc.; Dermacryl-79 (copolymer of octylacrylamide and one or more monomers consisting of acrylic acid, methacrylic acid or one of their simple esters) available from National Starch and Chemical Company; Allianz OPT (copolymer of: methacrylic acid, methyl methacrylate, butyl acrylate, and cetyl-eicosinyl methacrylate) available from International Specialty Products; and Avalure UR 450 (PPG-17, isophorone diisocyanate and dimethylol propionic acid copolymer) available from Noveon.

Other suitable polymers are disclosed in paragraph 50 of U.S. Patent Application Publication No. 2006/0134045 A1.

30. Detersive Surfactants

Depending upon the form and function, the personal care composition may include one or more detersive surfactants. In certain embodiments, the personal care composition may be in the form of a leave-on product that may be substantially free of cleansing or detersive surfactants. For example, leave-on compositions may comprise less than 1% cleansing surfactants, less than 0.5% cleansing surfactants, or 0% cleansing surfactants If and when present, the detersive surfactant component can be included to provide cleaning performance to the composition. The detersive surfactant component in turn can comprise anionic detersive surfactant, zwitterionic or amphoteric detersive surfactant, or a combination thereof. Such surfactants should be physically and chemically compatible with the essential components described herein, or should not otherwise unduly impair product stability, aesthetics or performance.

Suitable anionic detersive surfactant components for use in the composition herein include those which are known for use in hair care or other personal care cleansing compositions. When included, the concentration of the anionic surfactant component in the composition can preferably be sufficient to provide the desired cleaning and lather performance, which generally can range from about 1%, 2.5%, 5%, 7.5%, 10%, 12.5%, or 15% to about 50%, 40%, 30%, 25%, 20%, or 10%, by weight of the composition.

Suitable anionic surfactants suitable for use in the compositions are the alkyl and alkyl ether sulfates. These materials have the respective formulae $ROSO_3M$ and $RO(C_2H_4O)_xSO_3M$, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium.

In certain embodiments, R has from about 8 to about 18 carbon atoms, from about 10 to about 16 carbon atoms, or from about 12 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Lauryl alcohol and straight chain alcohols derived from coconut oil or palm kernel oil are preferred. Such alcohols are reacted with between about 0 and about 10, from about 2 to about 5, or about 3, molar proportions of ethylene oxide, and the resulting mixture of molecular species having, for example, an average of 3 moles of ethylene oxide per mole of alcohol, is sulfated and neutralized.

Other suitable anionic detersive surfactants are the water-soluble salts of organic, sulfuric acid reaction products conforming to the formula $[R^1—SO_3-M]$ where $R^1$ is a straight or branched chain, saturated, aliphatic hydrocarbon radical having from about 8 to about 24 or from about 10 to about 18 carbon atoms; and M is a cation described hereinbefore.

Still other suitable anionic detersive surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921, 2,486,922, and 2,396,278.

Other anionic detersive surfactants suitable for use in the compositions are the succinates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic detersive surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic detersive surfactants suitable for use in the personal care composition is beta-alkyloxy alkane sulfonates. These surfactants conform to the formula

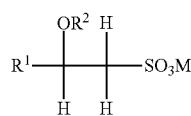

where $R^1$ is a straight chain alkyl group having from about 6 to about 20 carbon atoms, $R^2$ is a lower alkyl group having from about 1 to about 3 carbon atoms, preferably 1 carbon atom, and M is a water-soluble cation as described hereinbefore.

Suitable anionic detersive surfactants for use in the compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium cocoyl isethionate and combinations thereof.

Suitable amphoteric or zwitterionic detersive surfactants for use in the composition herein include those which are known for use in hair care or other personal care cleansing. Amphoteric detersive surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Preferred amphoteric detersive surfactants for use in the present invention include cocoamphoacetate, cocoamphodiacetate, lauroamphoacetate, lauroamphodiacetate, and mixtures thereof. Non limiting examples of suitable zwitterionic or amphoteric surfactants are described in U.S. Pat. Nos. 5,104,646 and 5,106,609.

Zwitterionic detersive surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Zwitterionics such as betaines are preferred.

Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. Non limiting examples of other anionic, zwitterionic, amphoteric or optional additional surfactants suitable for use in the compositions are described in McCutcheon's, *Emulsifiers and Detergents*, 2010 Annual Ed., published by M. C. Publishing Co., and U.S. Pat. Nos. 3,929,678, 2,658,072, 2,438,091, and 2,528,378.

Any other suitable optional component can also be included in the personal care composition of the present invention, such as those ingredients that are conventionally used in given product types. The Personal Care Product Council's *International Cosmetic Ingredient Dictionary and Handbook*, Thirteenth Edition, 2010, describes a wide variety of nonlimiting functional materials that can be added to the composition herein. Examples of these functional classes include, but are not limited to: abrasives, absorbents, fragrances, anti-acne agents, anti-caking agents, antifoaming agents, antimicrobial agents (e.g., iodopropyl butylcarbamate), antifungal agents, antioxidants, binders, buffering agents, bulking agents, chelating agents, colorants, cosmetic astringents, cosmetic biocides, denaturants, drug astringents, external analgesics, film formers, opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching agents, skin-conditioning agents (e.g. humectants and occlusive agents), and skin protectants. Other suitable optional person care ingredients include materials listed in paragraphs 513-839 of U.S. Patent Application No. 2010/0112100.

Exemplary Personal Care Composition

The following formulations are non-limiting prophetic examples of suitable person care compositions. Where applicable, ingredients are referenced by INCI name. While particular embodiments of the subject invention have been described, it will be obvious to those skilled in the art that various changes and modifications to the subject invention can be made without departing from the spirit and scope of the invention.

| (values are weight %) | Examples | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| PHASE A | | | | | | | | | | | | |
| DC-9040 *1 | 5.10 | 13.5 | | | q.s to 100 | | | | | | | |
| DC-9045 *2 | | | 15 | 15 | | | 32.75 | 14.0 | | 14.0 | | |
| PEG-4 | | | | | | | | | | | q.s to 100 | |
| Dimethicone | 4.10 | | 6 | 6 | | | | 5.2 | | 5.2 | | |
| Polymethylsilsesquioxane *3 | 4.10 | 7.5 | | | | | | | 0.5 | | | 0.5 |
| Polyethylene beads *4 | | | | | | | | | | 2.0 | 2.0 | |
| Cyclomethicone | 11.4 | 23.5 | 15 | 15 | | q.s to 100 | 10.0 | 1.05 | | 1.05 | | |
| KSG-210 *5 | 5.40 | 2.5 | | | | | | | | | | |
| KSG-310 *6 | | | | | 20.0 | | | | | | | |
| Polyethylene wax *7 | 2.05 | | | | | | | | | | | |
| DC-2503 Cosmetic Wax *8 | 3.77 | | | | | | 1.5 | | | | | |
| Abil EM97 *9 | | 0.45 | | | | | 0.45 | | | | | |
| KF 6017 *10 | | 0.375 | | | | | | | | | | |
| Cetyl Ricinoleate | | 0.25 | | | | | | | | | | |
| KTZ Fine TiO$_2$ coated Mica *11 | 1.00 | | | | | | | | | | | |
| Dow Corning 1503 *12 | | | 3 | 3 | | | | 3.5 | | 3.5 | | |
| Octisalate | | | | | 4.0 | 4.0 | | | | | | |
| Homosalate | | | | | 4.0 | 4.0 | | | | | | |
| Octocrylene | | | | | 1.5 | 1.5 | | | | | | |
| Avobenzene | | | | | 2.0 | 2.0 | | | | | | |
| Isopropyl Lauroylsarcosinate | | | | | 7.5 | 7.5 | | | | | | |
| Tospearl 145A *13 | | | | | 10 | 10 | | | | | | |
| Prestige Fire Red 11S2 *14 | | | | | 0.1 | 0.1 | | | | | | |
| Microthene FN-510 *15 | | | 9 | 9 | | | | 10.0 | | 10.0 | | |
| Petrolatum | | | | | | | 0.5 | | | | | |
| Isohexadecane | | | | | | | | | | 3.0 | | 3.0 |
| Isopropyl Isostearate | | | | | | | | | | 1.0 | | 1.0 |
| Stearic Acid | | | | | | | | | | 0.4 | | 0.4 |
| Cetearyl Glucoside | | | | | | | | | | 0.2 | 0.5 | 0.2 |
| Cetyl Alcohol | | | | | | | | | | 1.0 | 1.3 | 1.0 |
| Stearyl Alcohol | | | | | | | | | | | 20.0 | |
| Magnesium Sulfate Anhydrous | | | | | | | | | | | 3.0 | |
| PEG/PEG-300/55 Copolymer | | | | | | | | | | | 2.0 | |
| Tego Care CP *16 | | | | | | | | | | | 1.78 | |
| Econol TM-22 *17 | | | | | | | | | | | 0.80 | |
| Distearyldimonium chloride | | | | | | | | | | | 0.25 | |
| Hydroxypropylcellulose | | | | | | | | | | | | |
| Petrolatum | | | | | | | 0.5 | | | | 0.15 | |
| Fragrance | 0.10 | | | | 0.2 | 0.2 | | | | | | |
| PHASE B | | | | | | | | | | | | |
| Glycerin | | 10.0 | 10.0 | 11 | 11 | | 10 | 10.0 | 2.0 | 10.0 | | 2.0 |
| Panthenol | | 0.5 | 1.00 | 0.7 | 0.7 | | | 1.0 | 1.0 | | 1.0 | |
| Pentylene Glycol | | 3.00 | | | | | | | | | | |

-continued

| (values are weight %) | 1 | 2 | 3 | 4 | 5 | 6 | 7 | 8 | 9 | 10 | 11 | 12 |
|---|---|---|---|---|---|---|---|---|---|---|---|---|
| Propylene Glycol | | 1.00 | | | | | 1.0 | 1.0 | | 1.0 | | |
| Butylene Glycol | | 1.00 | | | | | 1.0 | 1.0 | | 1.0 | | |
| Tocopherol Acetate | | 0.50 | 0.2 | 0.2 | | | 0.5 | 0.5 | 0.5 | 0.5 | | 0.5 |
| N-Acetyl Glucosamine | 0.50 | | 2.0 | 2.0 | | | | | | | | |
| Hexamidine Diisethanoate *18 | 0.10 | | | | | | | | | | | |
| Niacinamide | 5.00 | 4.00 | 5.00 | 5.00 | | | 5 | 5.0 | 2.5 | 5.0 | | 2.5 |
| Methylparaben | 0.20 | 0.10 | | | | | 0.1 | | | | | |
| Ethylparaben | 0.05 | 0.10 | | | | | 0.1 | 0.1 | | 0.1 | | |
| Benzyl Alcohol | 0.25 | 0.50 | | | | | 0.4 | 0.4 | | 0.4 | 0.1 | |
| Propyl Paraben | | 0.10 | | | | | | 0.1 | | 0.1 | | |
| Disodium EDTA | | 0.10 | 0.05 | 0.05 | | | 0.1 | | 0.1 | | | 0.1 |
| Polysorbate 20 | | | 0.6 | 0.6 | | | | 0.8 | | 0.8 | | |
| Glydant Plus Liquid *19 | | | 0.3 | 0.3 | | | | | | | | |
| Laureth-4 | | | 0.2 | 0.2 | | | | 0.2 | | 0.2 | | |
| Sucrose Polycottonseedate | | | | | | | 0.5 | | | | | |
| Allantoin | | | | | | | 0.1 | 0.2 | | 0.2 | | |
| Prodew 400 *20 | | | | | | | | | | | | |
| GLW75CAP-MP *21 | | | | | | | | 0.35 | | 0.35 | | |
| Hydrolyzed wheat protein | | | | | | | | | 2.0 | | | |
| Menthol | | | | | | | | | | | | 0.5 |
| Vanillyl alcohol isoamyl ether monophosphate | | | | | | | | | | | | 0.05 |
| Sodium Chloride | 0.50 | | | | | | | | | | | |
| FD&C Red No. 40 | | | | | | | .00025 | | | | | |
| FD&C Blue 1 | | | | | | | .0001 | | | | | |
| Sepigel 305 *22 | | | 1.6 | | | | | 1.5 | 1.5 | 1.5 | | 1.5 |
| Water | q.s to 100 | q.s to 100 | q.s to 100 | q.s to 100 | | | q.s to 100 | q.s to 100 | q.s to 100 | q.s to 100 | | q.s to 100 |
| pH Tuneable Gellant *23 | | | | | | | 0.001%-10% | | | | | |

*1 12.5% Dimethicone Crosspolymer in Cyclopentasiloxane. Available from Dow Corning.
*2 Dimethicone Crosspolymer in Cyclopentasiloxane. Available from Dow Corning.
*3 E.g., Tospearl 145A or Tospearl 2000. Available from GE Toshiba Silicone
*4 PFM (250-500 μm) colored beads from Kobo.
*5 25% Dimethicone PEG-10/15 Crosspolymer in Dimethicone. Available from Shin-Etsu
*6 PEG-15/Lauryl Dimethicone Crosspolymer in Mineral Oil from Shin-Etsu.
*7 Jeenate 3H polyethylene wax. Available from Jeen
*8 Stearyl Dimethicone. Available from Dow Corning.
*9 Bis-PEG/PPG-14/14 Dimethicone. Available from Degussa
*10 PEG-10 Dimethicone. Available from Shin-Etsu.
*11 Hydrophobically modified $TiO_2$ coated Mica. Available from Kobo.
*12 Dimethicone/Dimethiconol blend from Dow Corning.
*13 Polymethylsilsesquioxane from General Electric.
*14 Mica and iron oxides from Eckart.
*15 Polyethylene powder available from Equistar.
*16 Dioleoylethyl hydroxyethylmonium methosulfate mixture available from Degussa Care & Surface Specialties, Hopewell, VA.
*17 Behenyltrimethylammonium chloride in carrier available from Sanyo Performance Chemicals, JP.
*18 Hexamidine diisethionate, availabile from Laboratoires Serobiologiques.
*19 DMDM Hydantoin and Iodopropynyl Butylcarbamate blend available from Lonza, Inc.
*20 Available from Ajinomoto U.S.A., Inc., Paramus NJ.
*21 $TiO_2$ with water, glycerine, polyacrylate, and methylparaben available from Kobo Products.
*22 Polyacrylamide, C13-14 Isoparaffin, and Laureth-7 blend from Seppic.
*23 While not to be read as limiting, exemplary pH tuneable gellants for basic or neutral examples include N,N'-(2S,2'S)- 1,1'-(hexane-1,6-diylbis(azanediyl))bis(3-methyl-1-oxobutane-2,1-diyl)diisonicotinamide; N,N'-(2S,2'S)-1,1'-(octane- 1,8-diylbis(azanediyl))bis(3-methyl-1-oxobutane-2,1-diyl)diisonicotinamide; and N,N'-(2S,2'S)-1,1'-(dodecane-1,12- diylbis (azanediyl))bis(3-methyl-1-oxobutane-2,1-diyl)diisonicotinamide. Exemplary pH tuneable gellants for acidic examples include (6S,14S')-6,14-diisopropyl-4,7,13,16-tetraoxo-5,8,12,15-tetraazanonadecane-1,19-dioic acid and (6S,23S)-6,23-diisopropyl-4,7,22,25-tetraoxo-5,8,21,24-tetraazaoctacosane-1,28-dioic acid. In certain examples, the pH tuneable gellant amounts may be from about 0.01% to about 3%.

For example 1, combine the ingredients of Phase A in a suitable container. In a separate suitable container, combine the ingredients of Phase B. Heat each phase to 75-80° C. while mixing each phase using a suitable mixer (e.g., Anchor blade, propeller blade) until each reaches temperature and is homogenous. Slowly add Phase B to Phase A while continuing to mix Phase A. Continue mixing until batch is uniform. Homogenize product with Ultra-Turrax homogenizer (IKA, Inc) or equivalent and pour product into suitable containers at 75-80° C. Store the containers at room temperature without disturbing for at least 12 hours.

For examples 2-4, 7-10, and 12, in a suitable container, combine the ingredients of Phase A and mix with a suitable mixer (with heat if needed) until homogenous. In a separate container, combine the ingredients of Phase B and mix with a suitable mixer (with heat if needed) until homogenous. Slowly add Phase B to Phase A while continuing to mix Phase A. Continue mixing (with heat if needed) until batch is uniform. Homogenize product with Ultra-Turrax homogenizer (IKA, Inc) or equivalent and pour product into suitable containers.

For examples 5-6 and 11, in a suitable vessel, the ingredients are combined and mixed (with heat if needed) until uniform; the composition may be warmed to dissolve all ingredients. Once the composition is uniform, the product is poured into suitable containers.

In all examples, the pH tuneable gellant may be added via a premix containing the designed amount of gellant and suitable amount of carrier fluid from the phase to be structured.

Methods of Using the Personal Care Compositions

The personal care compositions of the present invention may be useful for improving or regulating a number of keratinous tissue conditions. As used in relation to methods of using the personal care compositions, "regulating" means maintaining skin appearance and/or feel of the keratinous tissue with little to no degradation in appearance and/or feel, and "improving" means affecting a positive change in keratinous tissue appearance and/or feel. The keratinous tissue appearance and/or feel benefit may be an acute or chronic benefit.

Keratinous tissue conditions that may be regulated or improved include, but are not limited to thickening keratinous tissue (e.g., building the epidermis and/or dermis and/or subcutaneous layers of the skin or lips and where applicable the keratinous layers of the nail and hair shaft including eye lashes), atrophy, softening and/or smoothing, itch, appearance of dark under-eye circles and/or puffy eyes, sallowness, sagging (e.g., glycation), tanning, desquamating, exfoliating, and/or increasing turnover in mammalian skin, pores size, oily/shiny appearance, hyperpigmentation such as post-inflammatory hyperpigmentation, spider vessels and/or red blotchiness on mammalian skin, fine lines and wrinkles, dryness (e.g., roughness, scaling, flaking), cellulite, and acne.

Other keratinous conditions that may be regulated or improved include signs of skin aging including, but not limited to, all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

The personal care compositions of the present invention may be useful for improving or regulating insult-affected keratinous tissue. "Insult-affected keratinous tissue," means keratinous tissue which exhibits discomfort, irritation, an unpleasant or irregular appearance, and the like, for example after exposure to a physical and/or chemical irritant. Non-limiting examples of insult-affected keratinous tissue include burn (e.g., sunburns, windburn, chemical or thermal burns); rashes (e.g., diaper rash, shaving rash and allergen-induced rashes); discoloration (e.g., bleaching, staining, hyperpigmentation); nicks and cuts (e.g., shaving insults); and dry, chapped or rough skin (e.g., due to exposure to example wind, cold and/or low humidity). Non-limiting examples of insults include radiation, wind, low humidity, allergens, pollutants, chemical and natural irritants, bodily fluids, bodily waste, excessive moisture, bacteria, fungi, etc.

Regulating and improving keratinous tissue condition involves topically applying to the keratinous tissue a safe and effective amount of a composition of the present invention. The amount of the composition that is applied, the frequency of application and the period of use will vary widely depending upon the actives and other components of a given composition and the level of regulation or improvement desired.

In certain embodiments, the composition is chronically applied to the keratinous tissue and, more specifically, the skin. By "chronic topical application" is meant routine or periodic application of the composition over a time period during the subject's lifetime. Suitable time periods include at least about one week, at least about one month, at least about three months, at least about six months, and at least about one year. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions, which are typically applied per application, are, in mg of composition per $cm^2$ of keratinous tissue and, more specifically, the skin A suitable application quantity is from about 0.1 $mg/cm^2$ to about 20 $mg/cm^2$ or from about 0.5 $mg/cm^2$ to about 10 $mg/cm^2$.

Suitable keratinous tissues to which the compositions may be employed include any part of the external portion of the face, hair, and/or nails. For example, the personal care composition may be applied to the face, lips, under-eye area, eyelids, scalp, neck, torso, arms, hands, legs, fingernails, toenails, scalp hair, eyelashes, eyebrows, and the like. In one embodiment the personal care composition is applied to a "facial skin surface," which refers to one or more of the forehead, periorbital, cheek, perioral, chin, and nose skin surfaces.

Leave-on compositions may be left on the keratinous tissue for a period of at least about 15 minutes, at least about 30 minutes, at least about 1 hour, or for several hours (e.g., over 12 hours).

The application of the present compositions may be done using, e.g., the palms of the hands and/or fingers, an implement, e.g., a cotton ball, swab, pad etc.

The composition can be dispensed from a bottle, jar, tube, sachet, pouch, container, bottle, vial, ampoule, compact, etc. or can be integrally contained within a delivery form such as a wipe. The application of the present compositions may be done using the palms of the hands and/or fingers. The application may also be done with the aid of a device or implement such as a cotton ball, swab, pad, brush, eye dropper, puff, sponge, wand, wipe, foam, nonwoven substrate, mask, roll-on applicator, stick applicator, applicator pen, spray applicator, atomizer, razor, etc. The active may be contained in a rupturable pouch between two substrates.

Test Methods

1. Turbidity (NTU)—The turbidity (measured in NTU: Nephelometric Turbidity Units) is measured using a Hach 2100P turbidity meter calibrated according to the procedure provided by the manufacture. The sample vials are filled with 15 ml of representative sample and capped and cleaned according to the operating instructions. If necessary, the samples are degassed to remove any bubbles either by applying a vacuum or using an ultrasonic bath (see operating manual for procedure). The turbidity is measured using the automatic range selection.

2. Viscosity—Viscosities are measured on a Brookfield viscometer using a T-C bar spindle with a heliopath setting at 5 rpm at 25° C.

3. Minimum gelling concentration (MGC)—MGC is calculated by a tube inversion method based on R. G. Weiss, P. Terech; "Molecular Gels: Materials with self-assembled fibrillar structures" 2006, Springer, p. 243. In order to determine the MGC, three screenings are done:

a) First screening: prepare several vials increasing the pH tuneable gellant concentration from 0.5% to 5.0 weight % in 0.5% steps
b) Determine in which interval the gel is formed (one inverted sample still flowing and the next one is already a strong gel). In case no gel is formed at 5%, higher concentrations are used.
c) Second screening: prepare several vials increasing the pH tuneable gellant concentration in 0.1 weight % steps in the interval determined in the first screening.
d) Determine in which interval the gel is formed (one inverted sample still flowing and the next one is already a strong gel)
e) Third screening: in order to have a very precise percentage of the MGC, run a third screening in 0.025 weight % steps in the interval determined in the second screening.
f) The Minimum Gelling Concentration (MGC) is the lowest concentration which forms a gel in the third screening (does not flow on inversion of the sample).

For each screening, samples are prepared and treated as follows: 8 mL vials (Borosilacate glass with Teflon cap, ref. B7857D, Fisher Scientific Bioblock) are filled with 2.0000±0.0005 g (KERN ALJ 120-4 analytical balance with ±0.1 mg precision) of the liquid (comprising the liquid detergent composition and pH Tuneable gellant) for which we want to determine the MGC. The vial is sealed with the screw cap and left for 10 minutes in an ultrasound bath (Elma Transsonic T 710 DH, 40 kHz, 9.5 L, at 25° C. and operating at 100% power) in order to disperse the solid in the liquid. Complete dissolution is then achieved by heating, using a heating gun (Bosch PHG-2), and gentle mechanical stirring of the vials. It is crucial to observe a completely clear solution. Handle vials with care. While they are manufactured to resist high temperatures, a high solvent pressure may cause the vials to explode. Vials are cooled to 25° C., for 10 min in a thermostatic bath (Compatible Control Thermostats with controller CC2, D77656, Huber). Vials are inverted, left inverted for 1 minute, and then observed for which samples do not flow. After the third screening, the concentration of the sample that does not flow after this time is the MGC. For those skilled in the art, it is obvious that during heating solvent vapours may be formed, and upon cooling down the samples, these vapours can condense on top of the gel. When the vial is inverted, this condensed vapour will flow. This is discounted during the observation period. If no gels are obtained in the concentration interval, higher concentrations must be evaluated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising a pH tuneable gellant, wherein the pH tuneable gellant has a formula selected from the group consisting of:
   a.

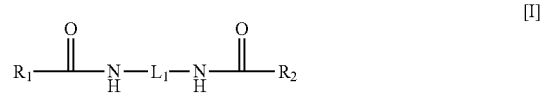

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group;
   b.

wherein $R_5$ is an aminofunctional moiety; $L_2$ is a backbone moiety having molecular weight from 14 to 500 g/mol; and at least one of $L_2$ or $R_5$ comprises a pH-sensitive group; and
   c. mixtures thereof;
   wherein the pH tuneable gellant has a pKa of from 1 to 30; and
   wherein the personal care composition is a leave-on and wherein the personal care composition is an emulsion having an aqueous phase and an oil phase.

2. A personal care composition in the form of an emulsion comprising an aqueous phase, an oil phase, and a pH tuneable gellant, has a formula selected from the group consisting of:
   a.

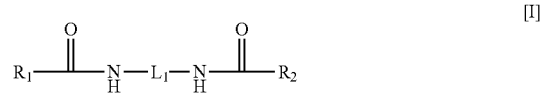

wherein $R_1$ and $R_2$ are aminofunctional end-groups; $L_1$ is a backbone moiety having molecular weight from 14 to 500 g/mol; and at least one of $L_1$, $R_1$ or $R_2$ comprises a pH-sensitive group;
   b.

wherein R₅ is an aminofunctional moiety; L₂ is a backbone moiety having molecular weight from 14 to 500 g/mol; and at least one of L₂ or R₅ comprises a pH-sensitive group; and c. mixtures thereof; wherein the pH tuneable gellant has a pKa of from 1 to 30, and wherein the personal care composition comprises less than 1% of a detersive surfactant.

3. A personal care composition comprising
a. a pH tuneable gellant, has a formula selected from the group consisting of:
i.

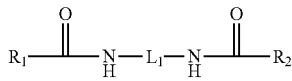

[I]

wherein R₁ and R₂ are aminofunctional end-groups; L₁ is a backbone moiety having molecular weight from 14 to 500 g/mol; and at least one of L₁, R₁ or R₂ comprises a pH-sensitive group;
ii.

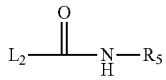

[II]

wherein R₅ is an aminofunctional moiety; L₂ is a backbone moiety having molecular weight from 14 to 500 g/mol; and at least one of L₂ or R₅ comprises a pH-sensitive group; and
iii. mixtures thereof; wherein the pH tuneable gellant has a pKa of from 1 to 30; and b. an active or agent selected from a group consisting of sugar amines, vitamins, oil control agents, photosterols, hexamidine compounds, tightening agents, anti-wrinkle actives, anti-atrophy actives, flavonoids, N-acyl amino acid compounds, retinoids, peptides, particulate materials, UV actives, photostabilizers, anti-cellulite agents, desquamation actives, anti-acne actives, anti-oxidants, radical scavengers, conditioning agents, anti-inflammatory agents, tanning actives, skin lightening agents, botanical extracts, antimicrobial actives, antifungal actives, antibacterial actives, antiperspirant actives, sensates, preservatives, anti-dandruff actives, substantivity polymers, detersive surfactants, and combinations thereof, wherein the personal care composition is a topical composition.

4. The personal care composition of claim 1, 2, or 3, wherein the pH tuneable gellant has a pKa of from 1.5 to 14.

5. The personal care composition of claim 1, 2, or 3, wherein the pH tuneable gellant has a molecular weight from 150 to 1500 g/mol.

6. The personal care composition of claim 1, 2, or 3, wherein the pH tuneable gellant has a minimum gelling concentration (MGC) of from 0.1 to 100 mg/mL, at the pH of the composition.

7. The personal care composition of claim 1, 2, or 3, wherein the pH tuneable amido gellant is selected from the group: N,N'-(2S,2'S)-1,1'-(ethane-1,2-diylbis(azanediyl))bis(3-methyl-1-oxobutane-2,1-diyl)diisonicotinamide; N,N'-(2S,2'S)-1,1'-(propane-1,3-diylbis(azanediyl))bis(3-methyl-1-oxobutane-2,1-diyl)diisonicotinamide; N,N'-(2S,2'S)-1,1'-(butane-1,4-diylbis(azanediyl))bis(3-methyl-1-oxobutane-2,1-diyl)diisonicotinamide; N,N'-(2S,2'S)-1,1'-(pentane-1,5-diylbis(azanediyl))bis(3-methyl-1-oxobutane-2,1-diyl) diisonicotinamide; N,N'-(2S,2'S)-1,1'-(hexane-1,6-diylbis(azanediyl))bis(3-methyl-1-oxobutane-2,1-diyl) diisonicotinamide; N,N'-(2S,2'S)-1,1'-(heptane-1,7-diylbis(azanediyl))bis(3-methyl-1-oxobutane-2,1-diyl) diisonicotinamide; N,N'-(2S,2'S)-1,1'-(octane-1,8-diylbis(azanediyl))bis(3-methyl-1-oxobutane-2,1-diyl) diisonicotinamide; (6S,13S')-6,13-diisopropyl-4,7,12,15-tetraoxo-5,8,11,14-tetraazaoctadecane-1,18-dioic acid; (6S,14S')-6,14-diisopropyl-4,7,13,16-tetraoxo-5,8,12,15-tetraazanonadecane-1,19-dioic acid; (6S,15S')-6,15-diisopropyl-4,7,14,17-tetraoxo-5,8,13,16-tetraazaeicosane-1,20-dioic acid; (6S,16S')-6,16-diisopropyl-4,7,15,18-tetraoxo-5,8,14,17-tetraazaheneicosane-1,21-dioic acid; (6S,17S')-6,17-diisopropyl-4,7,16,19-tetraoxo-5,8,15,18-tetraazadocosane-1,22-dioic acid; (6S,18S')-6,18-diisopropyl-4,7,17,20-tetraoxo-5,8,16,19-tetraazatricosane-1,23-dioic acid; (6S,19S')-6,19-diisopropyl-4,7,18,21-tetraoxo-5,8,17,20-tetraazatetracosane-1,24-dioic acid; (6S,20S')-6,20-diisopropyl-4,7,19,22-tetraoxo-5,8,18,21-tetraazapentacosane-1,25-dioic acid; (6S,21S')-6,21-diisopropyl-4,7,20,23-tetraoxo-5,8,19,22-tetraazahexacosane-1,26-dioic acid; (6S,22S')-6,22-diisopropyl-4,7,21,24-tetraoxo-5,8,20,23-tetraazaheptacosane-1,27-dioic acid; (6S,23S')-6,23-diisopropyl-4,7,22,25-tetraoxo-5,8,21,24-tetraazaoctacosane-1,28-dioic acid; N,N'-(2S,2'S)-1,1'-(ethane-1,2-diylbis(azanediyl))bis(3-methyl-1-oxobutane-2,1-diyl)bis(4-(1H-imidazol-5-yl)benzamide); N,N'-(2S,2'S)-1,1'-(propane-1,3-diylbis(azanediyl))bis(3-methyl-1-oxobutane-2,1-diyl)bis(4-(1H-imidazol-5-yl)benzamide N,N'-(2S,2'S)-1,1'-(butane-1,4-diylbis(azanediyl))bis(3-methyl-1-oxobutane-2,1-diyl)bis(4-(1H-imidazol-5-yl)benzamide); N,N'-(2S,2'S)-1,1'-(pentane-1,5-diylbis(azanediyl))bis(3-methyl-1-oxobutane-2,1-diyl)bis(4-(1H-imidazol-5-yl)benzamide); N,N'-(2S,2'S)-1,1'-(hexane-1,6-diylbis(azanediyl))bis(3-methyl-1-oxobutane-2,1-diyl)bis(4-(1H-imidazol-5-yl)benzamide); N,N'-(2S,2'S)-1,1'-(heptane-1,7-diylbis(azanediyl))bis(3-methyl-1-oxobutane-2,1-diyl)bis(4-(1H-imidazol-5-yl)benzamide); N,N'-(2S,2'S)-1,1'-(octane-1,8-diylbis(azanediyl))bis(3-methyl-1-oxobutane-2,1-diyl)bis(4-(1H-imidazol-5-yl)benzamide); N,N'-(2S,2'S)-1,1'-(nonane-1,9-diylbis(azanediyl))bis(3-methyl-1-oxobutane-2,1-diyl)bis(4-(1H-imidazol-5-yl)benzamide); N,N'-(2S,2'S)-1,1'-(decane-1,10-diylbis(azanediyl))bis(3-methyl-1-oxobutane-2,1-diyl)bis(4-(1H-imidazol-5-yl)benzamide); N,N'-(2S,2'S)-1,1'-(undecane-1,11-diylbis(azanediyl))bis(3-methyl-1-oxobutane-2,1-diyl)bis(4-(1H-imidazol-5-yl)benzamide); N,N'-(2S,2'S)-1,1'-(dodecane-1,12-diylbis(azanediyl))bis(3-methyl-1-oxobutane-2,1-diyl) bis(4-(1H-imidazol-5-yl)benzamide); N,N'-(2S,2'S)-1,1'-(nonane-1,9-diylbis(azanediyl))bis(3-methyl-1-oxobutane-2,1-diyl)diisonicotinamide; N,N'-(2S,2'S)-1,1'-(decane-1,10-diylbis(azanediyl))bis(3-methyl-1-oxobutane-2,1-diyl) diisonicotinamide; N,N'-(2S,2'S)-1,1'-(undecane-1,11-diylbis(azanediyl))bis(3-methyl-1-oxobutane-2,1-diyl) diisonicotinamide; N,N'-(2S,2'S)-1,1'-(dodecane-1,12-diylbis(azanediyl))bis(3-methyl-1-oxobutane-2,1-diyl) diisonicotinamide; N,N'-(2S,2'S)-1,1'-(tridecane-1,13-diylbis(azanediyl))bis(3-methyl-1-oxobutane-2,1-diyl) diisonicotinamide; N,N'-(2S,2'S)-1,1'-(tetradecane-1,14-diylbis(azanediyl))bis(3-methyl-1-oxobutane-2,1-diyl) diisonicotinamide; N,N'-(2S,2'S)-1,1'-(hexadecane-1,16-diylbis(azanediyl))bis(3-methyl-1-oxobutane-2,1-diyl)

diisonicotinamide; N,N'-(2S,2'S)-1,1'-(octadecane-1,18-diylbis(azanediyl))bis(3-methyl-1-oxobutane-2,1-diyl) diisonicotinamide; N,N'-(2S,2'S)-1,1'-(ethane-1,2-diylbis(azanediyl))bis(1-oxopropane-2,1-diyl)diisonicotinamide; N,N'-(2S,2'S)-1,1'-(propane-1,3-diylbis(azanediyl))bis(1-oxopropane-2,1-diyediisonicotinamide; N,N'-(2S,2'S)-1,1'-(butane-1,4-diylbis(azanediyl))bis(1-oxopropane-2,1-diyl) diisonicotinamide; N,N'-(2S,2'S)-1,1'-(pentane-1,5-diylbis(azanediyl))bis(1-oxopropane-2,1-diyl)diisonicotinamide; N,N'-(2S,2'S)-1,1'-(hexane-1,6-diylbis(azanediyl))bis(1-oxopropane-2,1-diyl)diisonicotinamide; N,N'-(2S,2'S)-1,1'-(heptane-1,7-diylbis(azanediyl))bis(1-oxopropane-2,1-diyediisonicotinamide; N,N'-(2S,2'S)-1,1'-(octane-1,8-diylbis(azanediyl))bis(1-oxopropane-2,1-diyl)diisonicotinamide; N,N'-(2S,2'S)-1,1'-(nonane-1,9-diylbis(azanediyl))bis(1-oxopropane-2,1-diyl)diisonicotinamide; N,N'-(2S,2'S)-1,1'-(decane-1,10-diylbis(azanediyl))bis(1-oxopropane-2,1-diyl) diisonicotinamide; N,N'-(2S,2'S)-1,1'-(undecane-1,11-diylbis(azanediyl))bis(1-oxopropane-2,1-diyediisonicotinamide; N,N'-(2S,2'S)-1,1'-(dodecane-1,12-diylbis(azanediyl))bis(1-oxopropane-2,1-diyl) diisonicotinamide; N,N'-(2S,2'S)-1,1'-(tridecane-1,13-diylbis(azanediyl))bis(1-oxopropane-2,1-diyediisonicotinamide; N,N'-(2S,2'S)-1,1'-(tetradecane-1,14-diylbis(azanediyl))bis(1-oxopropane-2,1-diyl) diisonicotinamide; N,N'-(2S,2'S)-1,1'-(hexadecane-1,16-diylbis(azanediyl))bis(1-oxopropane-2,1-diyl) diisonicotinamide; N,N'-(2S,2'S)-1,1'-(octadecane-1,18-diylbis(azanediyl))bis(1-oxopropane-2,1-diyl) diisonicotinamide; N,N'-(2S,2'S)-1,1'-(ethane-1,2-diylbis(azanediyl))bis(1-oxo-3-phenylpropane-2,1-diyl) diisonicotinamide; N,N'-(2S,2'S)-1,1'-(propane-1,3-diylbis(azanediyl))bis(1-oxo-3-phenylpropane-2,1-diyl) diisonicotinamide; N,N'-(2S,2'S)-1,1'-(butane-1,4-diylbis(azanediyl))bis(1-oxo-3-phenylpropane-2,1-diyediisonicotinamide; N,N'-(2S,2'S)-1,1'-(pentane-1,5-diylbis(azanediyl))bis(1-oxo-3-phenylpropane-2,1-diyl) diisonicotinamide; N,N'-(2S,2'S)-1,1'-(hexane-1,6-diylbis(azanediyl))bis(1-oxo-3-phenylpropane-2,1-diyl) diisonicotinamide N,N'-(2S,2'S)-1,1'-(heptane-1,7-diylbis(azanediyl))bis(1-oxo-3-phenylpropane-2,1-diyediisonicotinamide; N,N'-(2S,2'S)-1,1'-(octane-1,8-diylbis(azanediyl))bis(1-oxo-3-phenylpropane-2,1-diyl) diisonicotinamide; N,N'-(2S,2'S)-1,1'-(nonane-1,9-diylbis(azanediyl))bis(1-oxo-3-phenylpropane-2,1-diyl) diisonicotinamide; N,N'-(2S,2'S)-1,1'-(decane-1,10-diylbis(azanediyl))bis(1-oxo-3-phenylpropane-2,1-diyediisonicotinamide; N,N'-(2S,2'S)-1,1'-(undecane-1,11-diylbis(azanediyl))bis(1-oxo-3-phenylpropane-2,1-diyl) diisonicotinamide; N,N'-(2S,2'S)-1,1'-(dodecane-1,12-diylbis(azanediyl))bis(1-oxo-3-phenylpropane-2,1-diyl) diisonicotinamide; N,N'-(2S,2'S)-1,1'-(tridecane-1,13-diylbis(azanediyl))bis(1-oxo-3-phenylpropane-2,1-diyl) diisonicotinamide; N,N'-(2S,2'S)-1,1'-(tetradecane-1,14-diylbis(azanediyl))bis(1-oxo-3-phenylpropane-2,1-diyl) diisonicotinamide; N,N'-(2S,2'S)-1,1'-(hexadecane-1,16-diylbis(azanediyl))bis(1-oxo-3-phenylpropane-2,1-diyl) diisonicotinamide; N,N'-(2S,2'S)-1,1'-(octadecane-1,18-diylbis(azanediyl))bis(1-oxo-3-phenylpropane-2,1-diyl) diisonicotinamide; (2S)-2-[[2-(dodecanoylamino)acetyl]amino]propanoic acid; (2S)-2-[[2-[[2-(dodecanoylamino)acetyl]amino]acetyl]amino]propanoic acid; (2S)-2-[[2-(dodecanoylamino)acetyl]amino]-2-phenyl-acetic acid; (2S)-2-[[2-(dodecanoylamino)acetyl]amino]-3-methyl-butanoic acid; 2-[[2-(dodecanoylamino)acetyl]amino]acetic acid; (2S)-2-[[2-(hexadecanoylamino)acetyl]amino]propanoic acid; and mixtures thereof.

8. The personal care composition of claim 3 wherein the personal care composition is an emulsion having an aqueous phase and an oil phase.

9. The personal care composition of claim 2 or 8 wherein the pH tuneable gellant structures the aqueous phase.

10. The personal care composition of claim 2 or 8 wherein the pH tuneable gellant structures the oil phase.

11. The personal care composition of claim 2 or 8 further comprising an emulsifier.

12. The personal care composition of claim 11, wherein the emulsifier is selected from ethers or esters of glycerol, polyglycerol, sucrose, glucose, and sorbitol.

13. The personal care composition of claim 1, 2, or 3 further comprising from about 1% to about 95%, by weight of the composition, water.

14. The personal care composition of claim 1, 2, or 3 further comprising from about 1% to about 95%, by weight of the composition, oil.

15. The personal care composition of claim 14 wherein the oil is selected from a group consisting of linear silicones, cyclic silicones, paraffinic hydrocarbons, fatty esters, hydrocarbon oils, cationic silicone fluids, and combinations thereof.

16. The personal care composition of claim 1, 2, or 3 further comprising an additional structuring agent selected from a group consisting of polysaccharides, gums, carboxylic acid polymers, sulfonated polymers, acrylamide polymers, polyalkylglycols, polyglycerins, silicone elastomers, silicone gums, silicone waxes, polyamides, polysilicone-polyamide copolymers, natural and synthetic waxes, natural and synthetic montmorillonite minerals, silicas, silicates, derivatives thereof, and combinations thereof.

17. The personal care composition of claim 1 or 2 further comprising an active or agent selected from a group consisting of sugar amines, vitamins, dehydroacetic acid and salts, photosterols, hexamidine compounds, dialkanoyl hydroxyproline and salts, flavonoids, N-acyl amino acid compounds, retinoids, peptides, particulates, UV actives, anti-cellulite agents, butylated hydroxytoluene, butylated hydroxyanisole, desquamation actives, anti-acne actives, anti-wrinkle actives, anti-atrophy actives, conditioning agents, anti-oxidants, radical scavengers, anti-inflammatory agents, tanning actives, skin lightening agents, botanical extracts, antimicrobial actives, antifungal actives, antibacterial actives, antiperspirant actives, anti-dandruff actives, humectants, terpene alcohols, and combinations thereof.

18. The personal care composition of claim 3 or 17 wherein the vitamins are selected from vitamin B3 compound, ascorbic acid, tocopherol acetate, panthenol, dexpanthenol, magnesium ascorbyl phosphate, sodium ascorbyl phosphate, retinyl propionate, and combinations thereof.

19. The personal care composition of claim 3 or 17 wherein the active or agent is selected from glucosamine, glucosamine derivatives, salts of dehydroacetic acid, salicylic acid, hexamidine diisethionate, salts of dialkanoyl hydroxyproline, N-acyl phenylalanine, dipeptides, pentapeptides, titanium dioxide, iron oxide, zinc oxide, butylated hydroxytoluene, dihydroxyacetone, and combinations thereof.

20. The personal care composition of claim 1, 2, or 3 wherein the composition is paraben free.

21. The personal care composition of claim 1 or 3 wherein the composition comprises less than 1% of a detersive surfactant.

22. The personal care composition of claim 1, 2, or 3 wherein the composition comprises no detersive surfactant.

* * * * *